US006752154B2

(12) United States Patent
Fogarty et al.

(10) Patent No.: US 6,752,154 B2
(45) Date of Patent: Jun. 22, 2004

(54) DEVICE FOR ACCURATELY MARKING TISSUE

(75) Inventors: Thomas J. Fogarty, 3270 Alpine Rd., Portola Valley, CA (US) 94028; David B. Willis, Palo Alto, CA (US); Thomas A. Howell, Palo Alto, CA (US); George D. Hermann, Portola Valley, CA (US); Peter M. Wilson, Foster City, CA (US); Elizabeth M. Bush, Fremont, CA (US); Steven W. Kim, San Jose, CA (US); Roman Turovskiy, San Francisco, CA (US)

(73) Assignee: Thomas J. Fogarty, Portola Valley, CA (US)

( * ) Notice: Subject to any disclaimer, the term of this patent is extended or adjusted under 35 U.S.C. 154(b) by 94 days.

(21) Appl. No.: 09/935,477

(22) Filed: Aug. 22, 2001

(65) Prior Publication Data

US 2002/0059938 A1 May 23, 2002

Related U.S. Application Data

(63) Continuation-in-part of application No. PCT/US01/05013, filed on Feb. 16, 2001, which is a continuation-in-part of application No. 09/699,254, filed on Oct. 27, 2000, which is a continuation-in-part of application No. 09/613,686, filed on Jul. 11, 2000, now Pat. No. 6,405,733, which is a continuation-in-part of application No. 09/507,361, filed on Feb. 18, 2000.

(51) Int. Cl.[7] .............................................. A61B 19/00
(52) U.S. Cl. ...................... 128/899; 606/116; 600/434
(58) Field of Search ................................ 128/897–899; 600/424, 434, 562; 606/116, 151, 159, 170

(56) References Cited

U.S. PATENT DOCUMENTS 2,022,065 A 11/1935 Wappler (List continued on next page.)

FOREIGN PATENT DOCUMENTS

| EP | 0 385 604 | 5/1990 |
| EP | 0 395 997 | 7/1990 |

(List continued on next page.)

OTHER PUBLICATIONS

Anonymous. *Ariadne's Thread™ Repositionable Breast Localisation Needle*, (Product Information), one page (date not known).

(List continued on next page.)

*Primary Examiner*—John P. Lacyk
(74) *Attorney, Agent, or Firm*—Morrison & Foerster LLP

(57) ABSTRACT

This invention is an improved tissue localizing device for fixedly yet removably marking a volume of tissue containing a suspect region for excision. This invention also encompasses methods for deployment of the localizing device and its excision along with the marked tissue volume. At least one locator element is deployed into tissue and assumes a predetermined curvilinear shape to define a tissue border containing a suspect tissue region along a path. The locator element path preferably encompasses the distalmost portion of the tissue volume without penetrating that volume. Multiple locator elements may be deployed to further define the tissue volume along additional paths defining the tissue volume border that do not penetrate the volume. Other localization wire embodiments of the invention are disclosed in which the tissue volume may be penetrated by a portion of the device. Polar and tangential deployment configurations as well as a locator element that may be cold-formed by a die in the distal portion of the deployment tube into a permanent arcuate shape are also disclosed.

15 Claims, 47 Drawing Sheets

U.S. PATENT DOCUMENTS

| | | |
|---|---|---|
| 2,047,535 A | 7/1936 | Wappler |
| 3,330,278 A | 7/1967 | Santomieri |
| 3,351,463 A | 11/1967 | Rozner et al. |
| 3,516,412 A | 6/1970 | Ackerman |
| 3,714,851 A | 2/1973 | Orser |
| 3,753,700 A | 8/1973 | Harrison et al. |
| 3,890,977 A | 6/1975 | Wilson |
| 4,010,756 A | 3/1977 | DuMont et al. |
| 4,103,690 A | 8/1978 | Harris |
| 4,274,408 A | 6/1981 | Nimrod |
| 4,341,226 A | 7/1982 | Peters |
| 4,402,328 A | 9/1983 | Doring |
| 4,592,356 A | 6/1986 | Gutierrez |
| 4,595,007 A | 6/1986 | Mericle |
| 4,616,656 A | 10/1986 | Nicholson et al. |
| 4,633,880 A | 1/1987 | Osypka et al. |
| 4,665,906 A | 5/1987 | Jervis |
| 4,682,606 A | 7/1987 | DeCaprio |
| 4,799,495 A | 1/1989 | Hawkins et al. |
| 4,869,259 A | 9/1989 | Elkins |
| 4,925,445 A | 5/1990 | Sakamoto et al. |
| 4,966,583 A | 10/1990 | Debbas |
| 5,011,473 A | 4/1991 | Gatturna |
| 5,018,530 A | 5/1991 | Rank et al. |
| 5,059,197 A | 10/1991 | Urie et al. |
| 5,067,957 A | 11/1991 | Jervis |
| 5,122,136 A | 6/1992 | Guglielmi et al. |
| 5,158,084 A | 10/1992 | Ghiatas |
| 5,183,463 A | 2/1993 | Debbas |
| 5,190,546 A | 3/1993 | Jervis |
| 5,197,482 A | 3/1993 | Rank et al. |
| 5,205,829 A | 4/1993 | Lituchy |
| 5,217,027 A | 6/1993 | Hermens |
| 5,221,269 A | 6/1993 | Miller et al. |
| 5,282,845 A | 2/1994 | Bush et al. |
| 5,300,068 A | 4/1994 | Rosar et al. |
| 5,301,682 A | 4/1994 | Debbas |
| 5,350,419 A | 9/1994 | Bendel et al. |
| 5,353,804 A | 10/1994 | Kornberg et al. |
| 5,409,004 A | 4/1995 | Sloan |
| 5,462,062 A | 10/1995 | Rubinstein et al. |
| 5,472,441 A | 12/1995 | Edwards et al. |
| 5,486,183 A | 1/1996 | Middleman et al. |
| 5,488,958 A | 2/1996 | Topel et al. |
| 5,507,743 A | 4/1996 | Edwards et al. |
| 5,536,267 A | 7/1996 | Edwards et al. |
| 5,540,683 A | 7/1996 | Ichikawa et al. |
| 5,556,410 A | 9/1996 | Mittermeir et al. |
| 5,558,673 A | 9/1996 | Edwards et al. |
| 5,672,173 A | 9/1997 | Gough et al. |
| 5,672,174 A | 9/1997 | Gough et al. |
| 5,683,384 A | 11/1997 | Gough et al. |
| 5,685,853 A | 11/1997 | Bonnet |
| 5,709,697 A | 1/1998 | Ratcliff et al. |
| 5,735,847 A | 4/1998 | Gough et al. |
| 5,741,225 A | 4/1998 | Lax et al. |
| 5,749,887 A | 5/1998 | Heske et al. |
| 5,794,626 A | 8/1998 | Kieturakis |
| 5,795,308 A | 8/1998 | Russin |
| 5,800,484 A | 9/1998 | Gough et al. |
| 5,807,339 A | 9/1998 | Bostrom et al. |
| 5,810,804 A | 9/1998 | Gough et al. |
| 5,853,366 A | 12/1998 | Dowlatshahi |
| 5,855,576 A | 1/1999 | LeVeen et al. |
| 5,863,290 A | 1/1999 | Gough et al. |
| 5,879,357 A | 3/1999 | Heaton et al. |
| 5,882,316 A | 3/1999 | Chu et al. |
| 5,902,310 A | 5/1999 | Foerster et al. |
| 5,904,690 A | 5/1999 | Middleman et al. |
| 5,941,890 A | 8/1999 | Voegele et al. |
| 5,954,655 A | 9/1999 | Hussman |
| 5,989,265 A | 11/1999 | Bouquet De La Joliniere et al. |
| 6,007,495 A | 12/1999 | Matula |
| 6,019,757 A | 2/2000 | Scheldrup |
| 6,022,362 A | 2/2000 | Lee et al. |
| 6,039,735 A | 3/2000 | Greep |
| 6,050,954 A | 4/2000 | Mittermeier |
| 6,051,008 A | 4/2000 | Saadat et al. |
| 6,053,876 A | 4/2000 | Fisher |
| 6,053,925 A | 4/2000 | Barnhart |
| 6,080,113 A | 6/2000 | Heneveld et al. |
| 6,080,114 A | 6/2000 | Russin |

FOREIGN PATENT DOCUMENTS

| | | |
|---|---|---|
| EP | 0 829 232 | 3/1998 |
| WO | WO 88/06864 | 9/1988 |
| WO | WO 92/12678 | 8/1992 |
| WO | WO 96/27328 | 9/1996 |
| WO | WO 99/04704 | 2/1999 |
| WO | WO 99/25248 | 5/1999 |
| WO | WO 99/43268 | 9/1999 |
| WO | WO 99/44506 | 9/1999 |
| WO | WO 99/58065 | 11/1999 |
| WO | WO 99/66834 | 12/1999 |
| WO | WO 00/10471 | 3/2000 |
| WO | WO 00/12009 | 3/2000 |
| WO | WO 00/12010 | 3/2000 |
| WO | WO 00/13602 | 3/2000 |
| WO | WO 00/16697 | 3/2000 |
| WO | WO 00/24320 | 5/2000 |
| WO | WO 00/28913 | 5/2000 |
| WO | WO 00/30531 | 6/2000 |
| WO | WO 00/33743 | 6/2000 |
| WO | WO 01/05317 | 1/2001 |
| WO | WO 01/05320 | 1/2001 |

OTHER PUBLICATIONS

Anonymous. (1999). *Auto Suture MIBB Site Marker: Single Use Clip Applier, United States Surgical* (Product instructions), 2 pages.

Anonymous. (1988). *Biopsy Needles and Trays, Cook Diagnostic and Interventional Products*, p. 3 (Products price list).

Anonymous. (1999). *MIBB Site Marker, United States Surgical* (Sales brochure), 4 pages.

Anonymous. (1987). *Homer Mammalok ® Breast Lesion Needle/Wire Localizer, Namic ® Angiographic Systems Division*, Glens Falls, New York, (Hospital products price list), 4 pages.

Anonymous. *Blunt Tubes with Finished Ends. Pointed Cannula, Popper & Sons Biomedical Instrument Division*, (Products Price List), one page (date not known).

Anoymous. *Ground Cannulae, ISPG*, New Milford, CT, (Advertisement) one page (date not known).

Gennari, R. et al. (Jun. 2000). "Use of Technetium–99m–Labeled Colloid Albumin for Preoperative and Intraoperative Localization of Nonpalpable Breast Lesions," *J. Am. Coll. Surg.* 190(6):692–699.

Kopans, D.B. et al. (Nov. 1985). "Spring Hookwire Breast Lesion Localizer: Use with Rigid–Compression. Mammographic Systems," *Radiology* 157(2):537–538.

Mullan, B.F. et al. (May 1999). "Lung Nodules: Improved Wire for CT–Guided Localization," *Radiology* 211:561–565.

Urrutia et al. (1988). "Retractable–Barb Needle for Breast Lesion Localization: Use in 60 Cases," *Radiology* 169(3):845–847.

MDTECH product literature, "FlexStrand", product description, Dec. 1999, 1 pg.

MDTECH product literature, "D Wire", product description, Mar. 2000, 2 pgs.

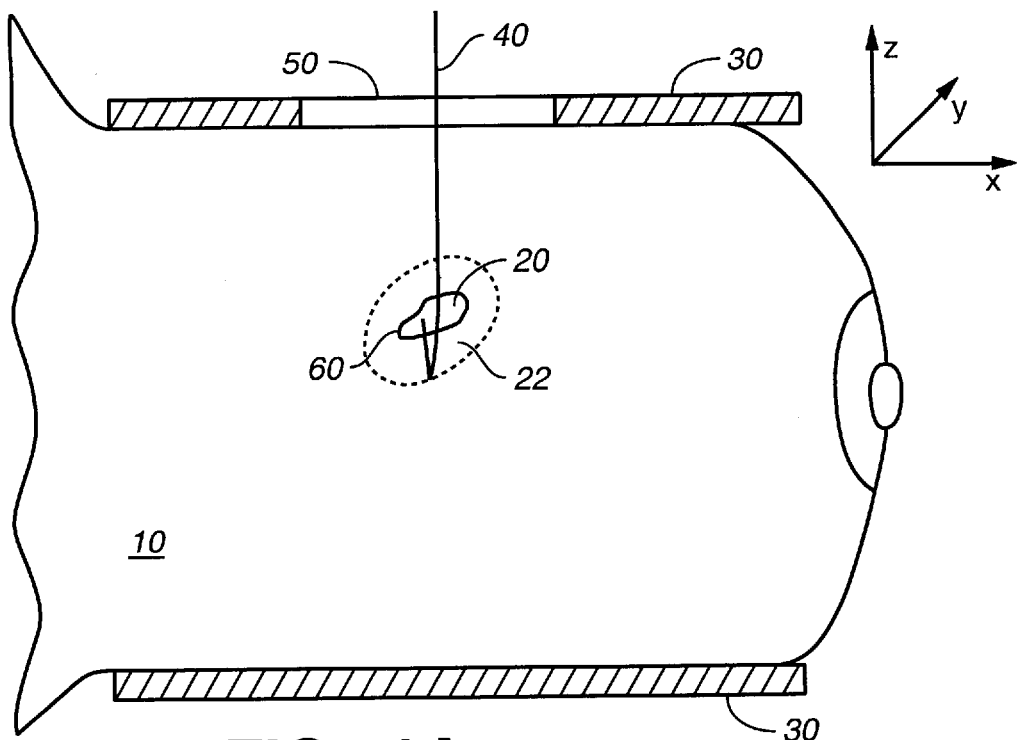
FIG._1A (PRIOR ART)
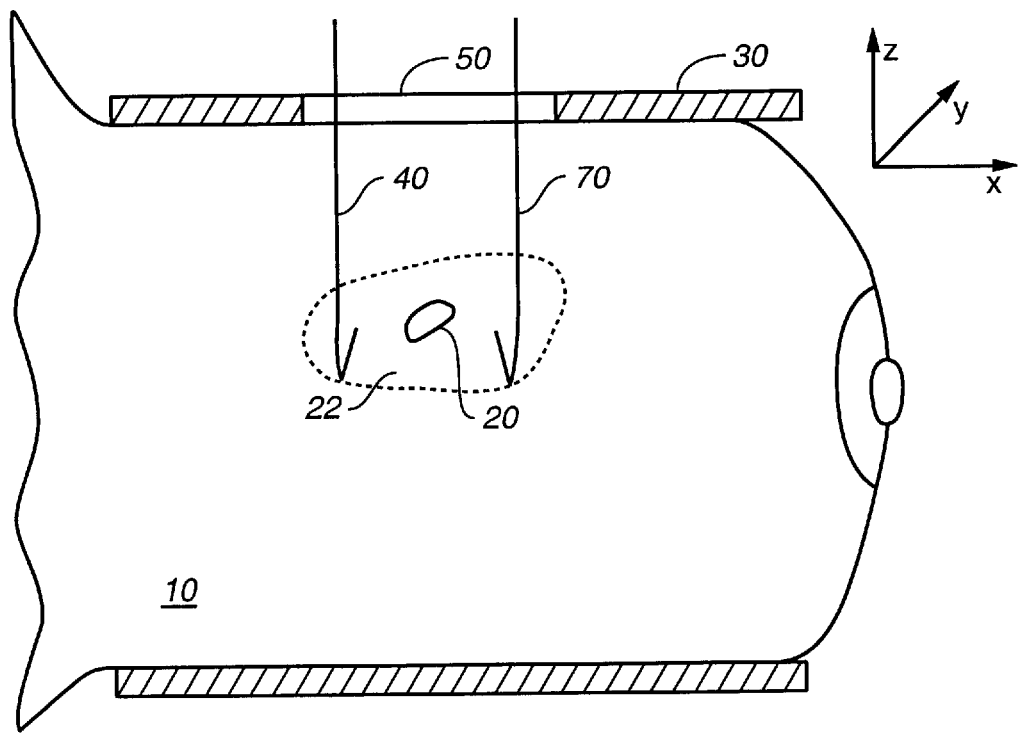
FIG._1B (PRIOR ART)

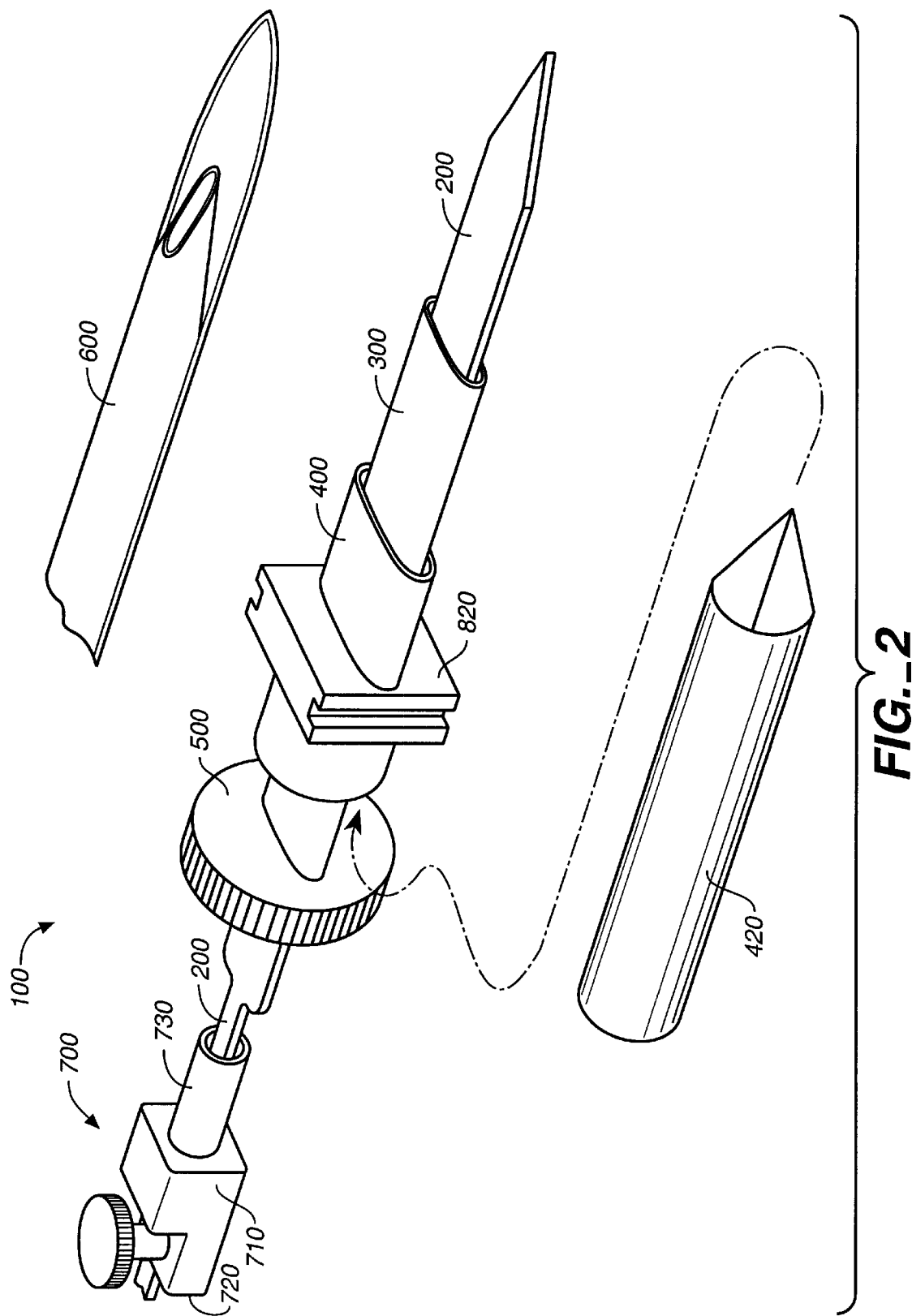
FIG._2

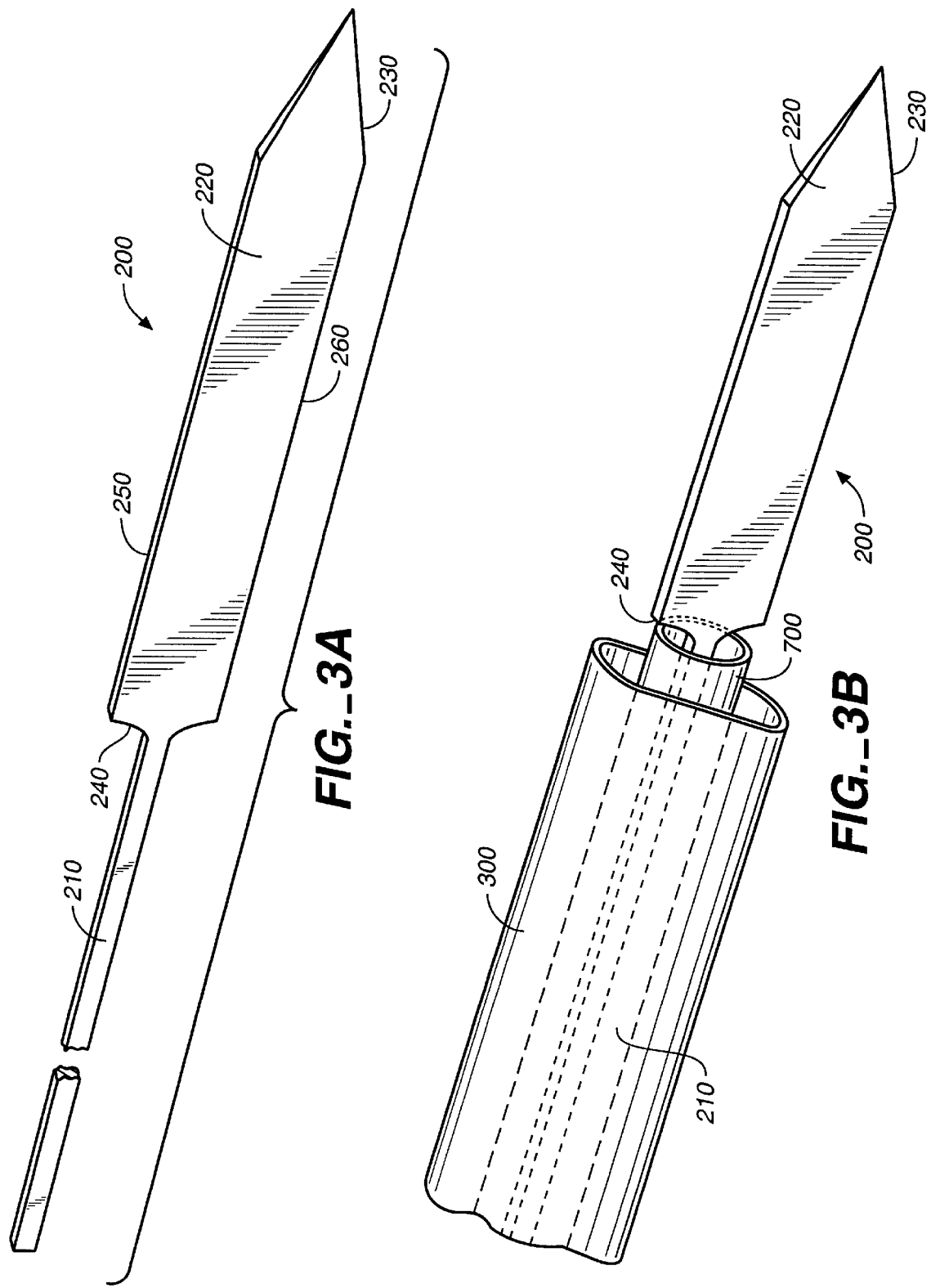
FIG._3A
FIG._3B

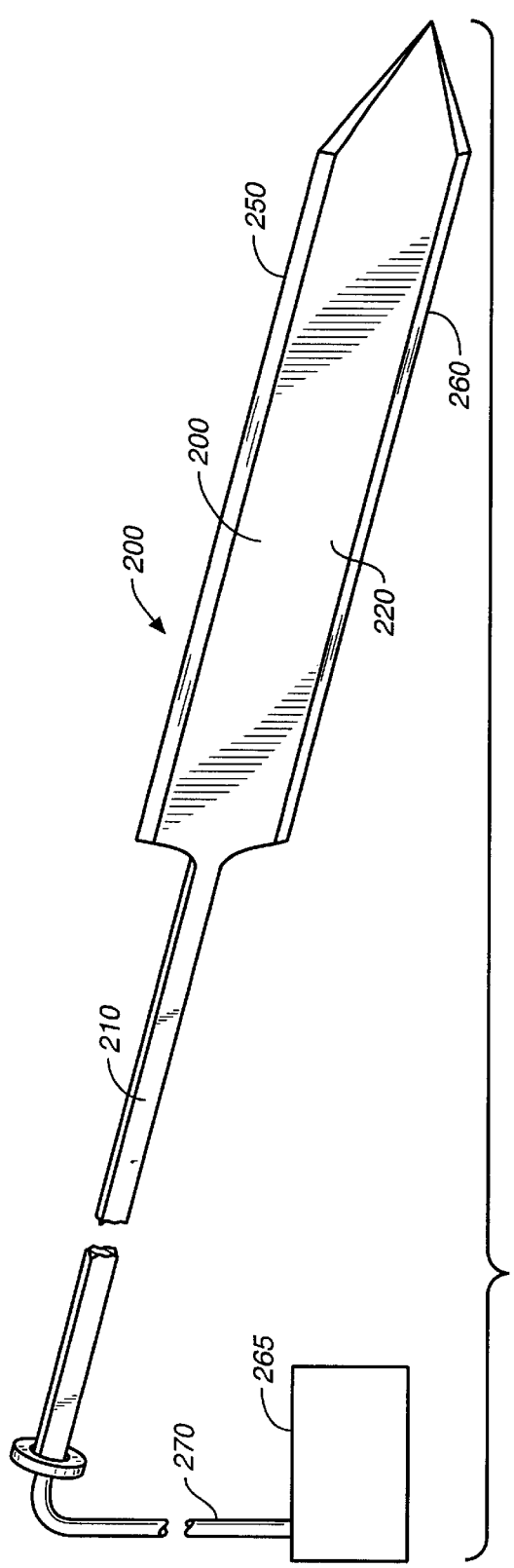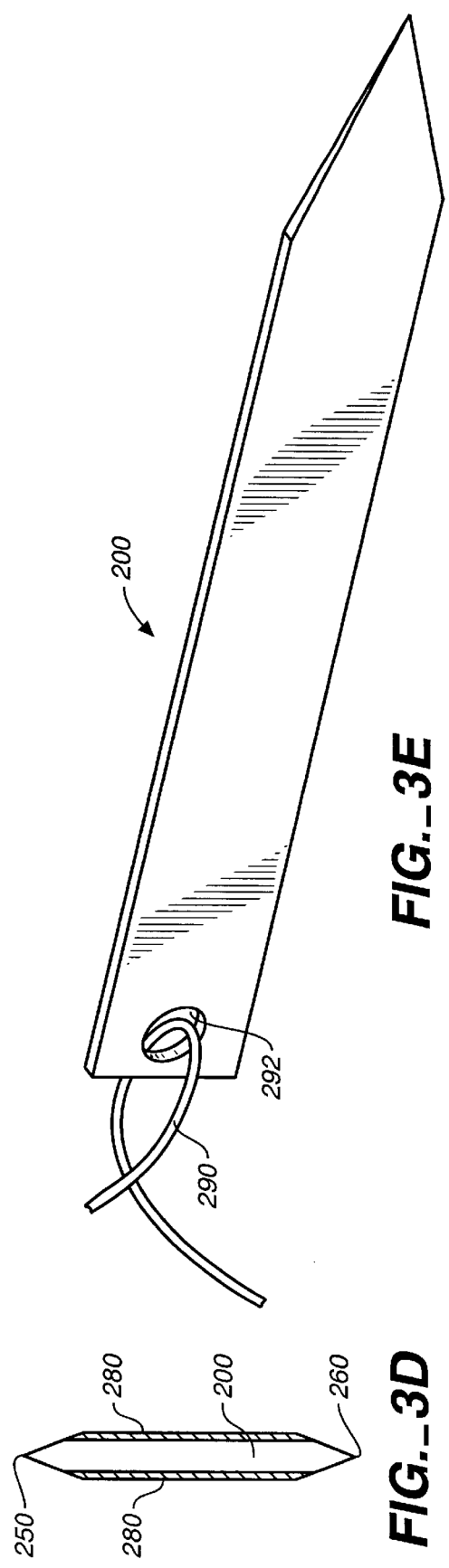

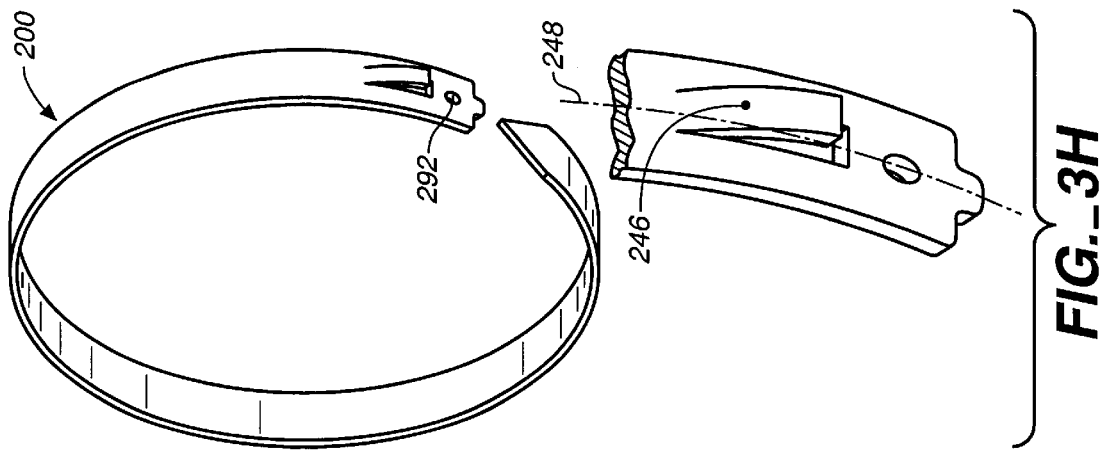
FIG._3H
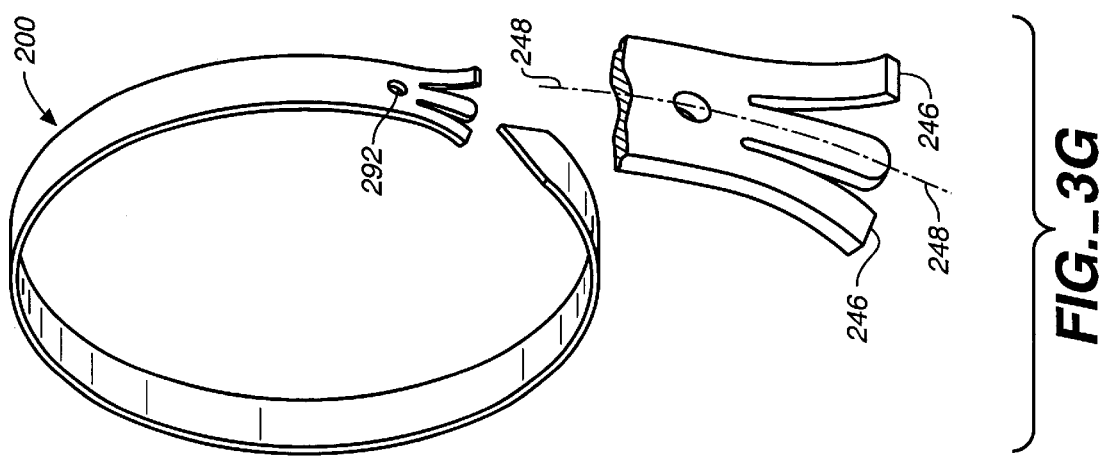
FIG._3G
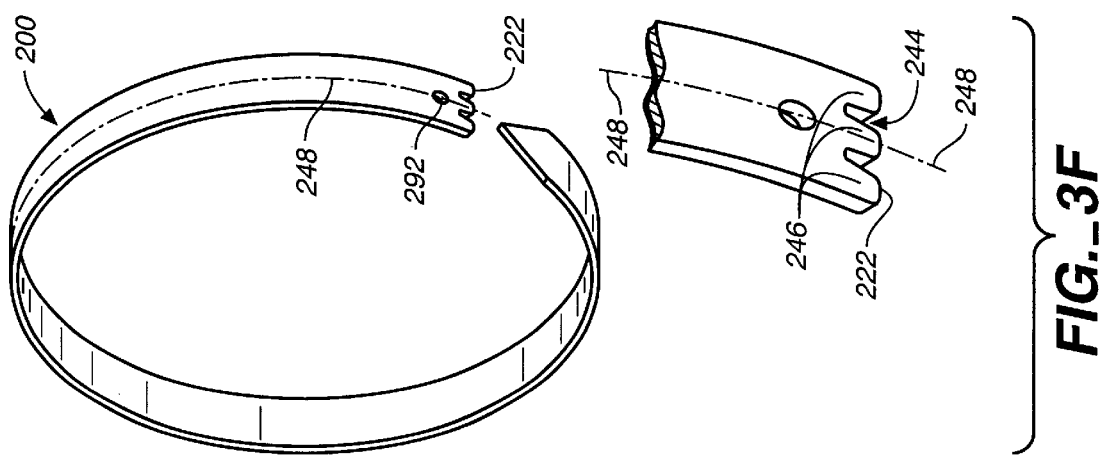
FIG._3F

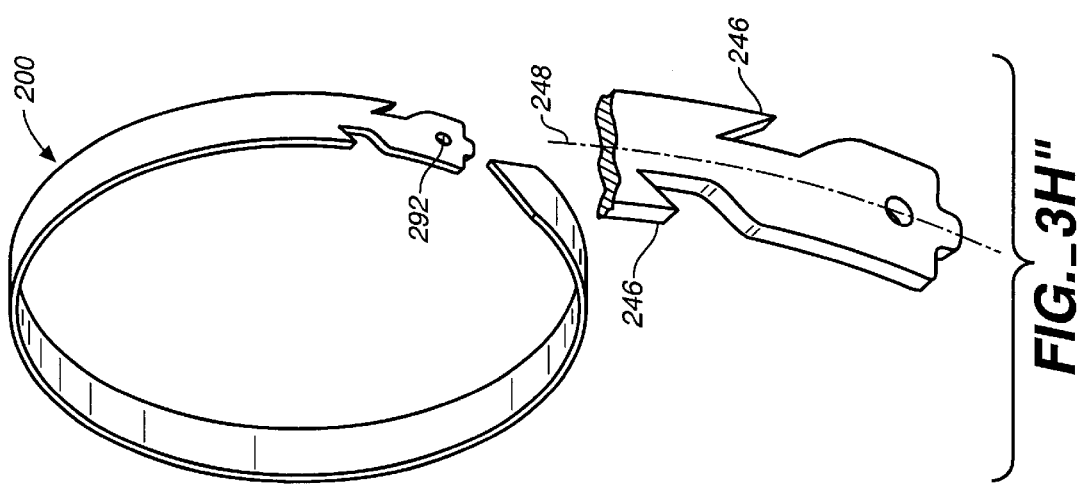
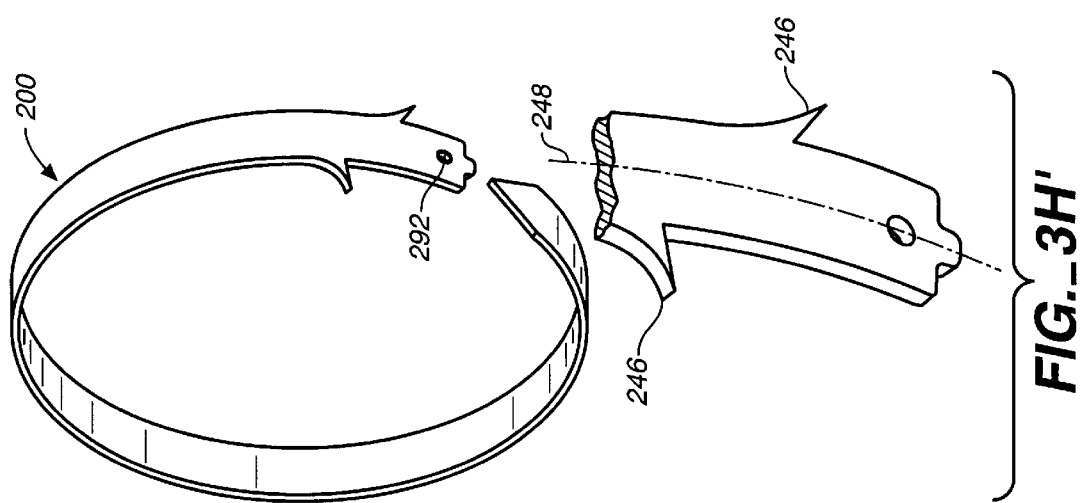

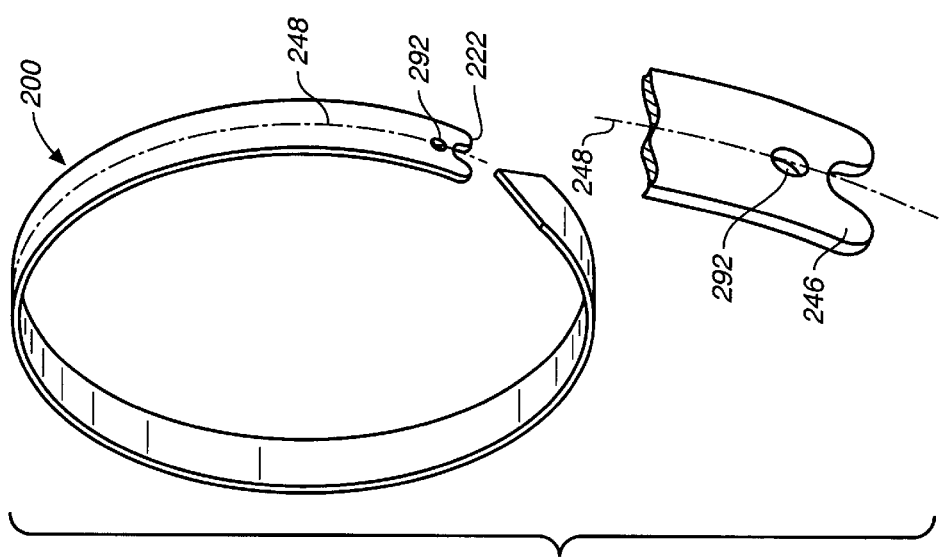
FIG._3I
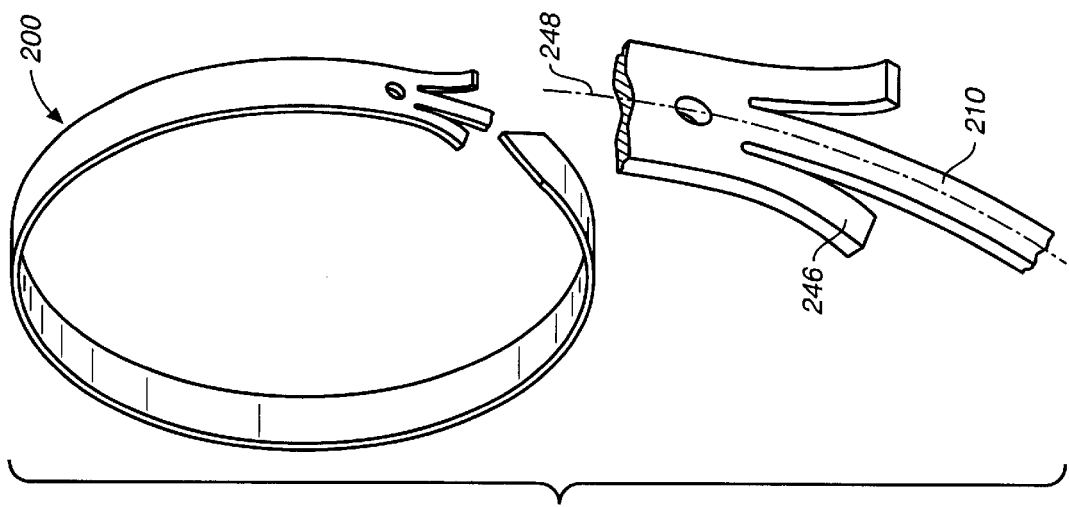
FIG._3J

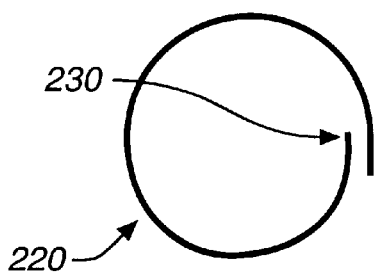
FIG._3K
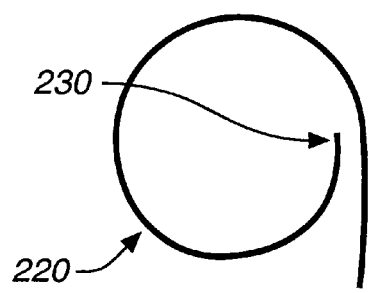
FIG._3L
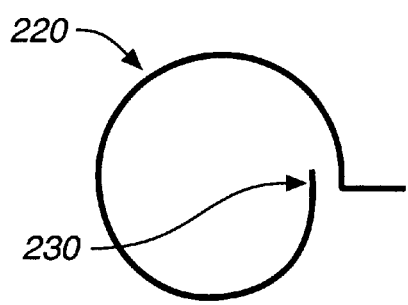
FIG._3M
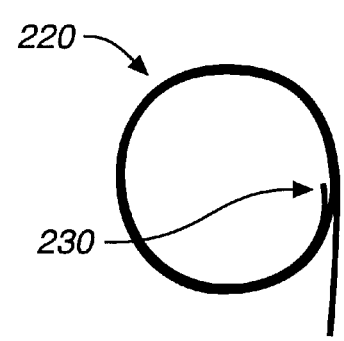
FIG._3N
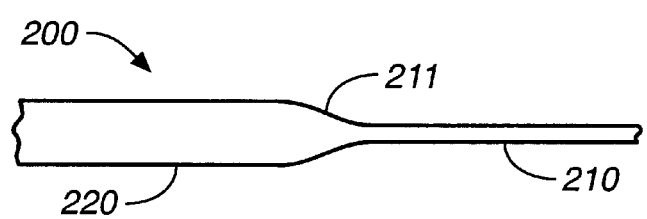
FIG._3O
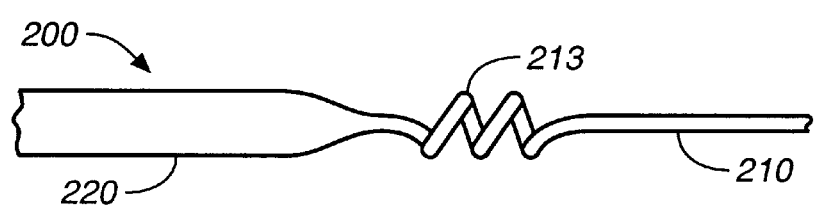
FIG._3P

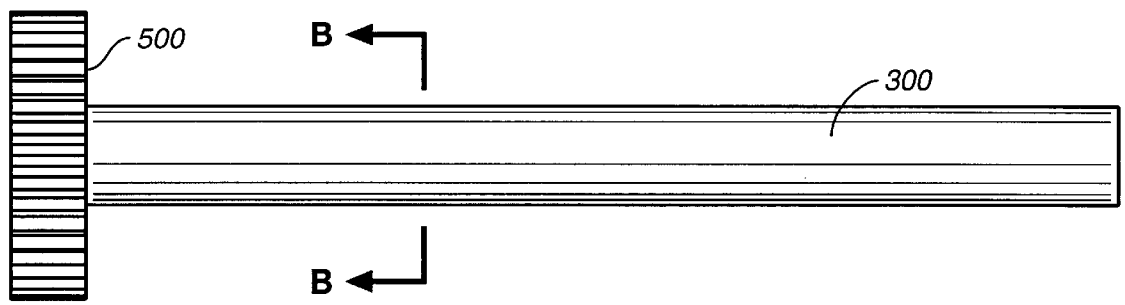
FIG._4A
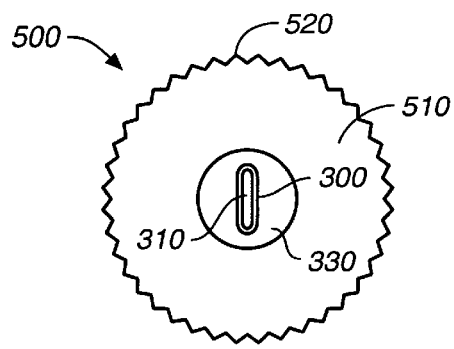
FIG._4B
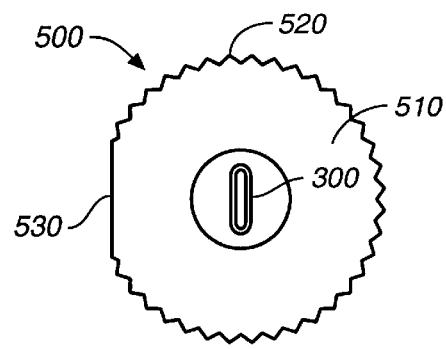
FIG._4C
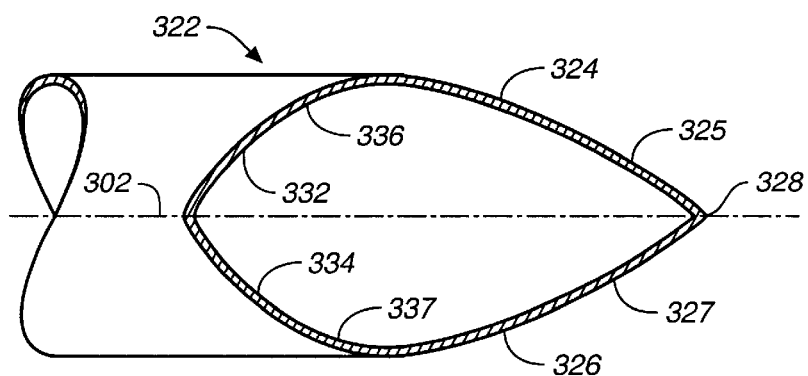
FIG._4D

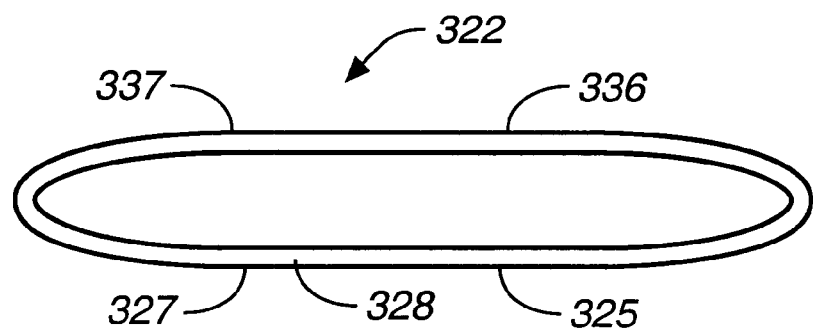
FIG._4E
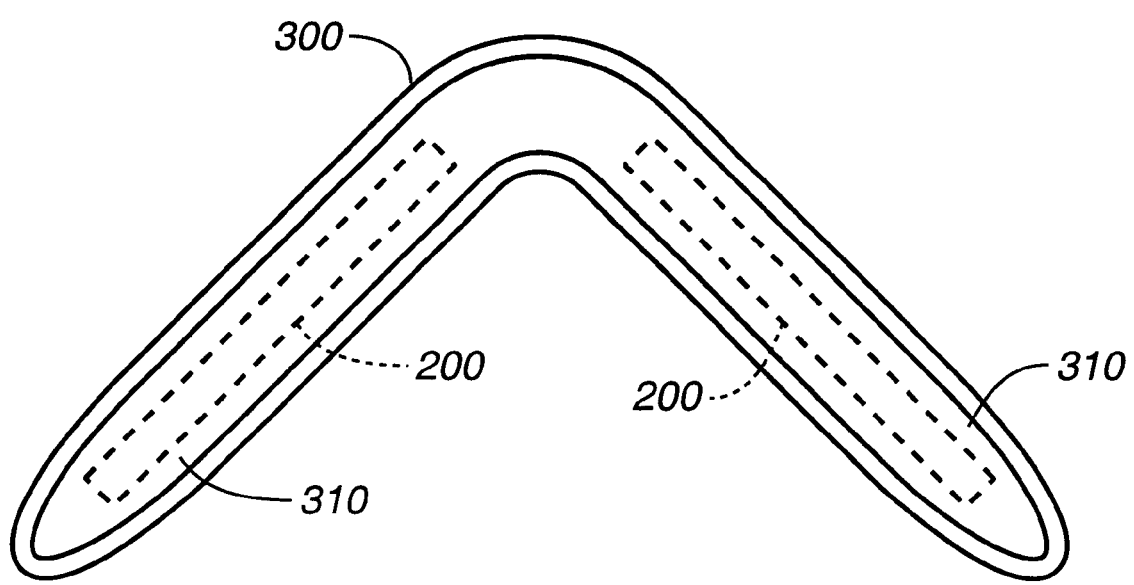
FIG._4F

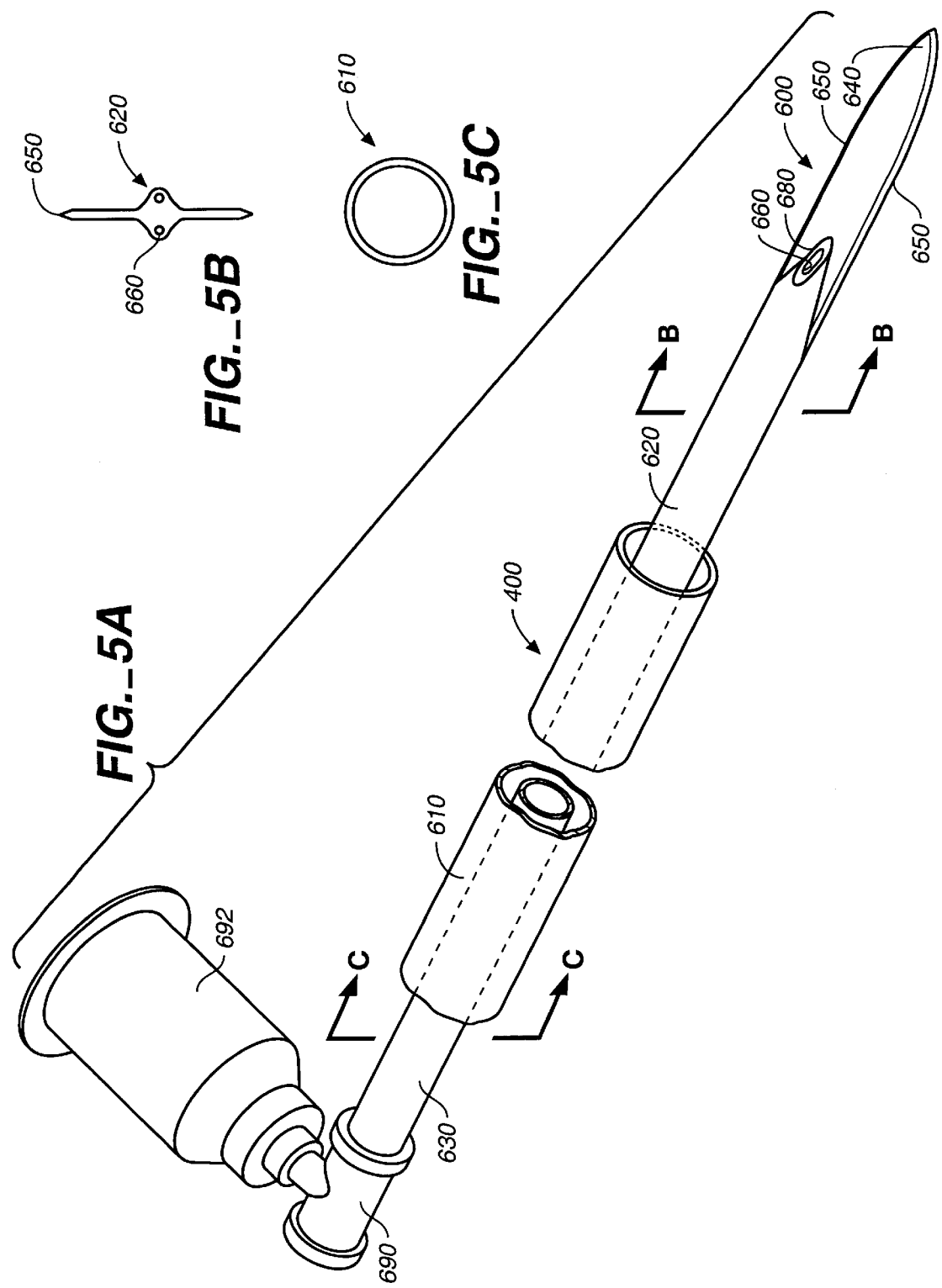

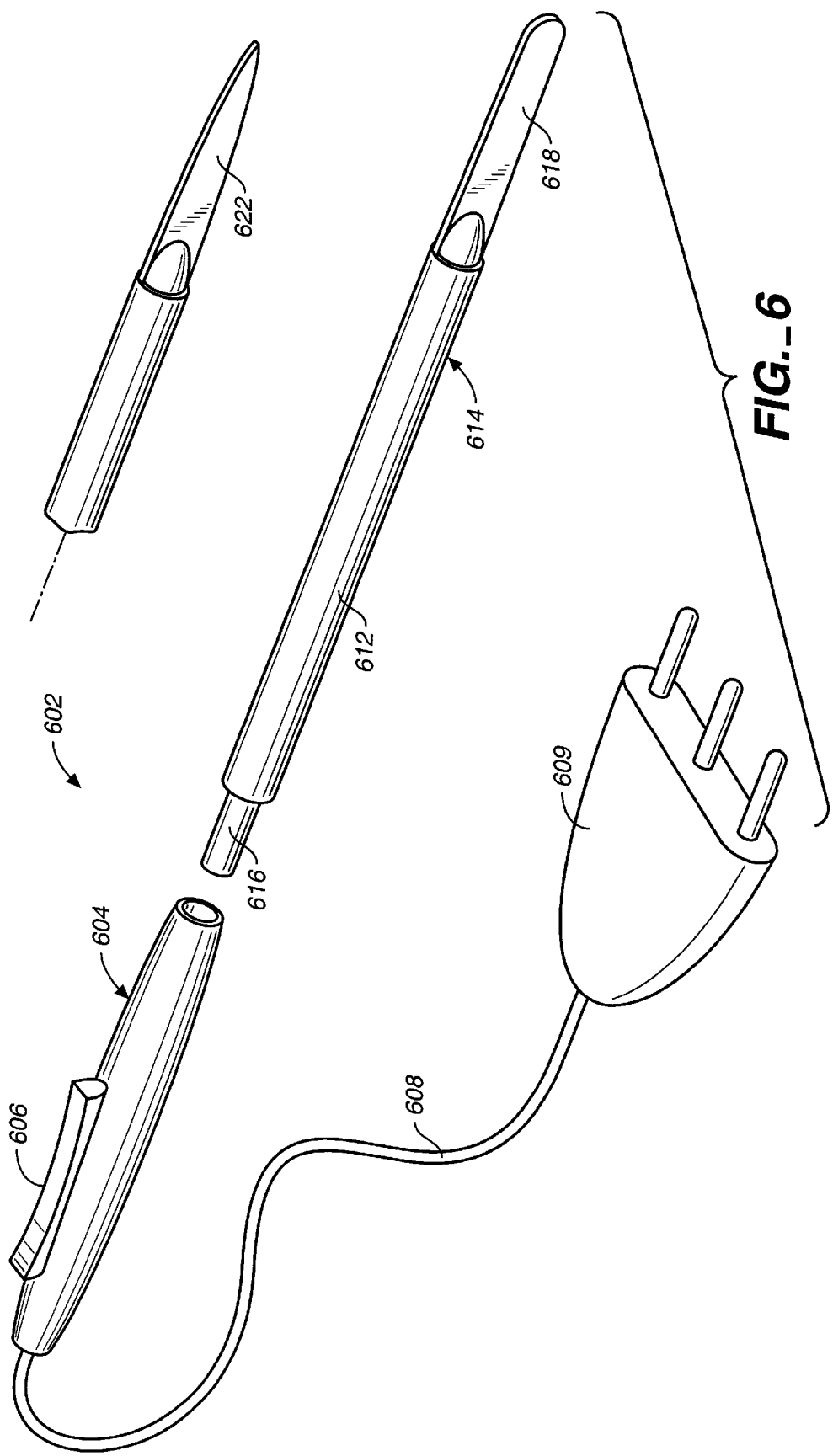
FIG._6

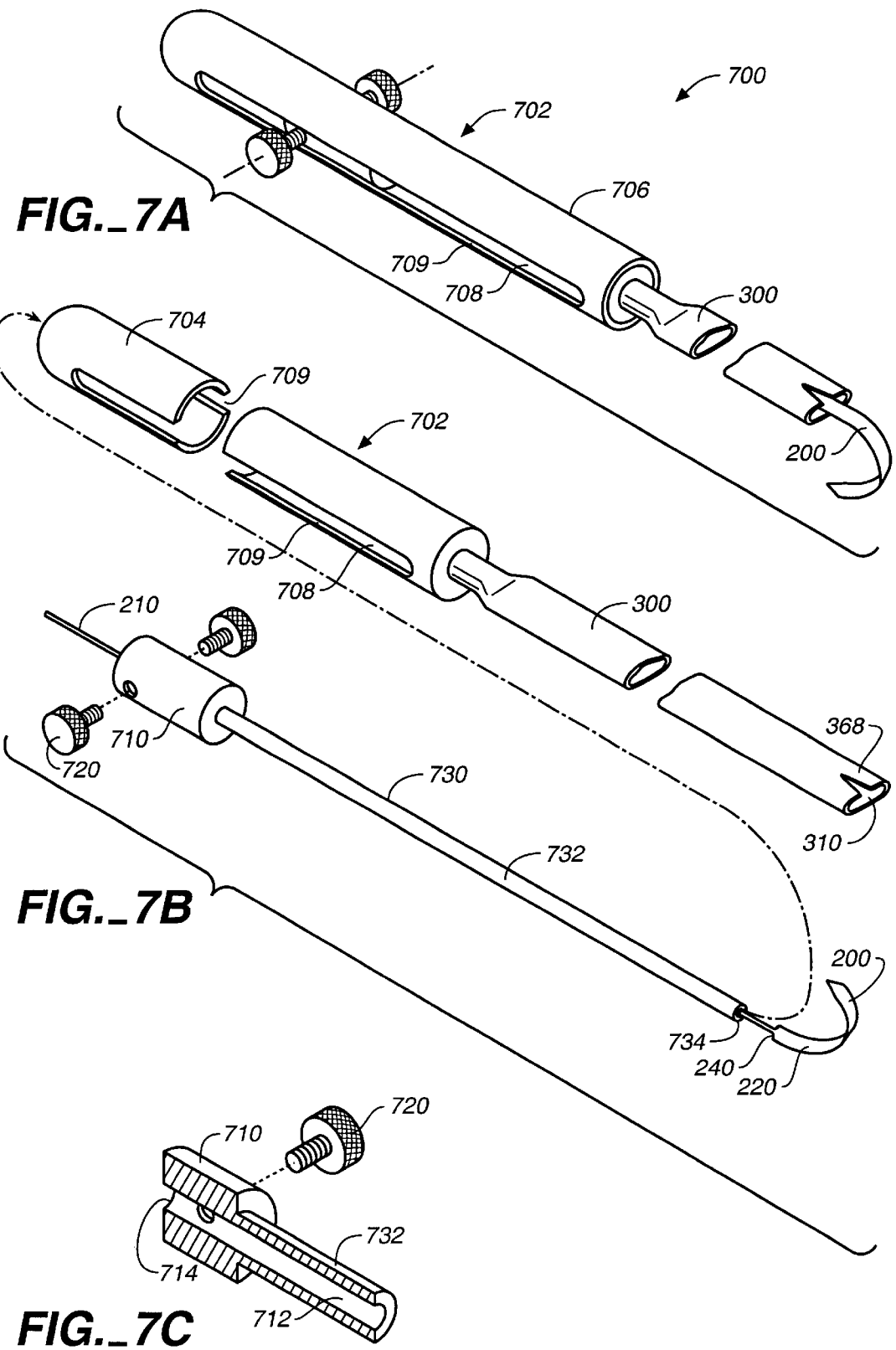

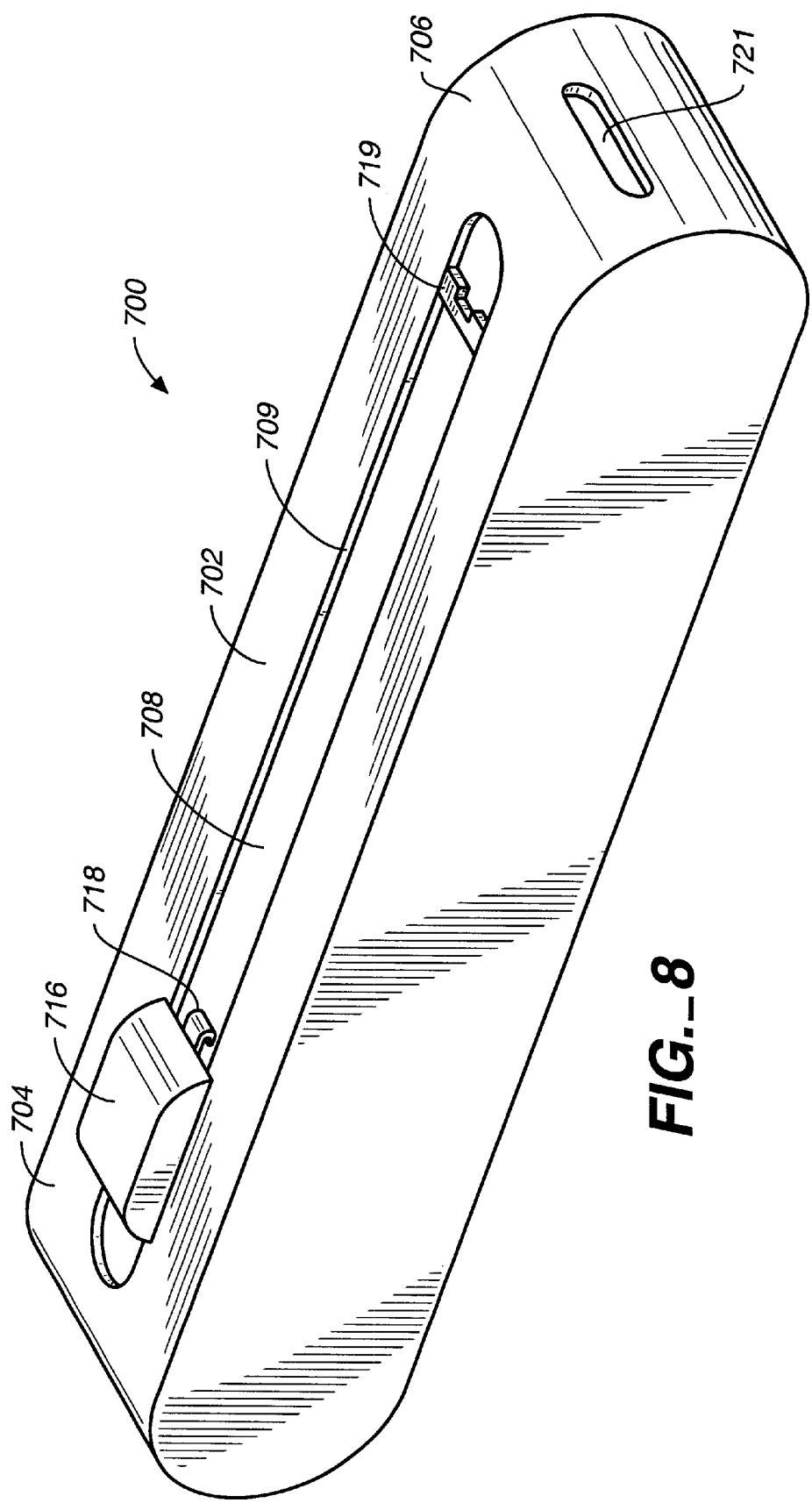
FIG._8

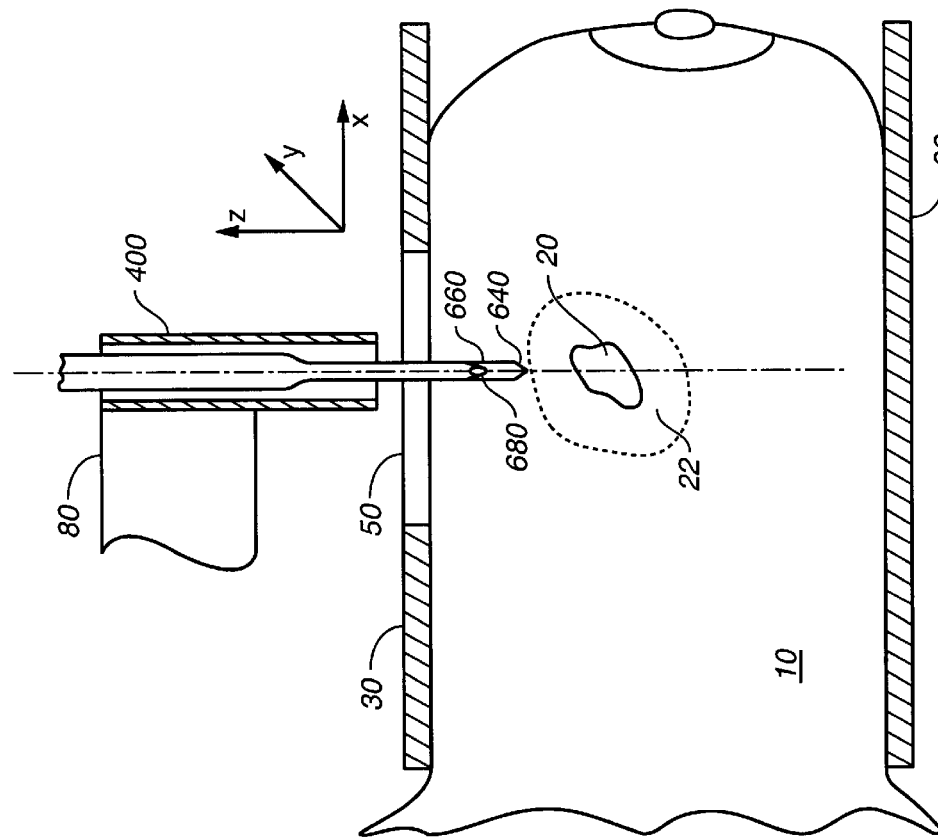
FIG._10
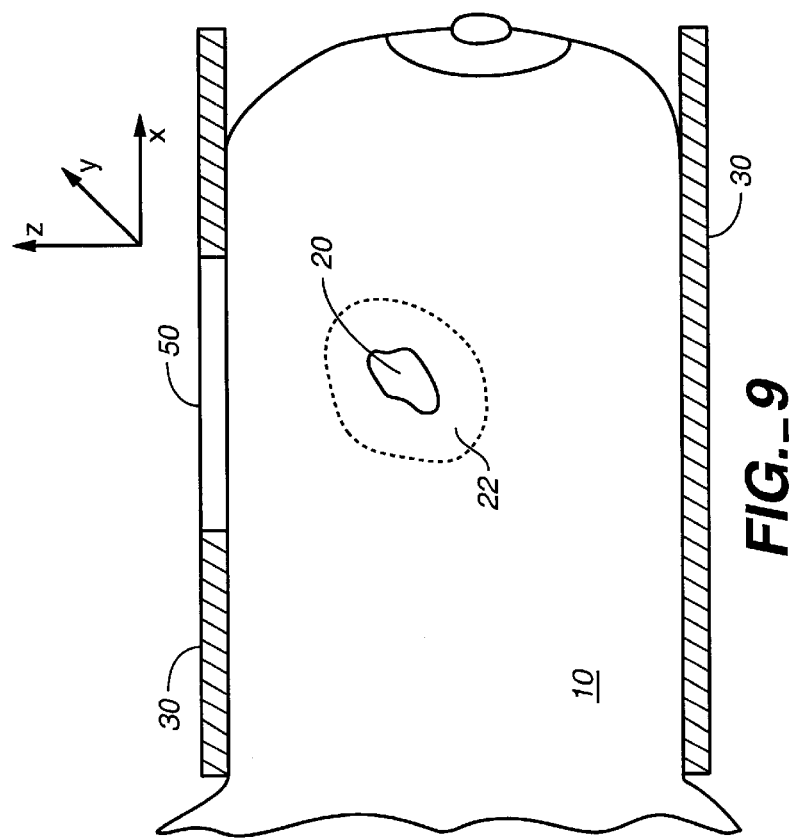
FIG._9

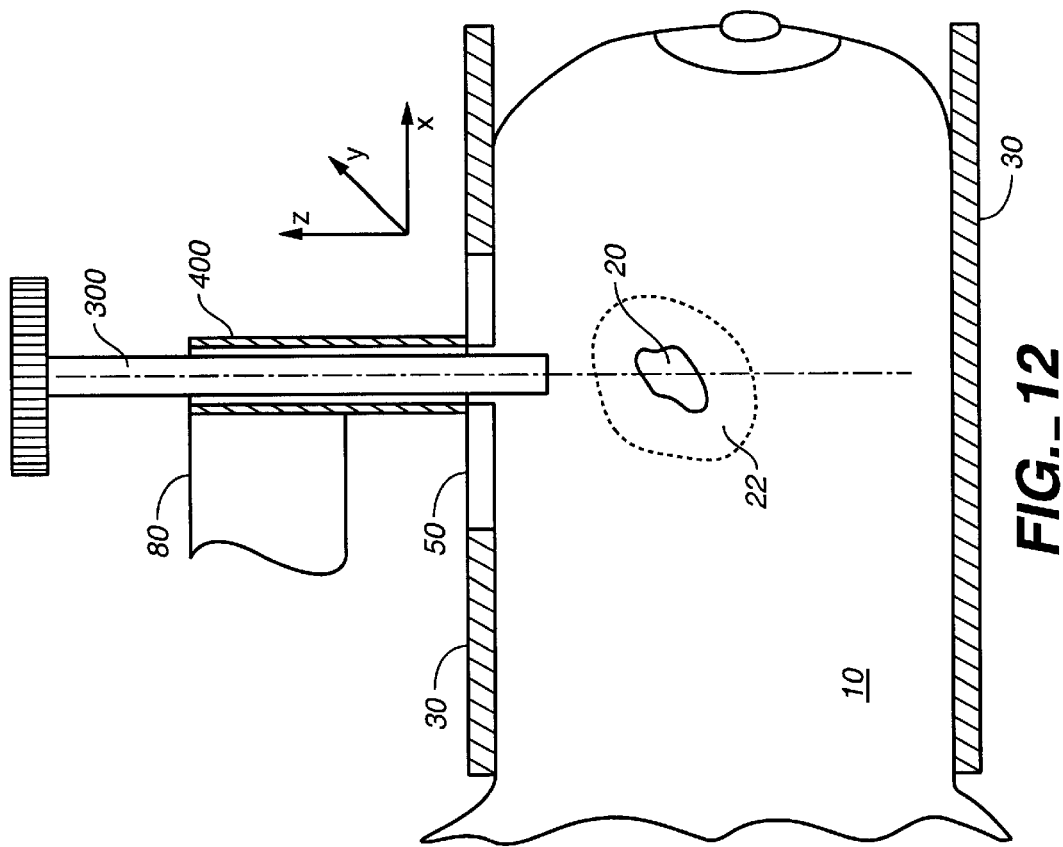
FIG._12
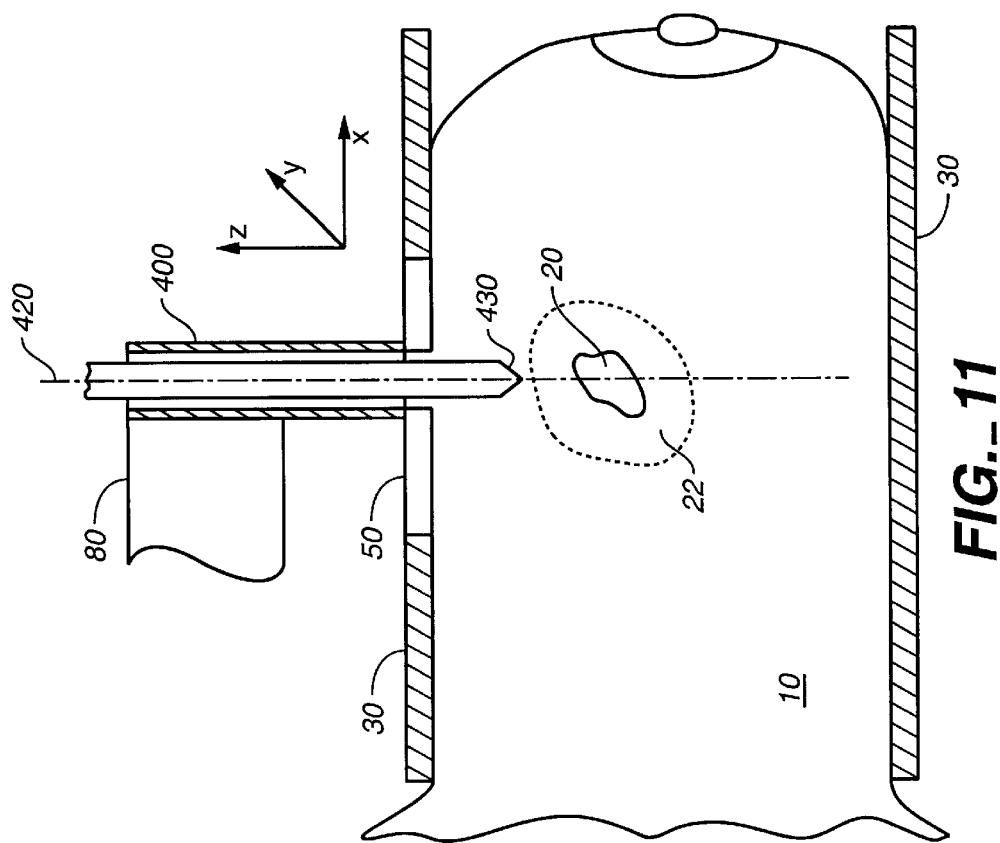
FIG._11

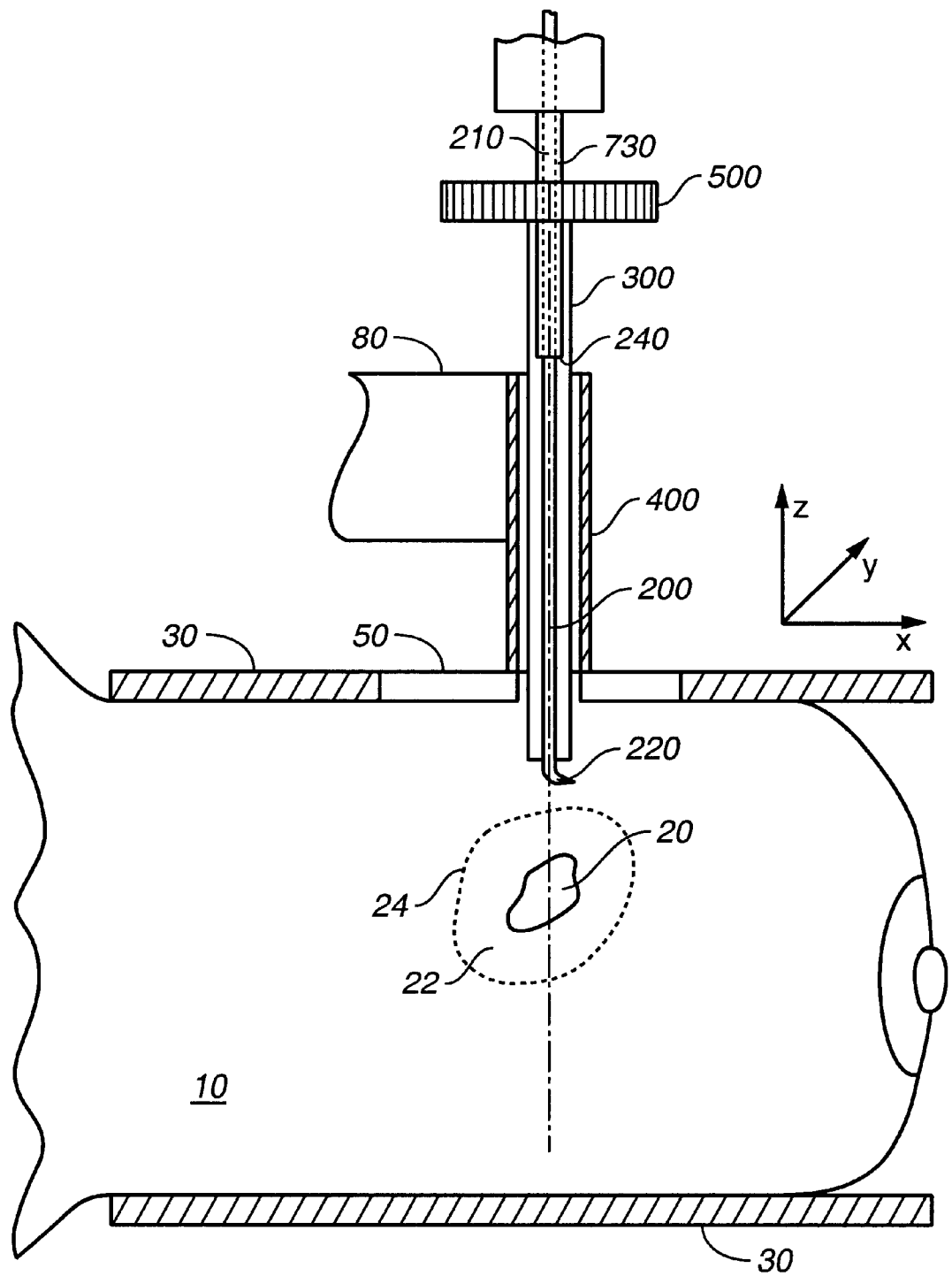
FIG._13

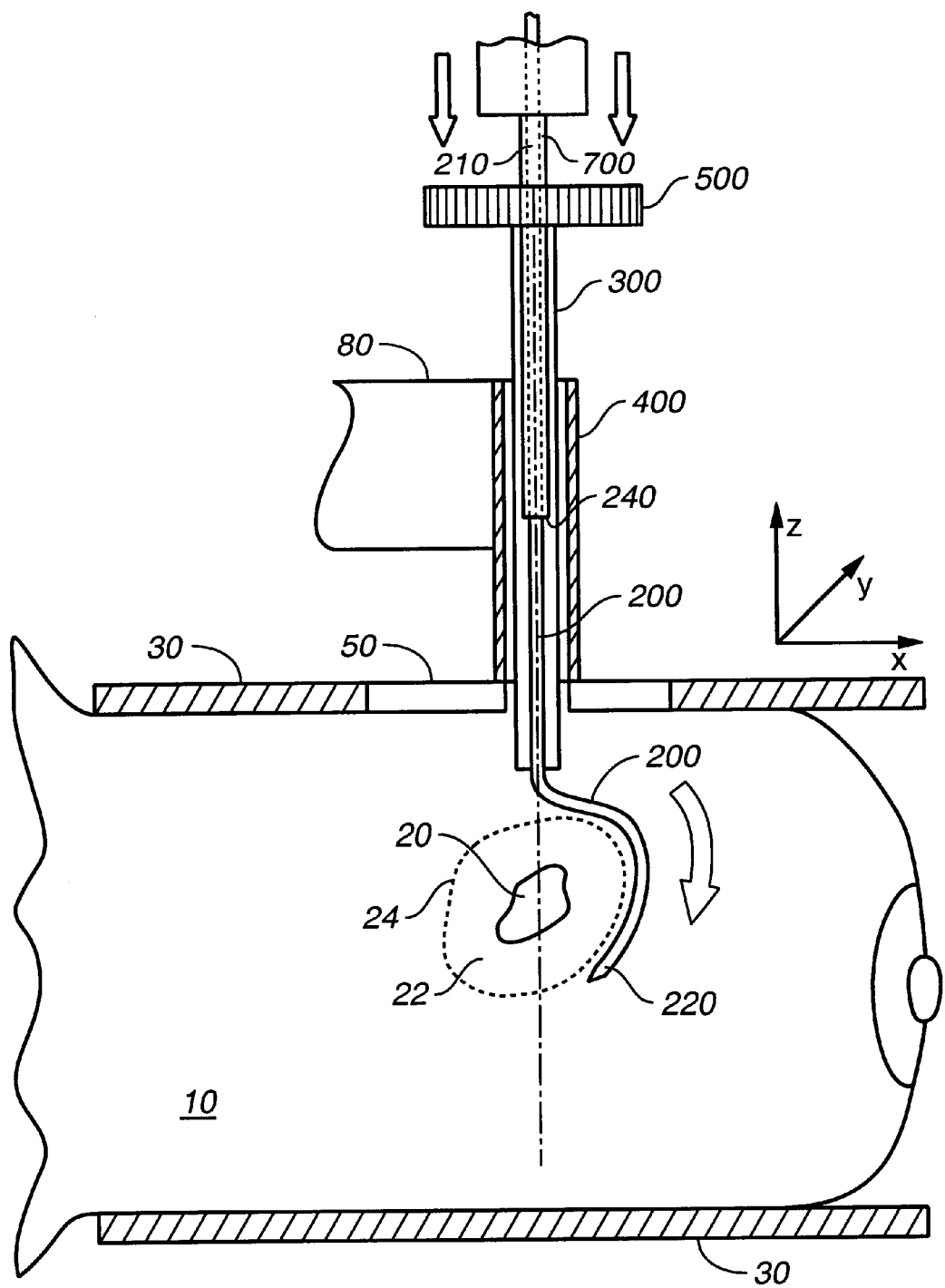
FIG._14

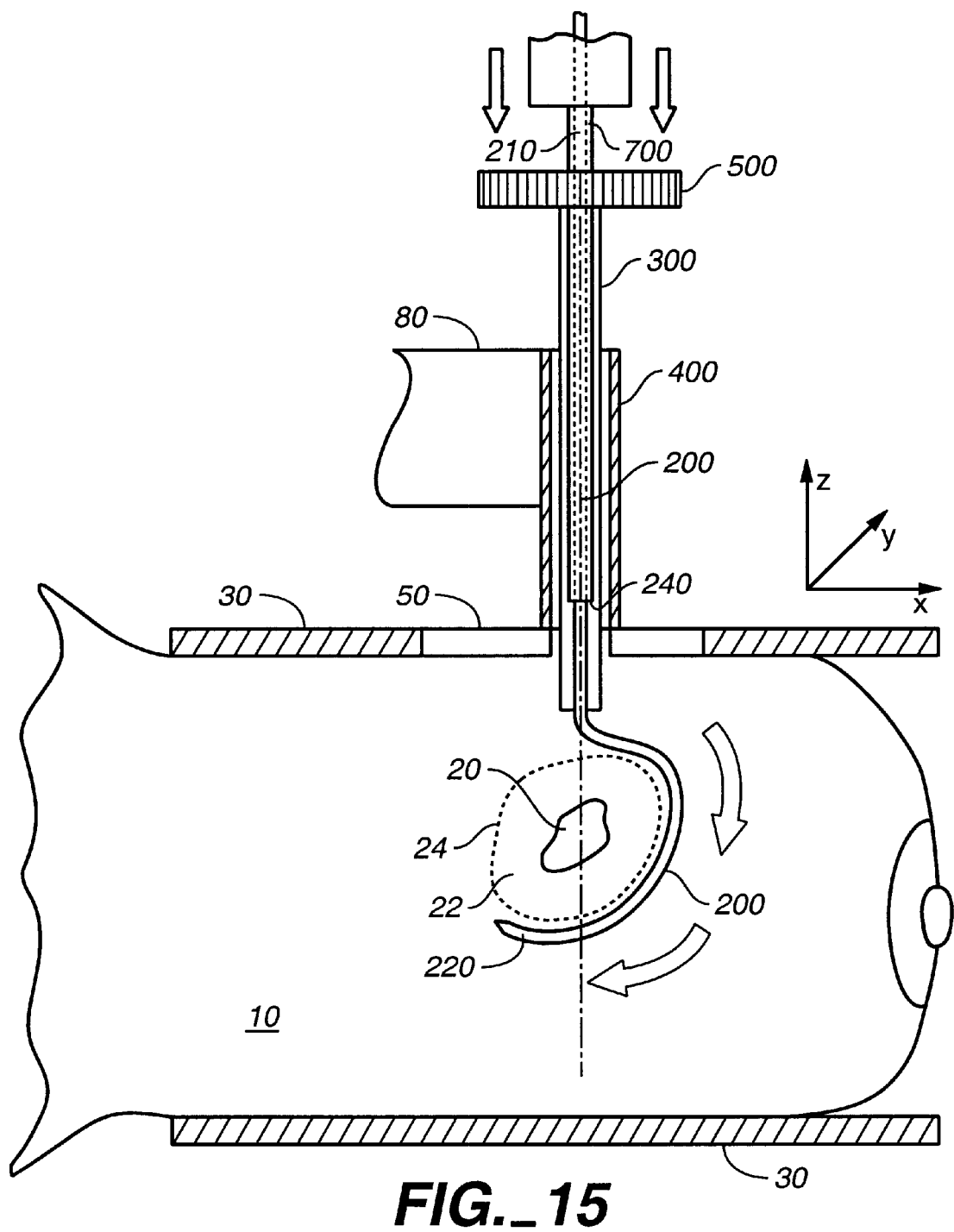
FIG._15

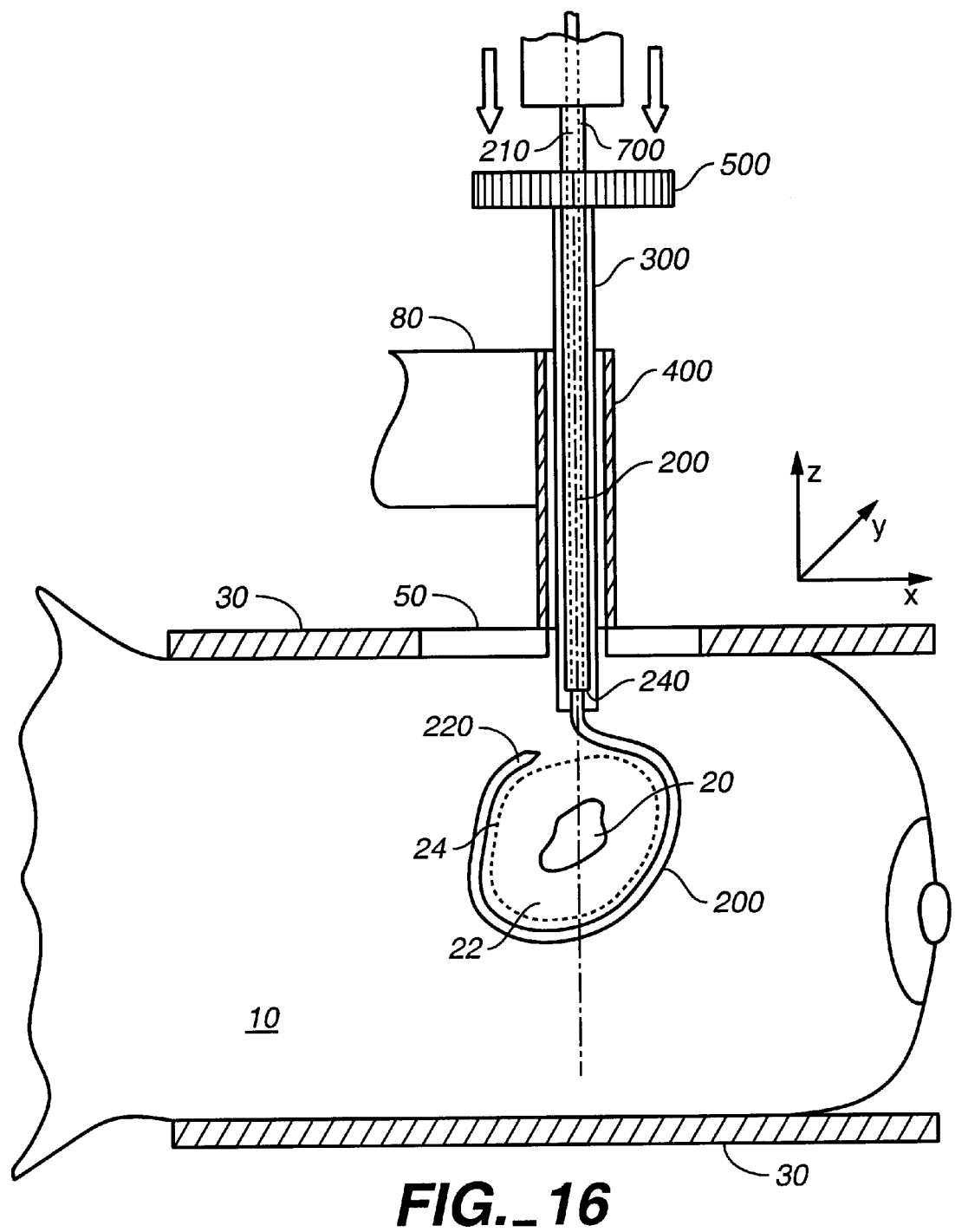
FIG._16

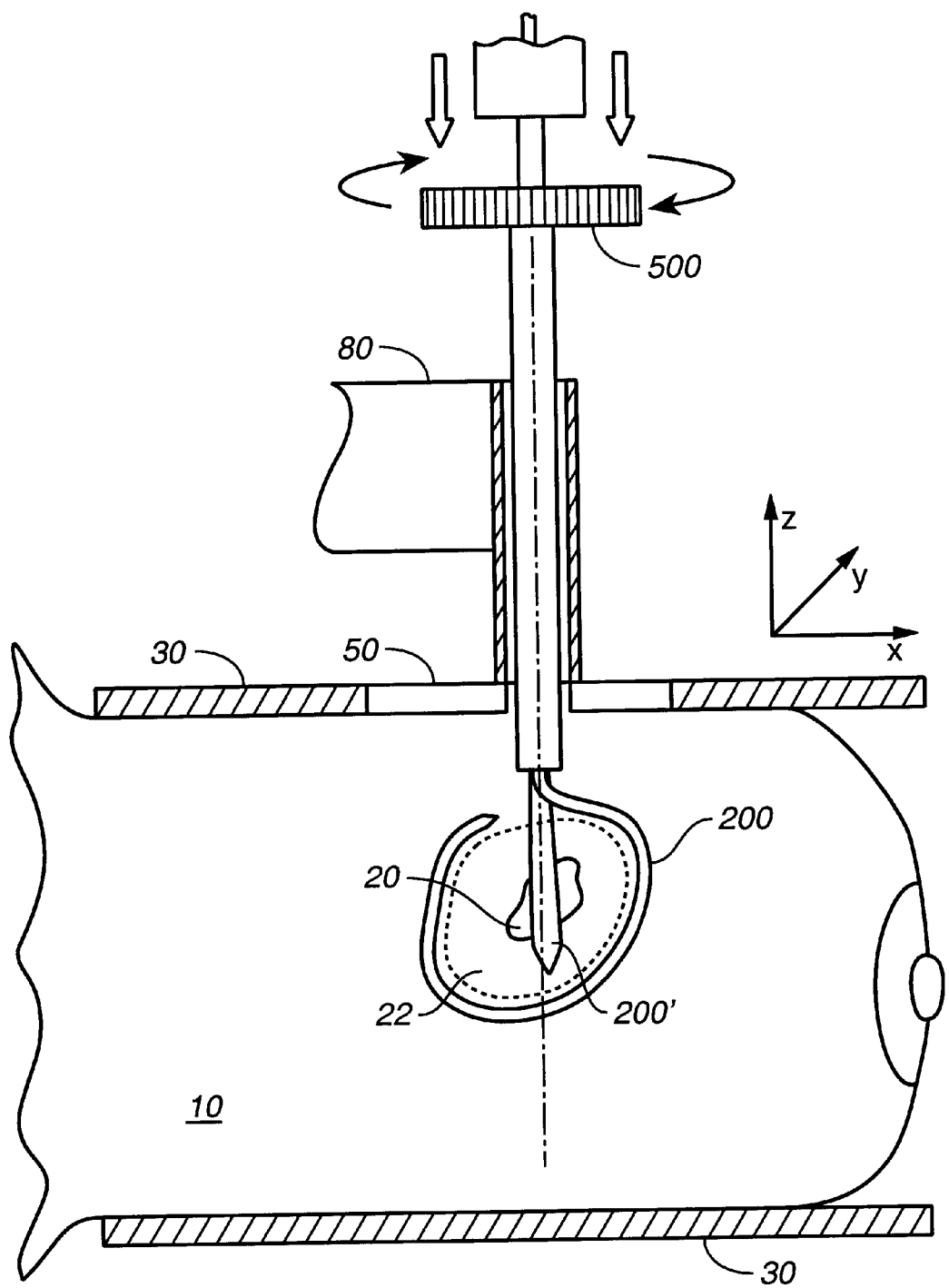
FIG._17

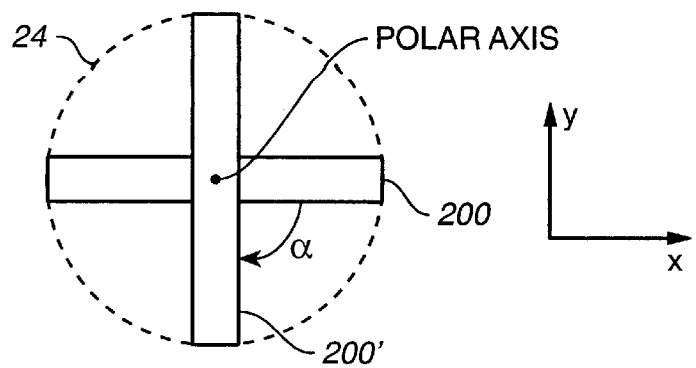
FIG._18
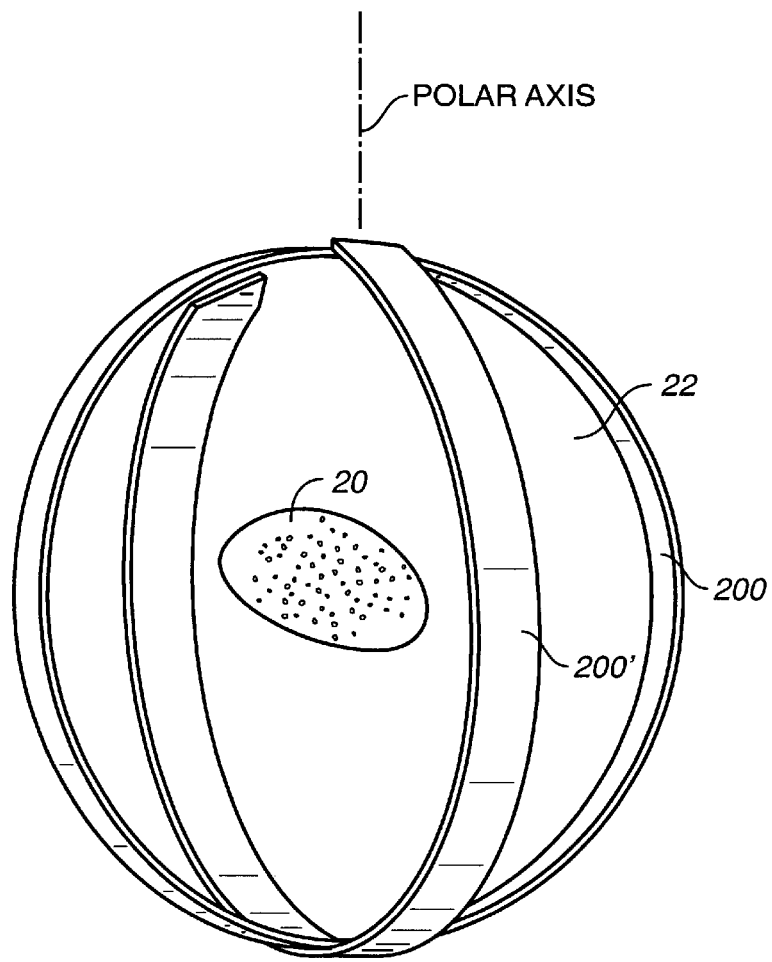
FIG._19

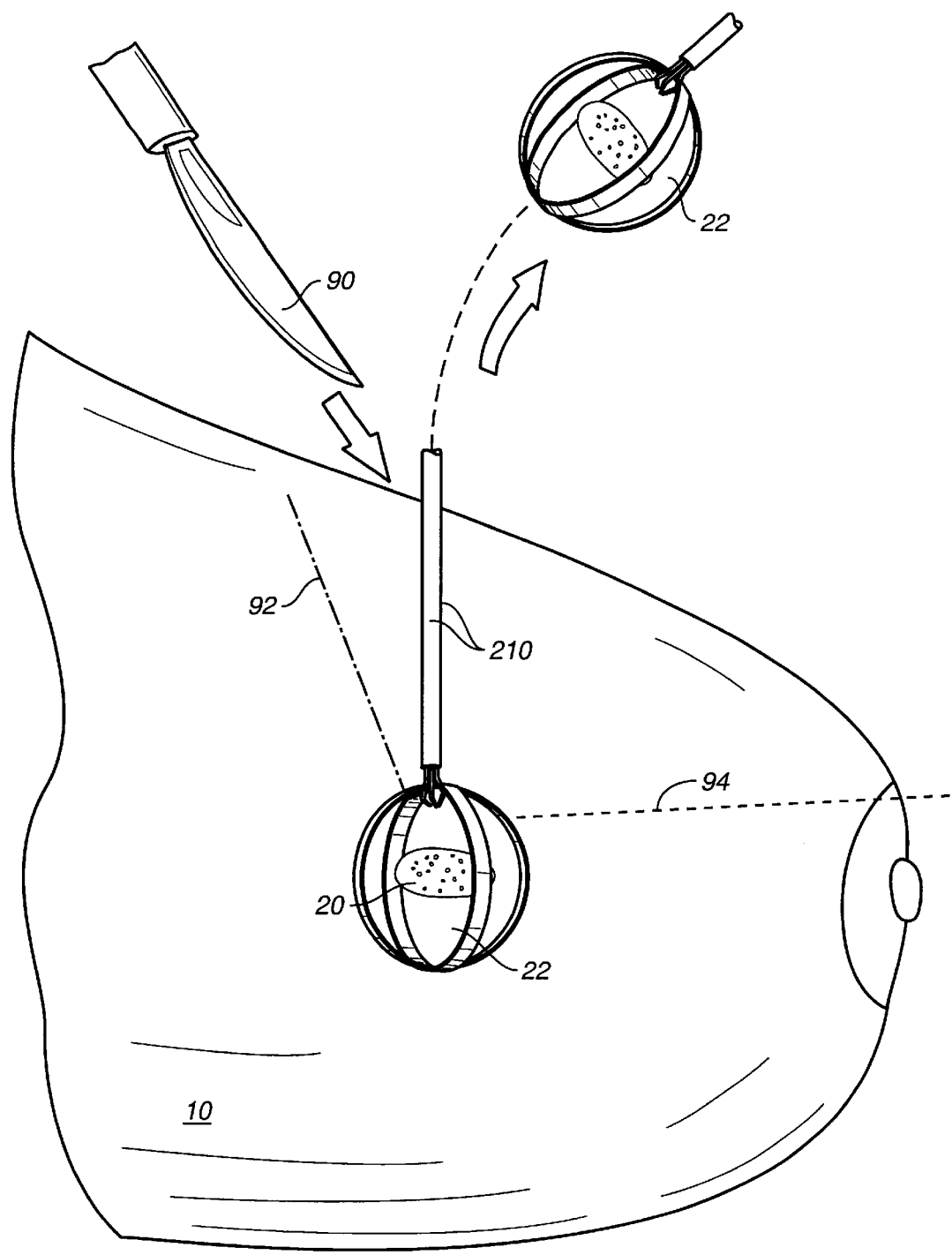
FIG._20A

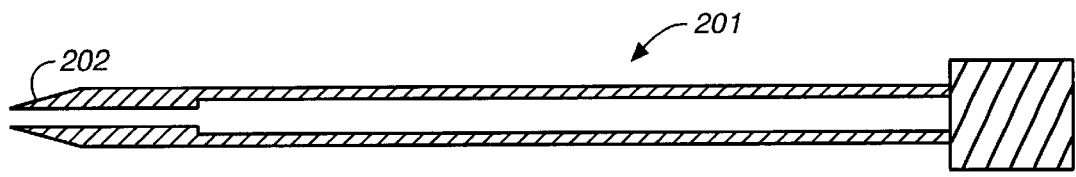
FIG._20B
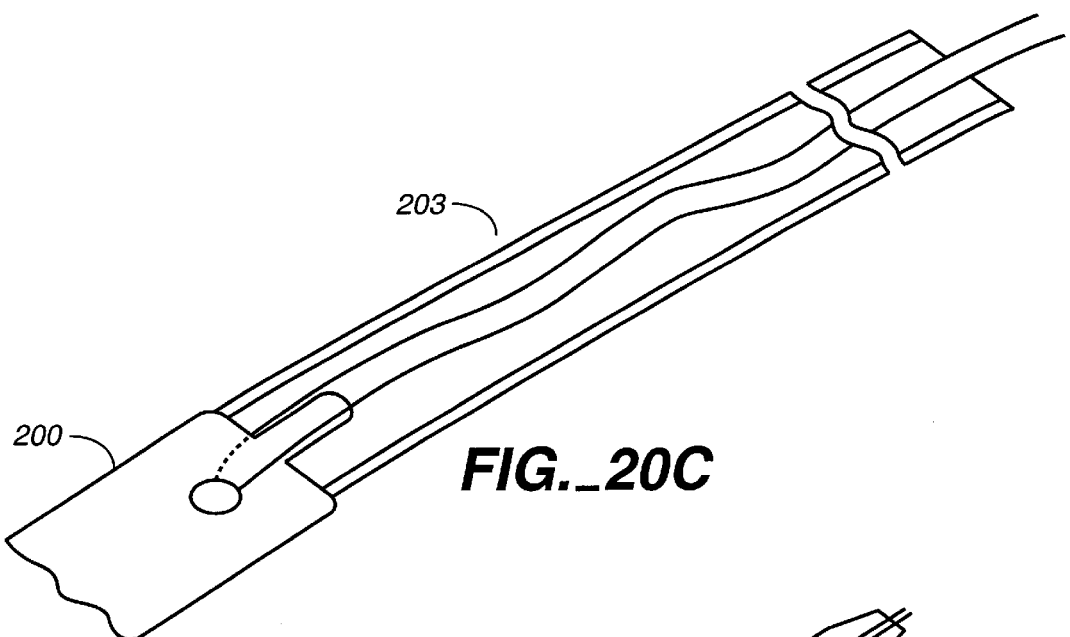
FIG._20C
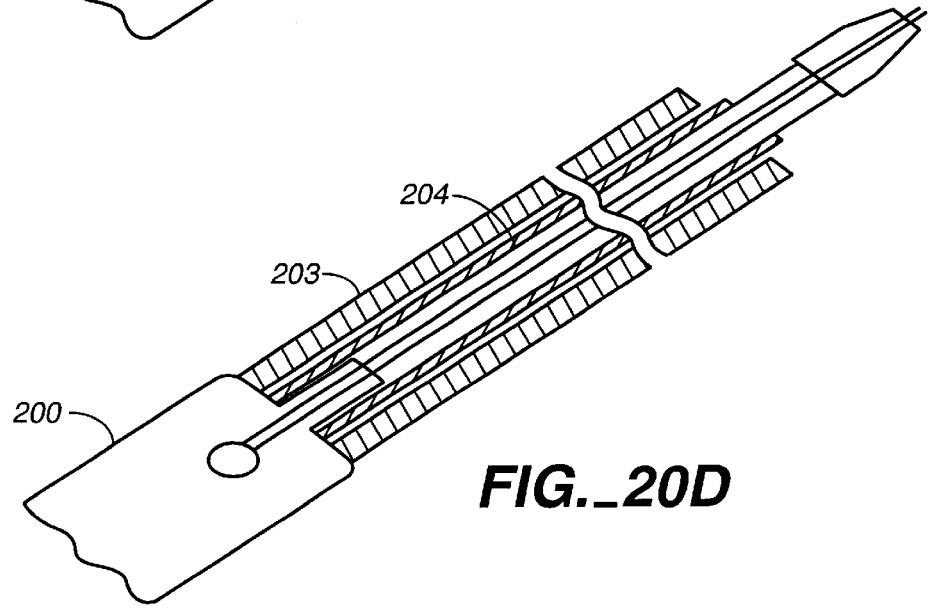
FIG._20D

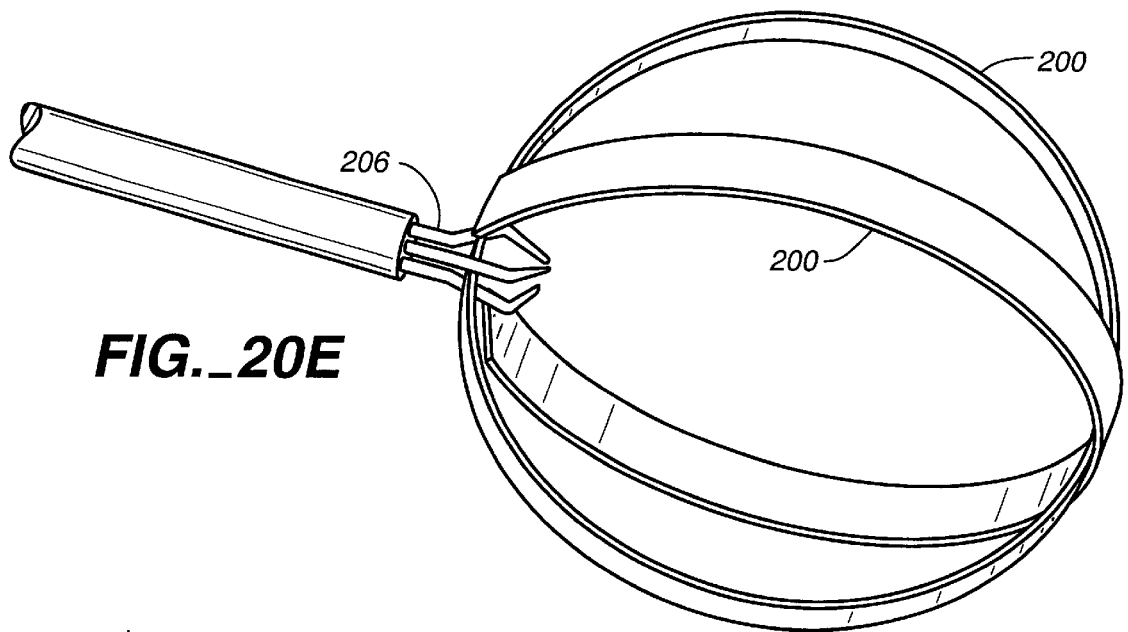
FIG._20E
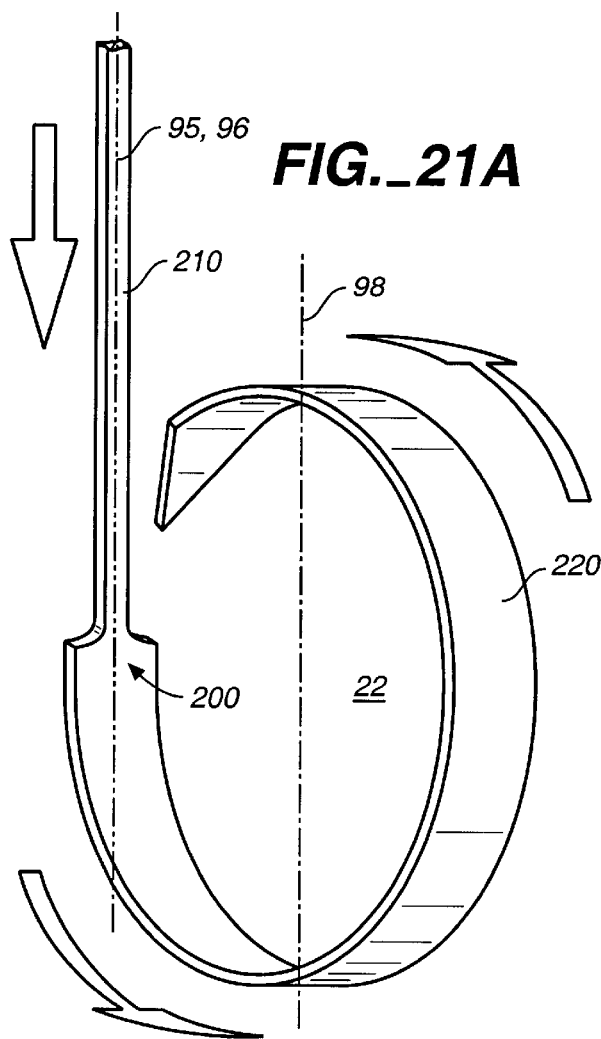
FIG._21A
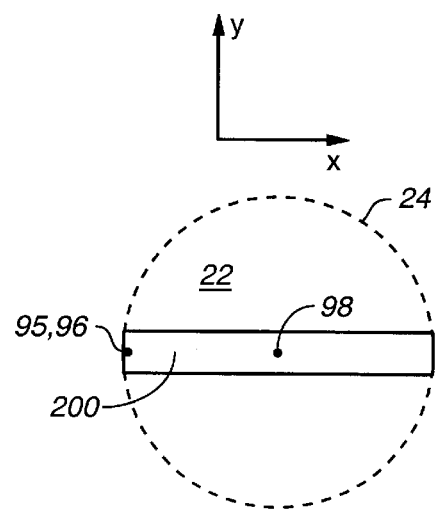
FIG._21B

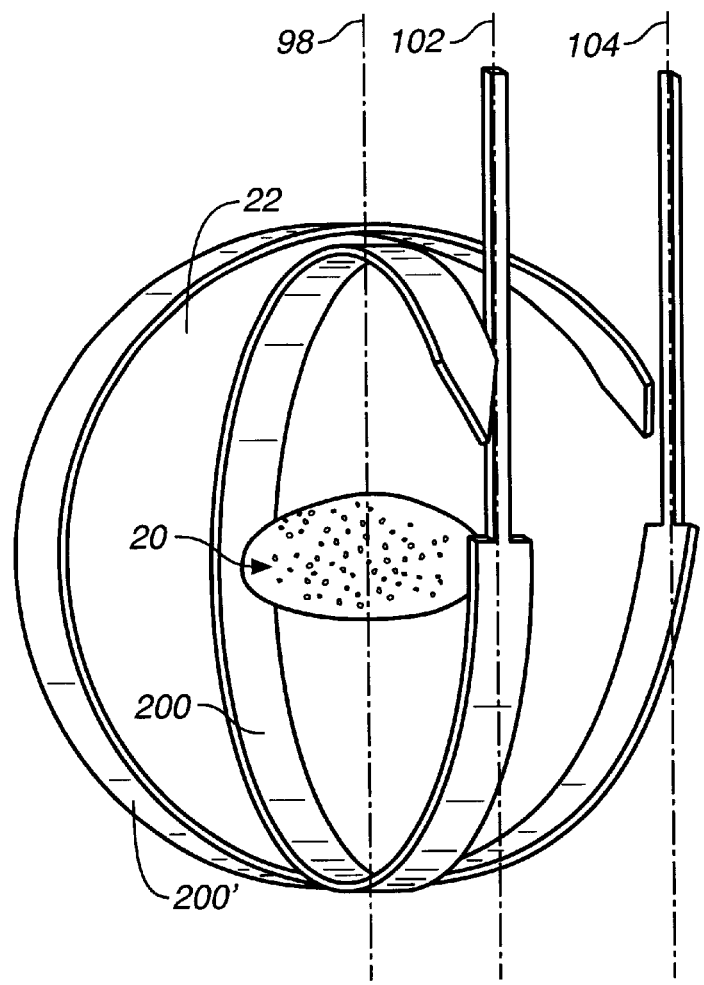
FIG._22A
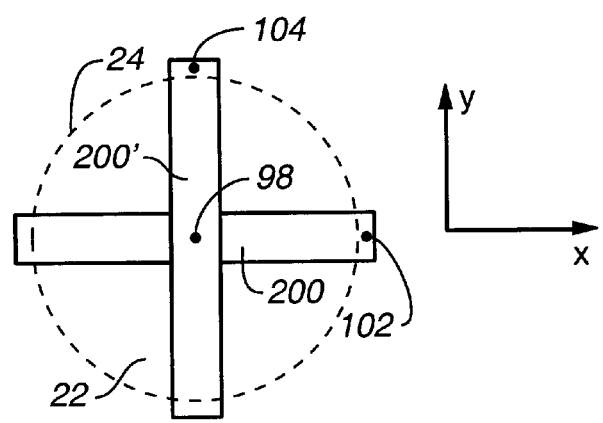
FIG._22B

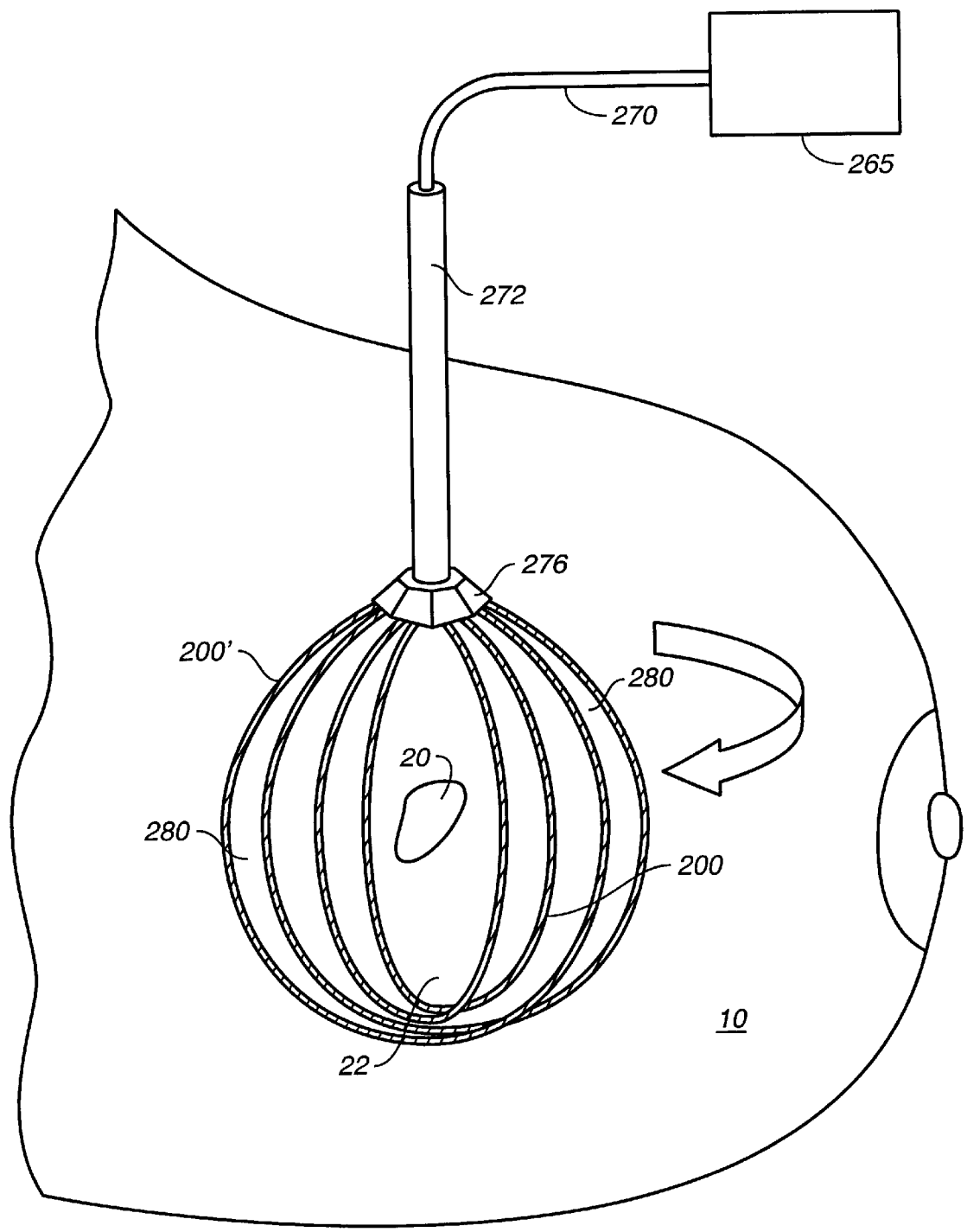
FIG._23

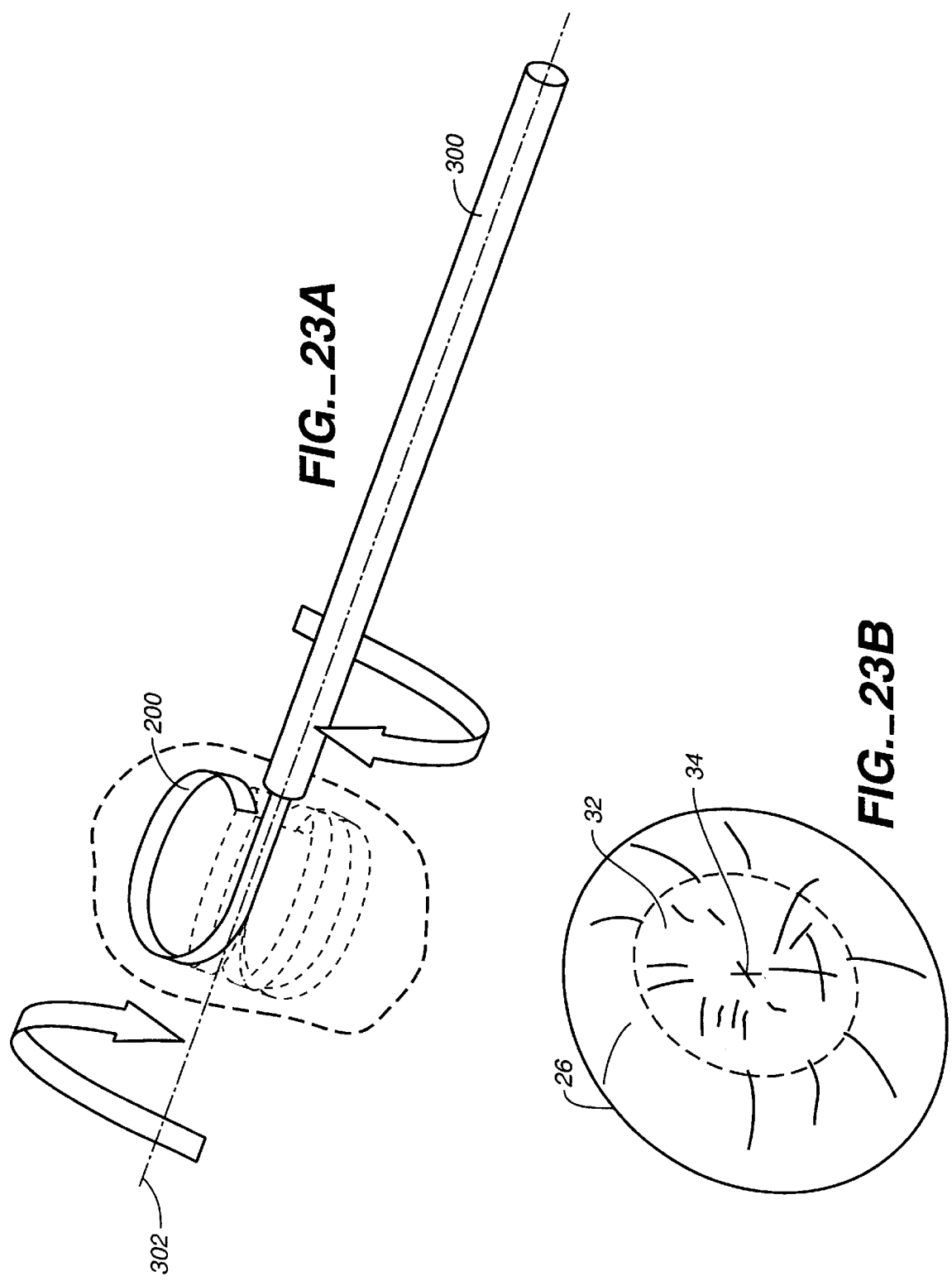

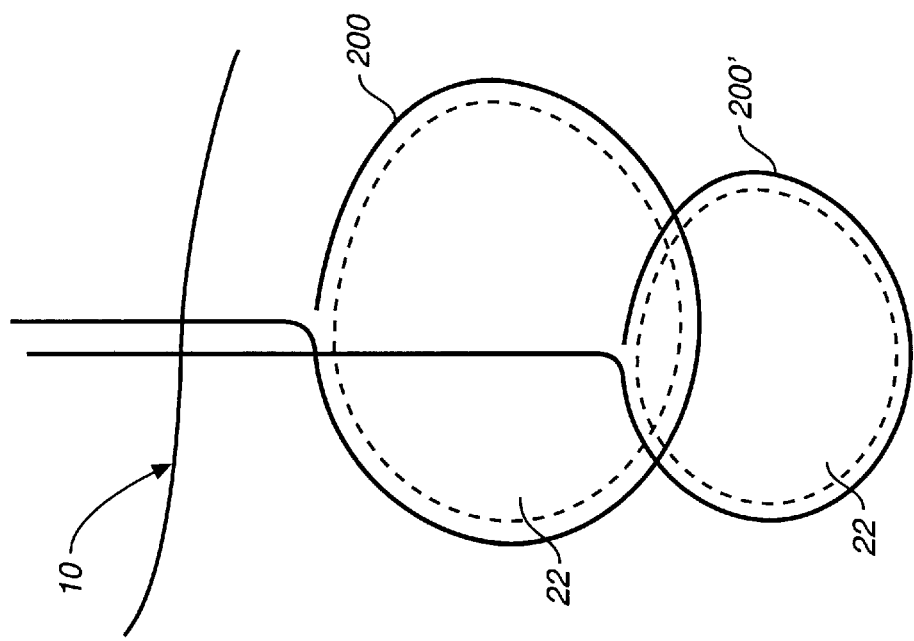
FIG._24B
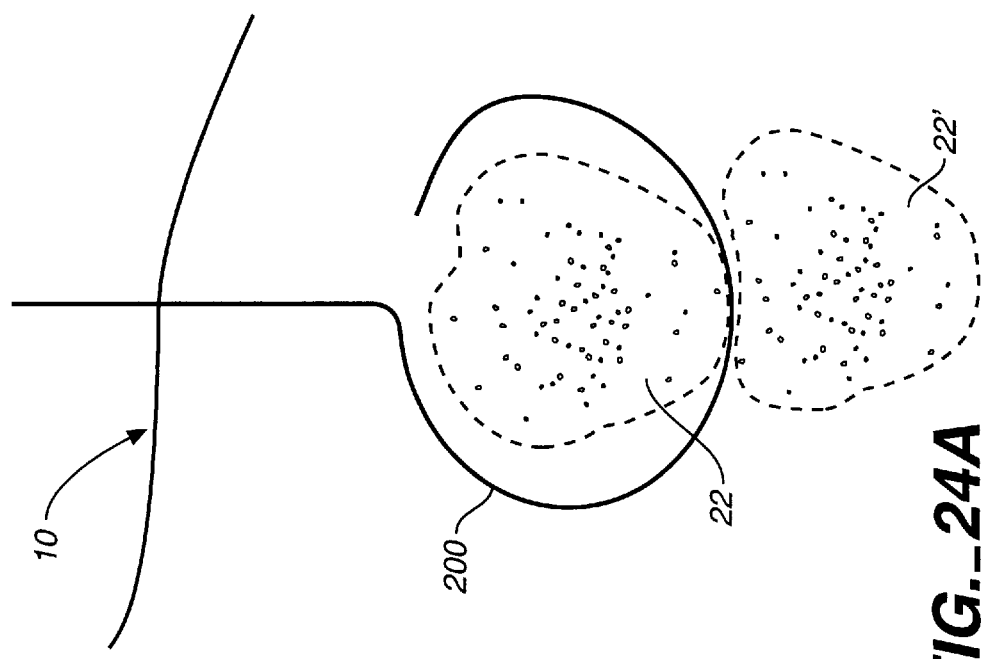
FIG._24A

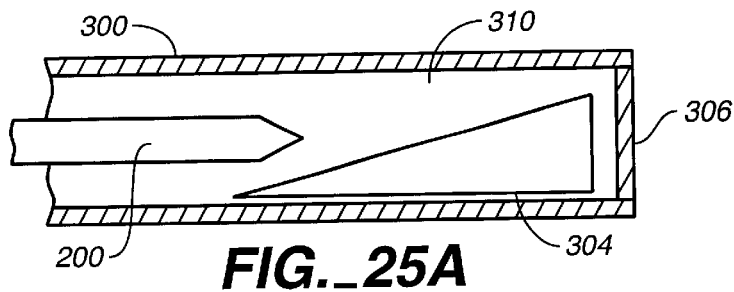
FIG._25A
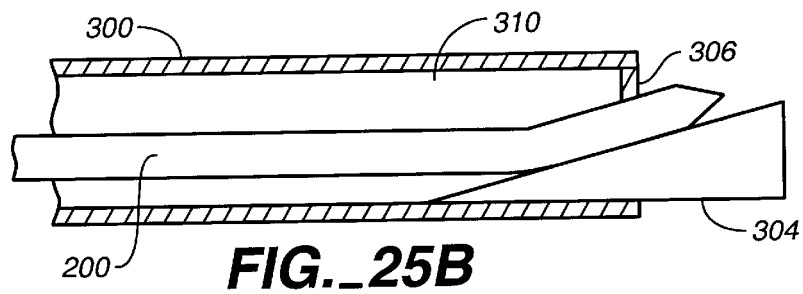
FIG._25B
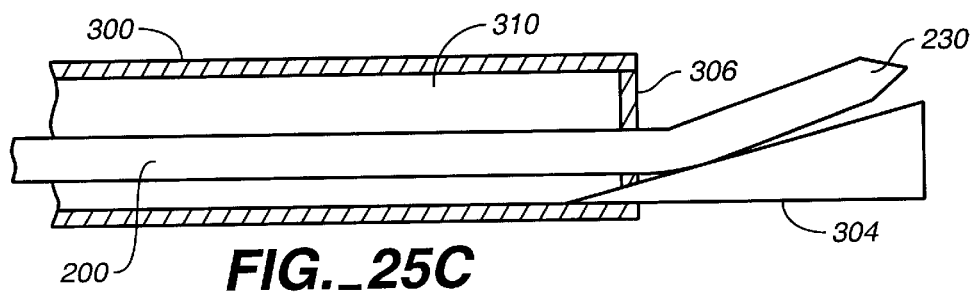
FIG._25C
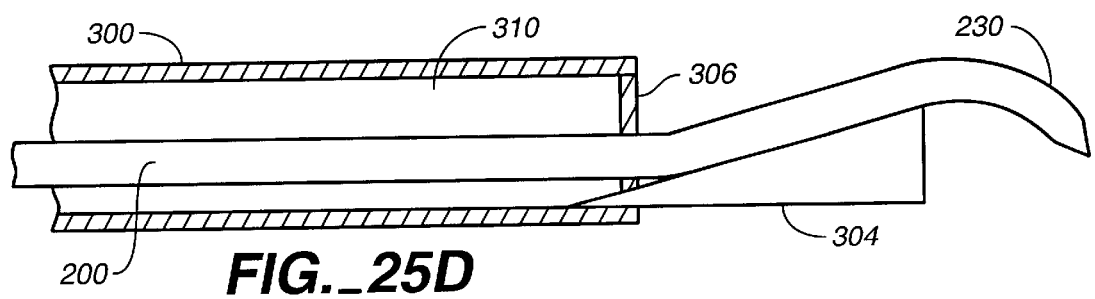
FIG._25D

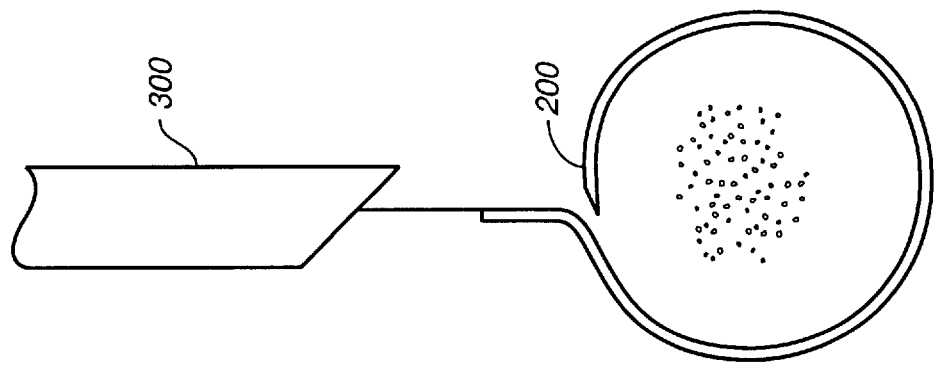
FIG._25G
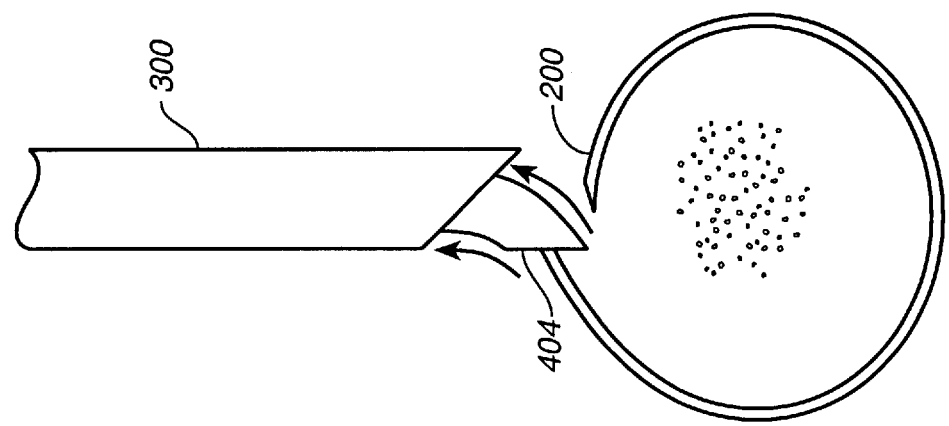
FIG._25F
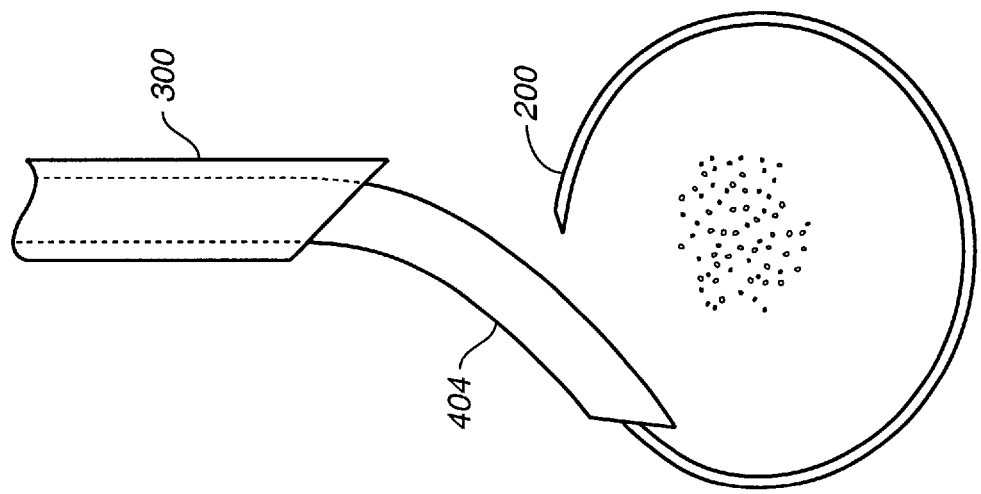
FIG._25E

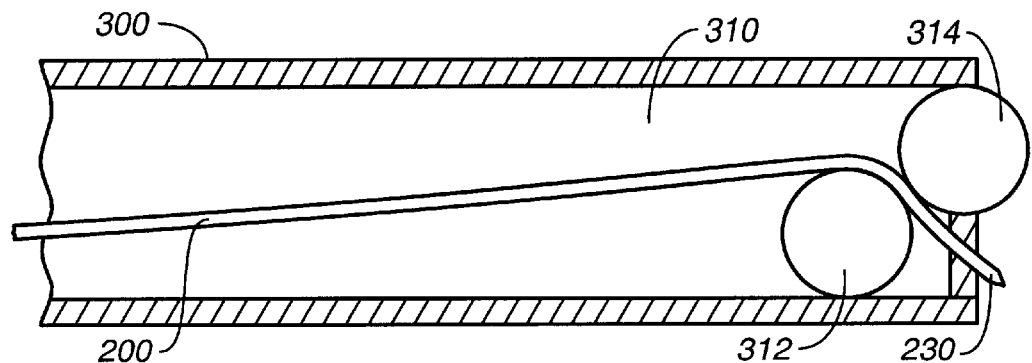
FIG. _26A
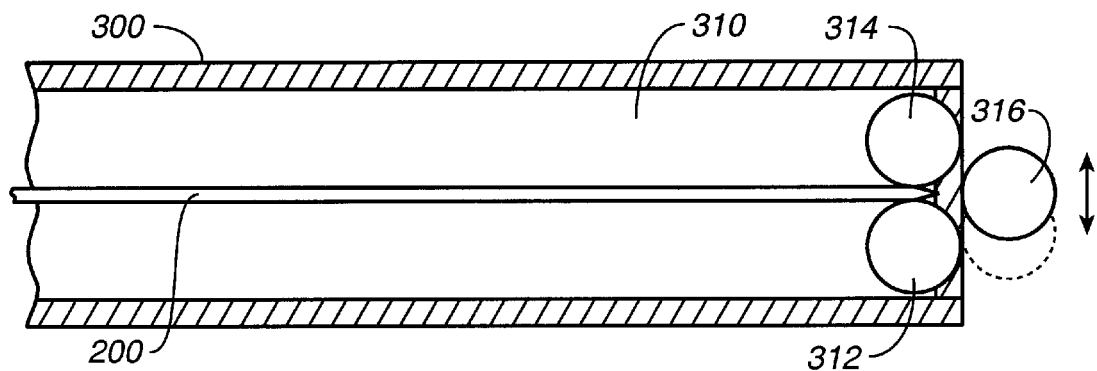
FIG. _26B

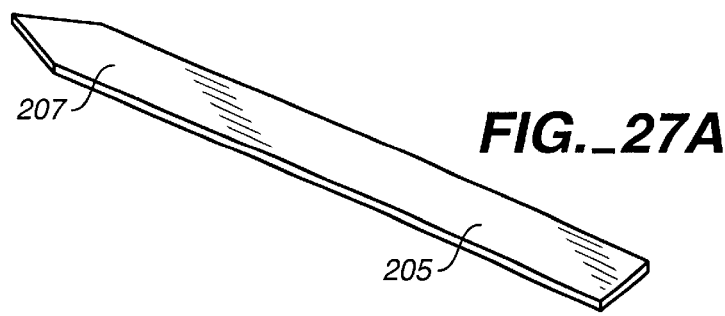
FIG._27A
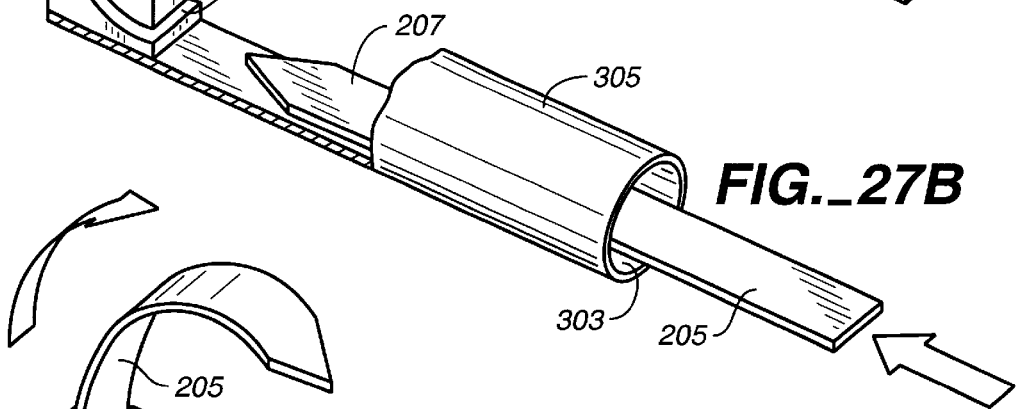
FIG._27B
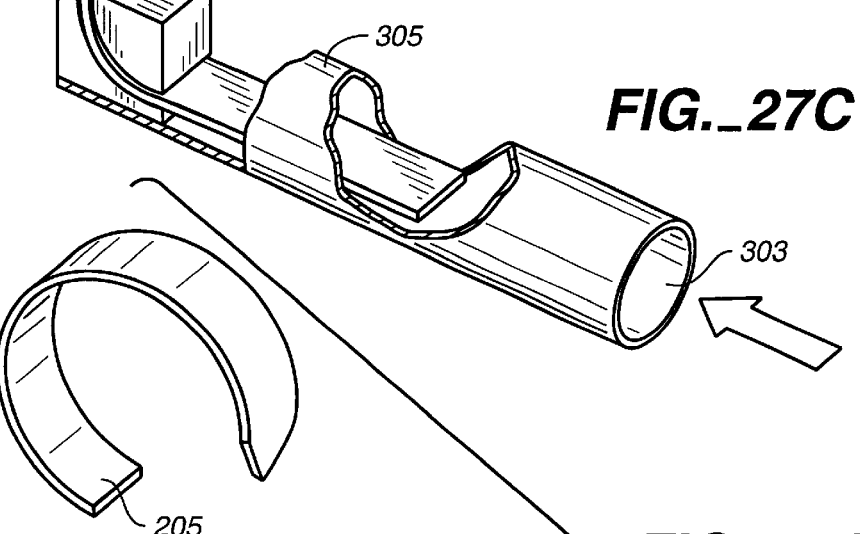
FIG._27C
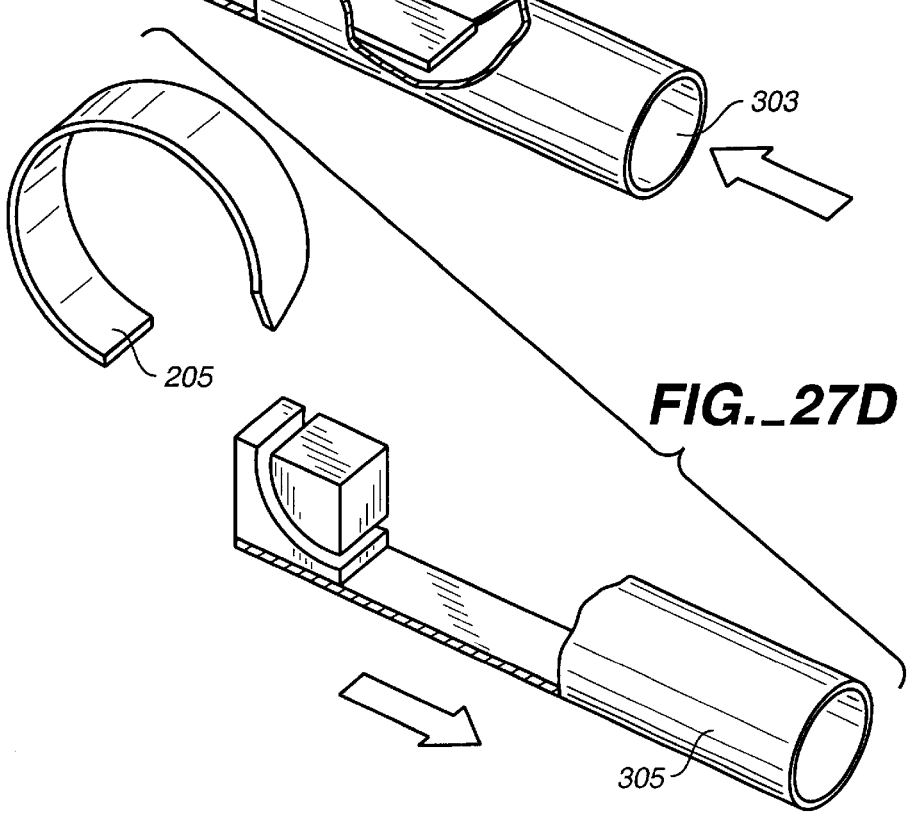
FIG._27D

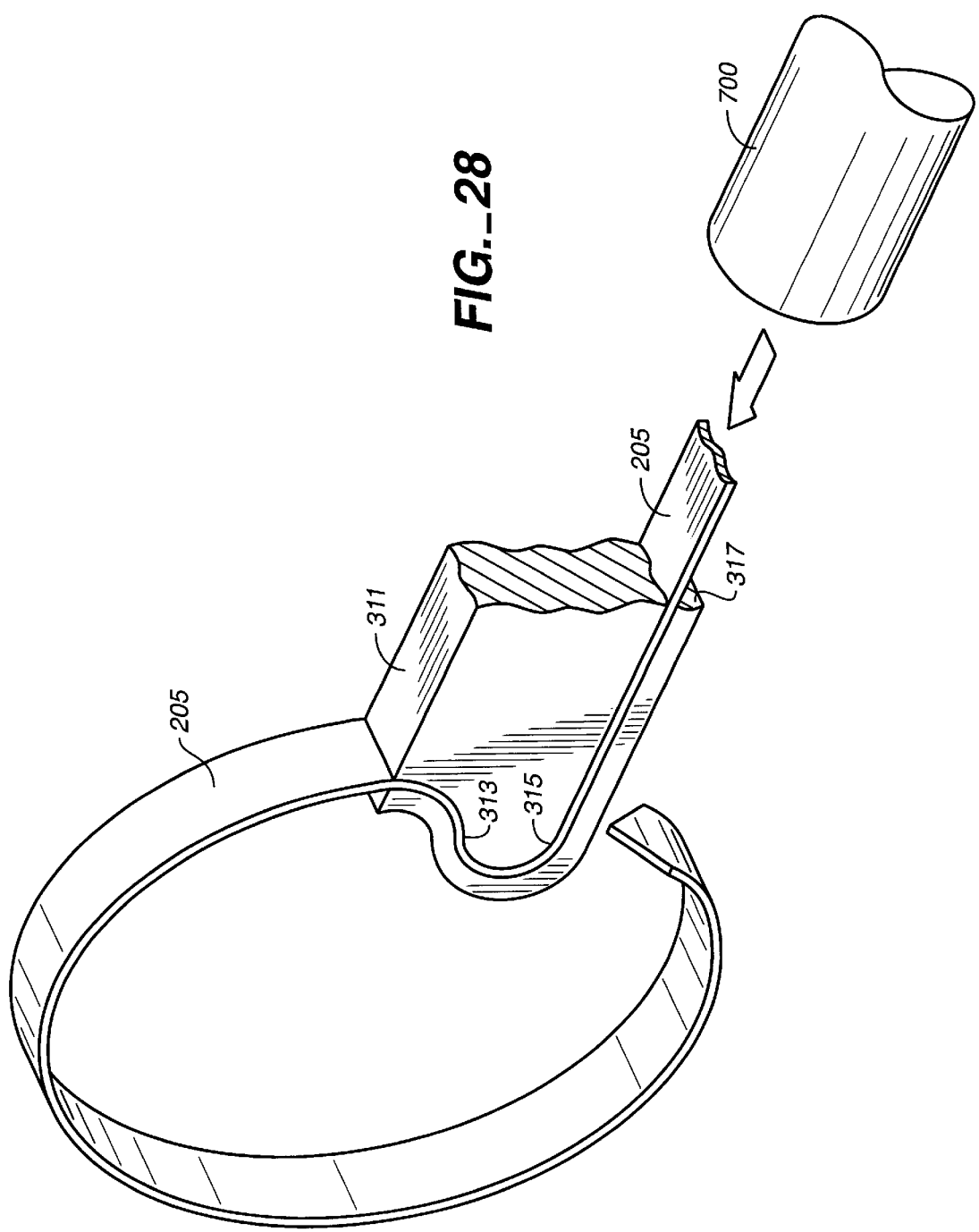
FIG._28

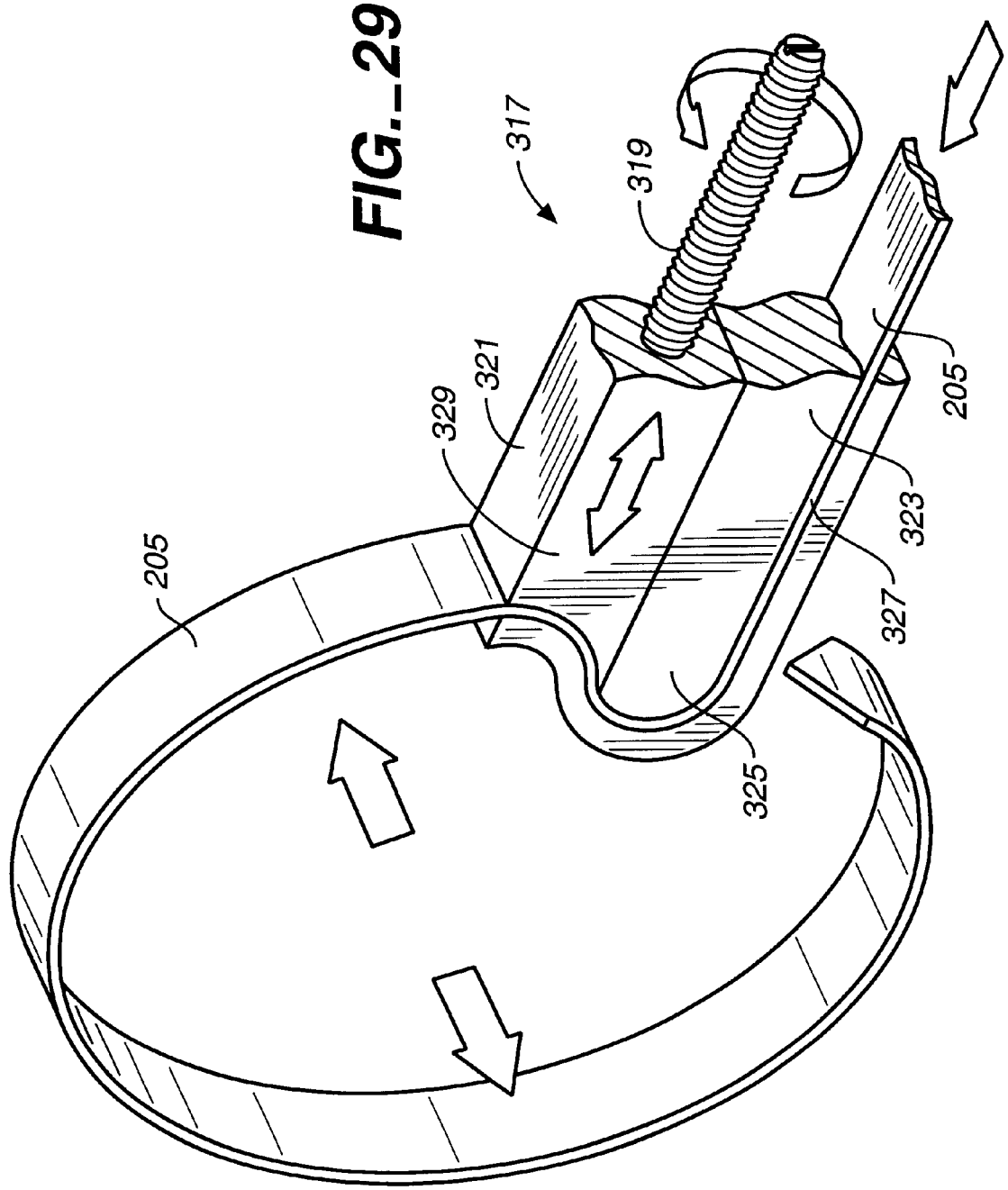
FIG._29

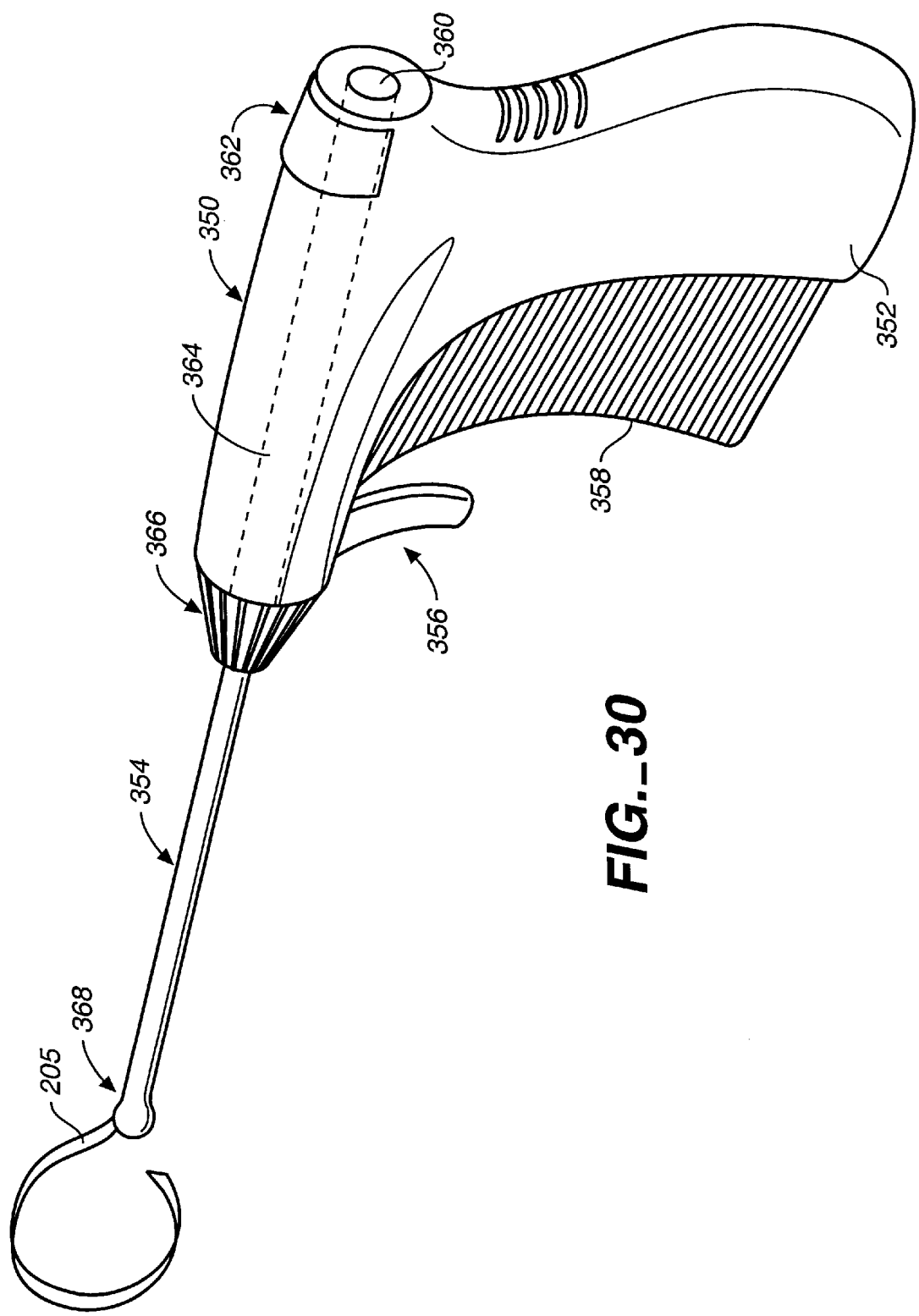
FIG._30

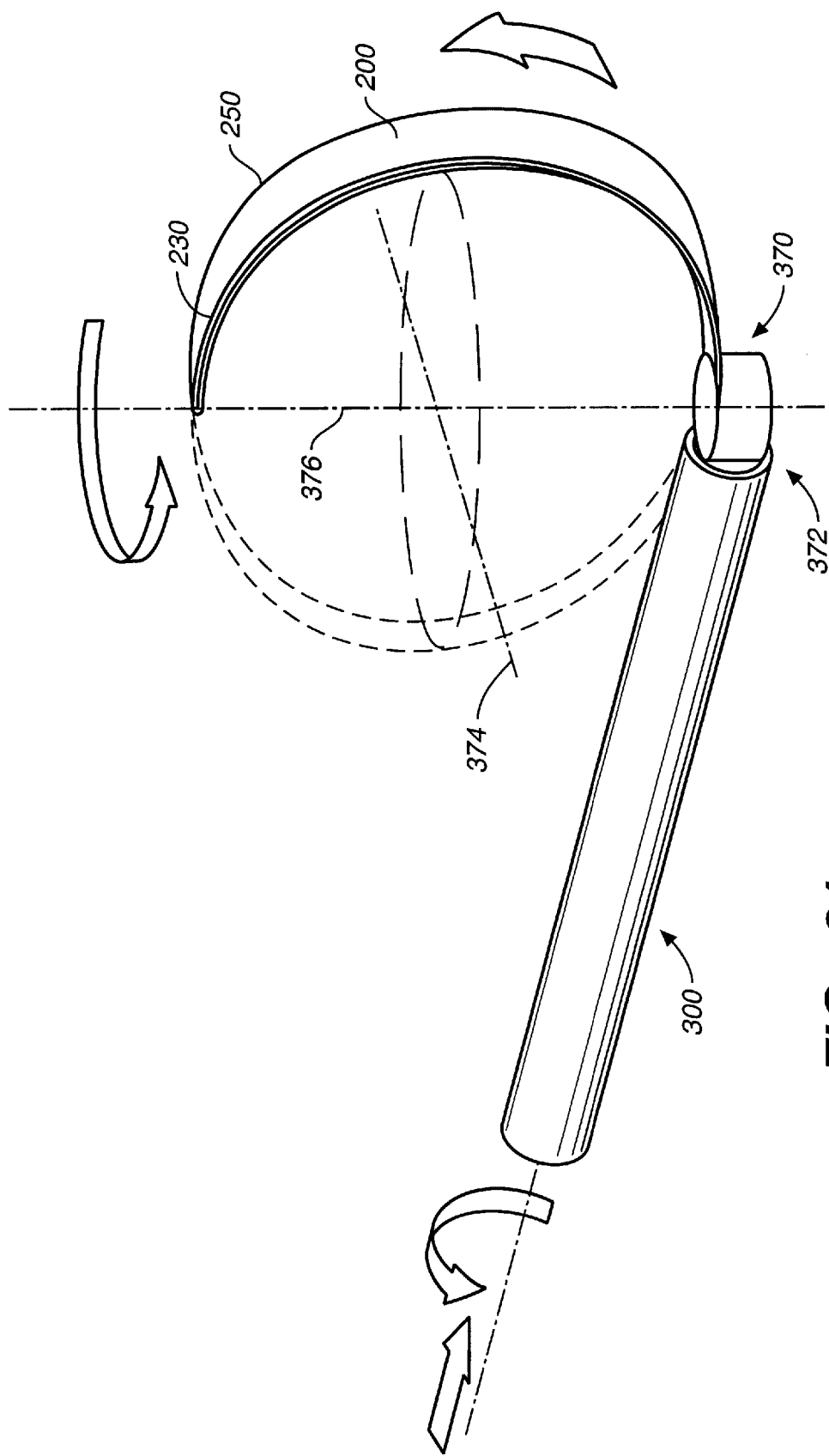
FIG._31

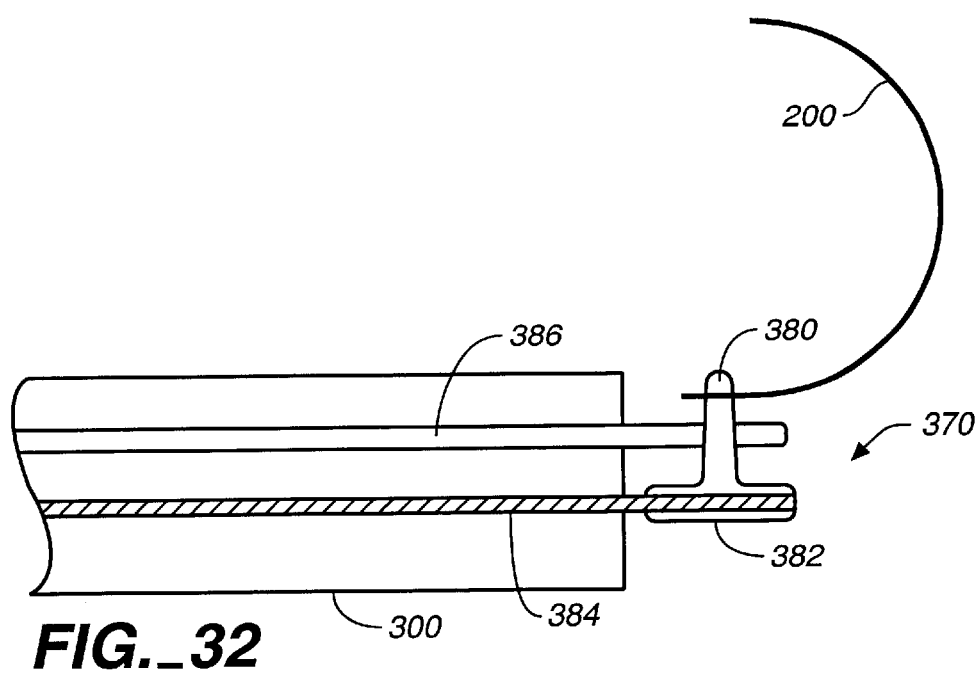
FIG._32
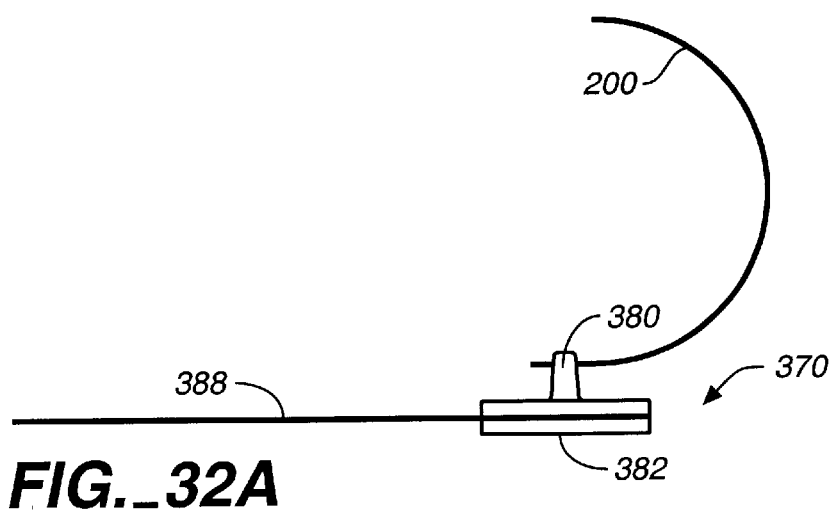
FIG._32A
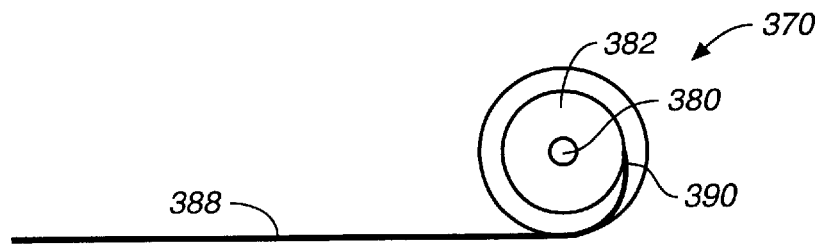
FIG._32B

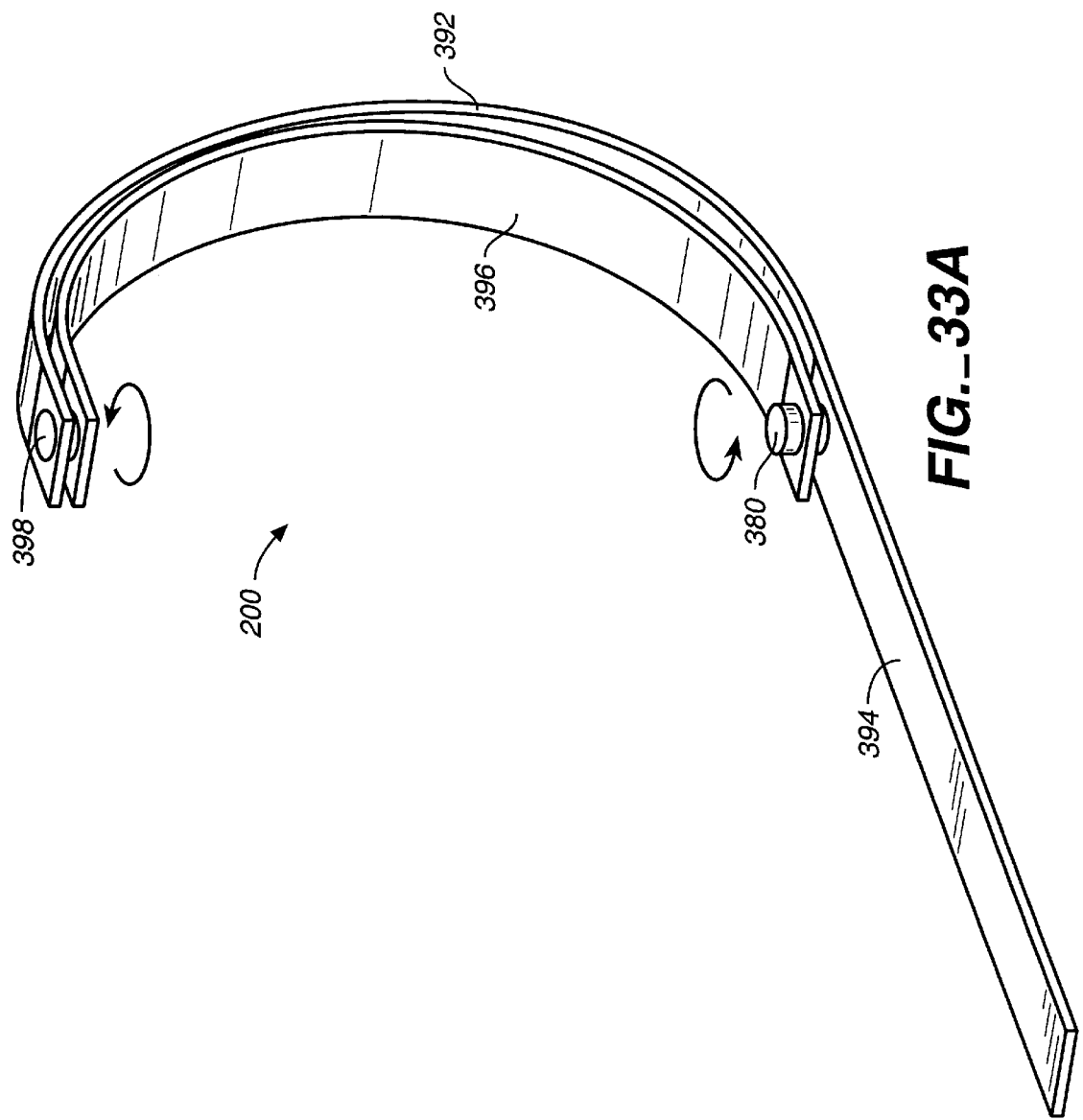
FIG._33A

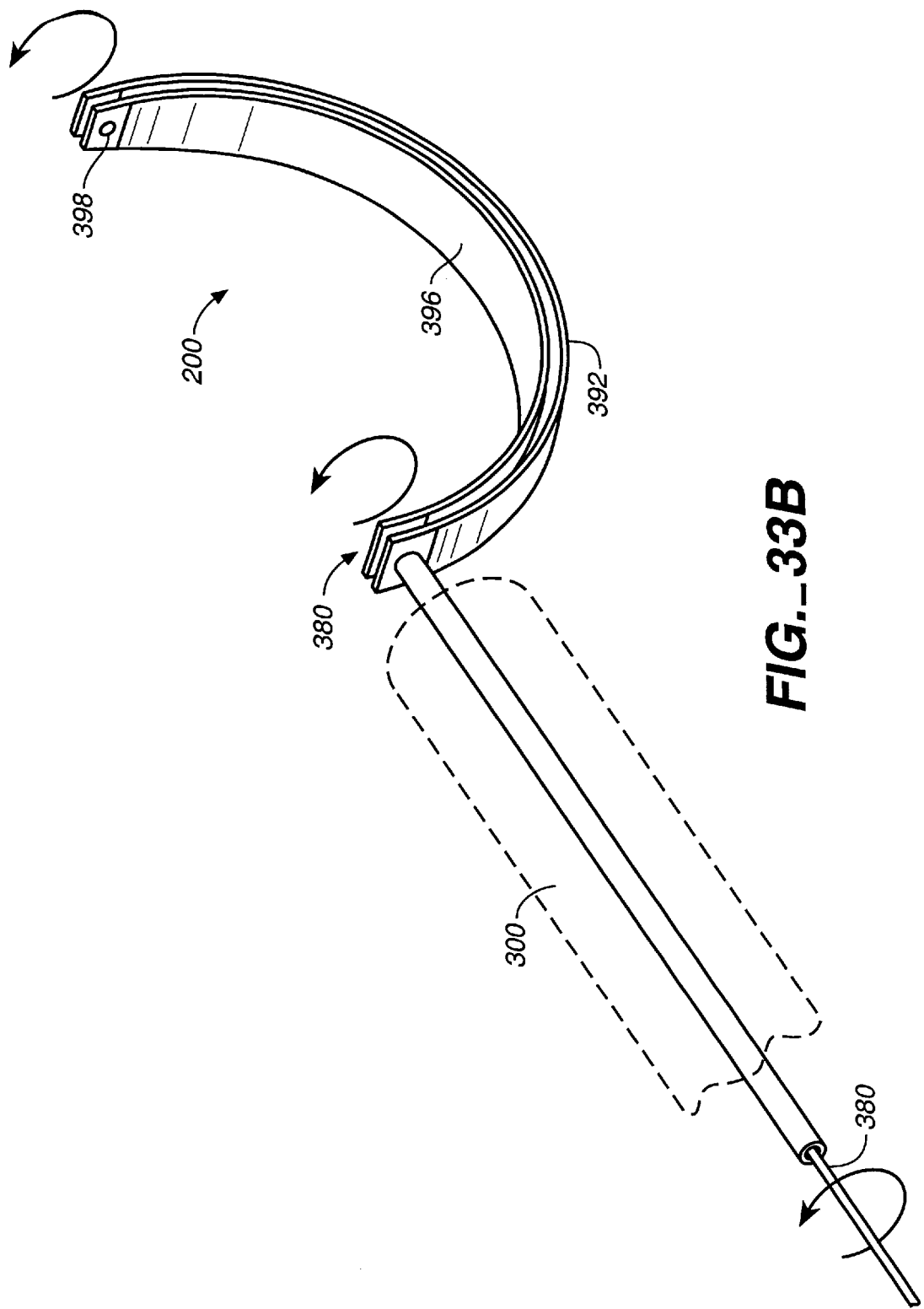

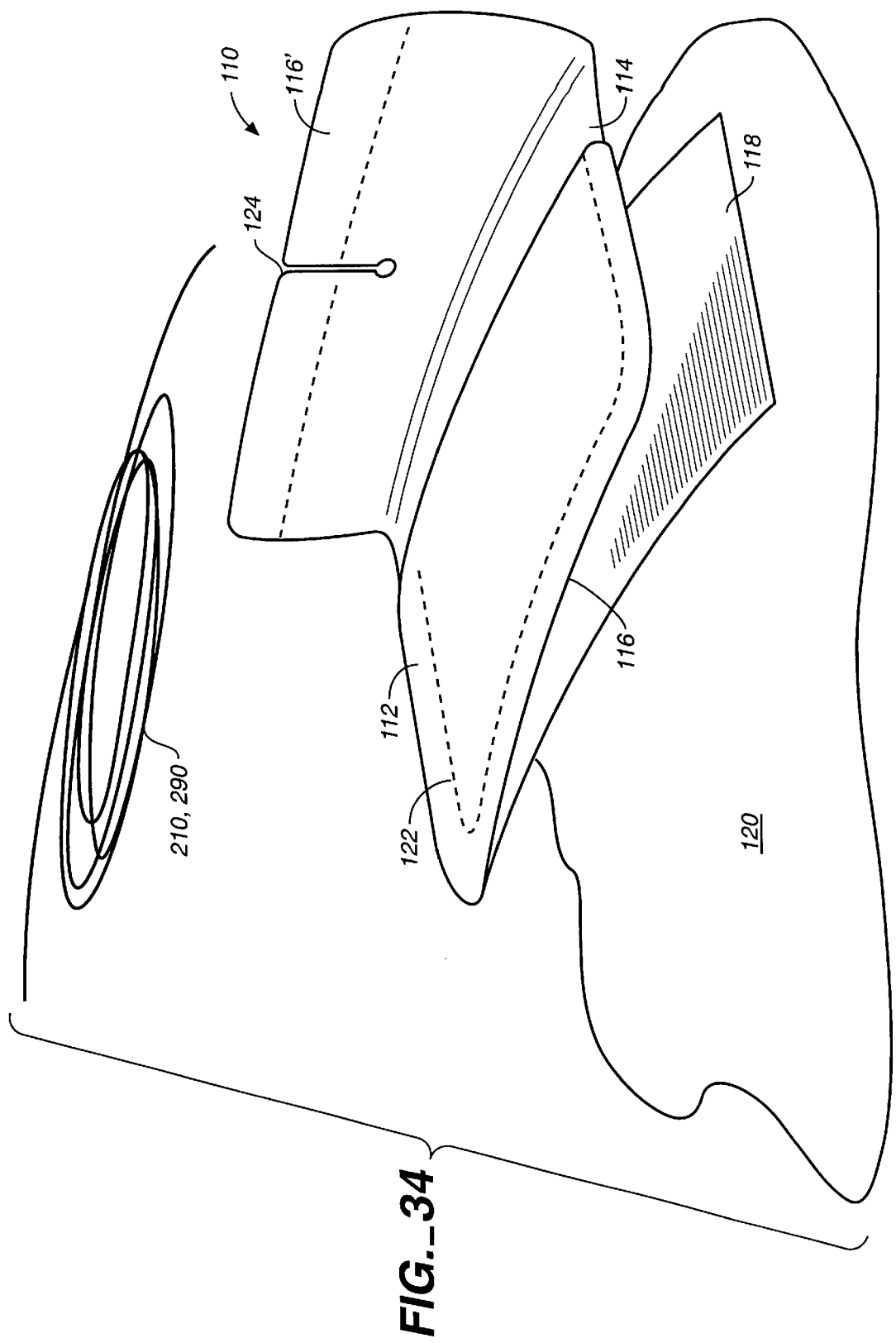
FIG._34

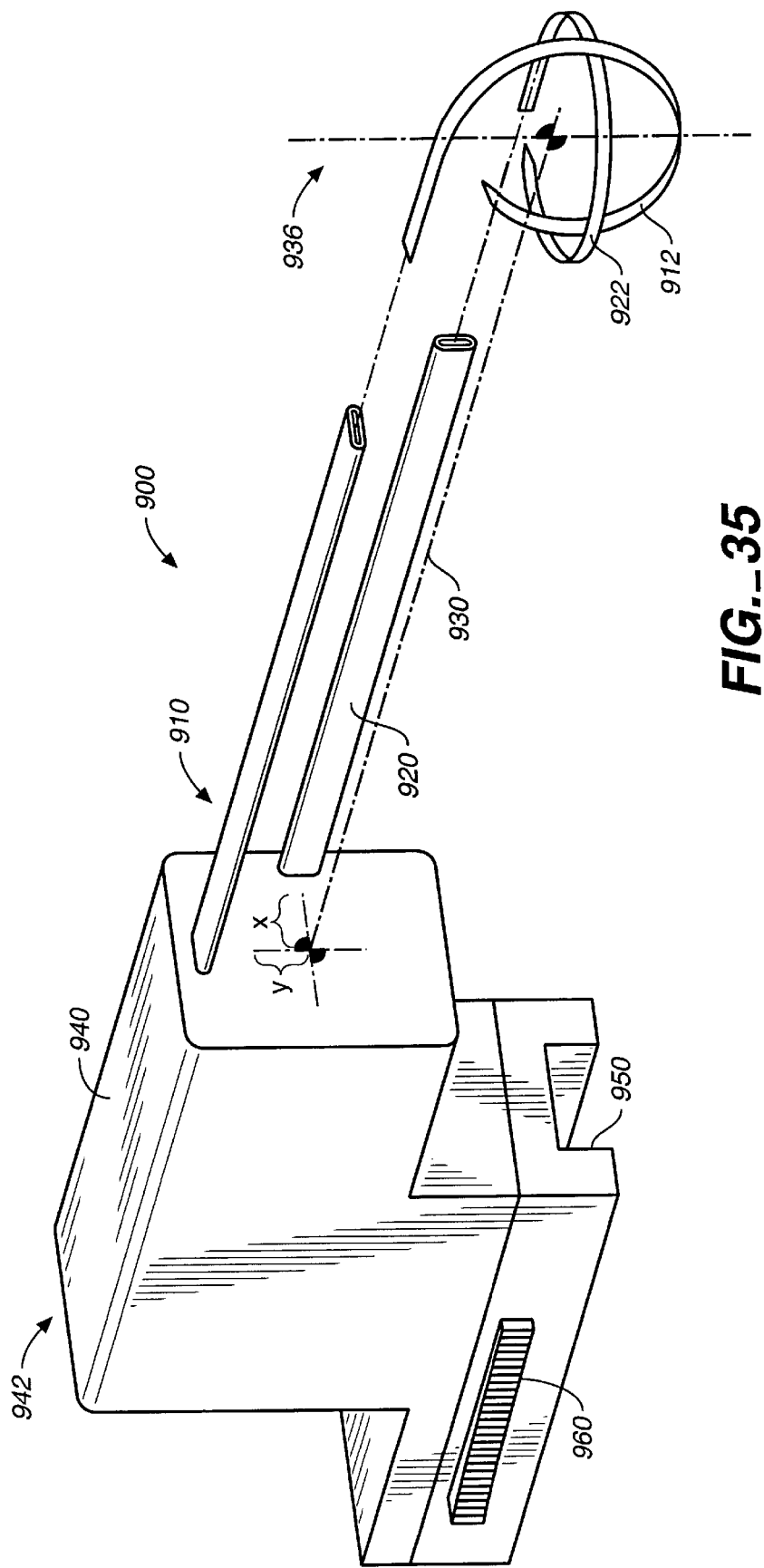
FIG._35

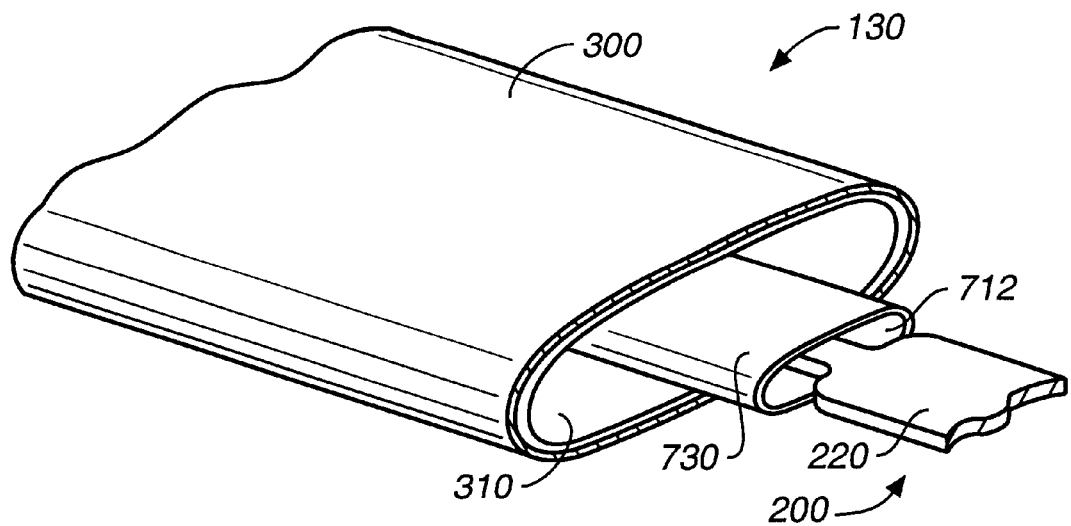
FIG._36A
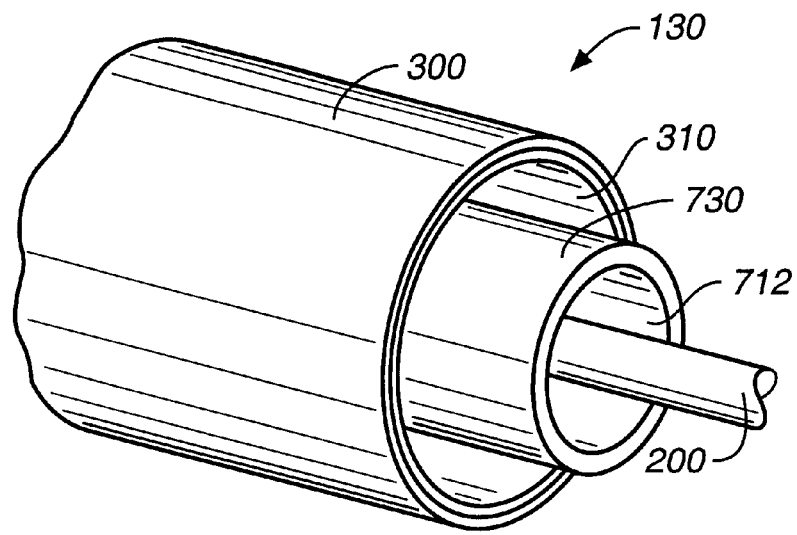
FIG._36B

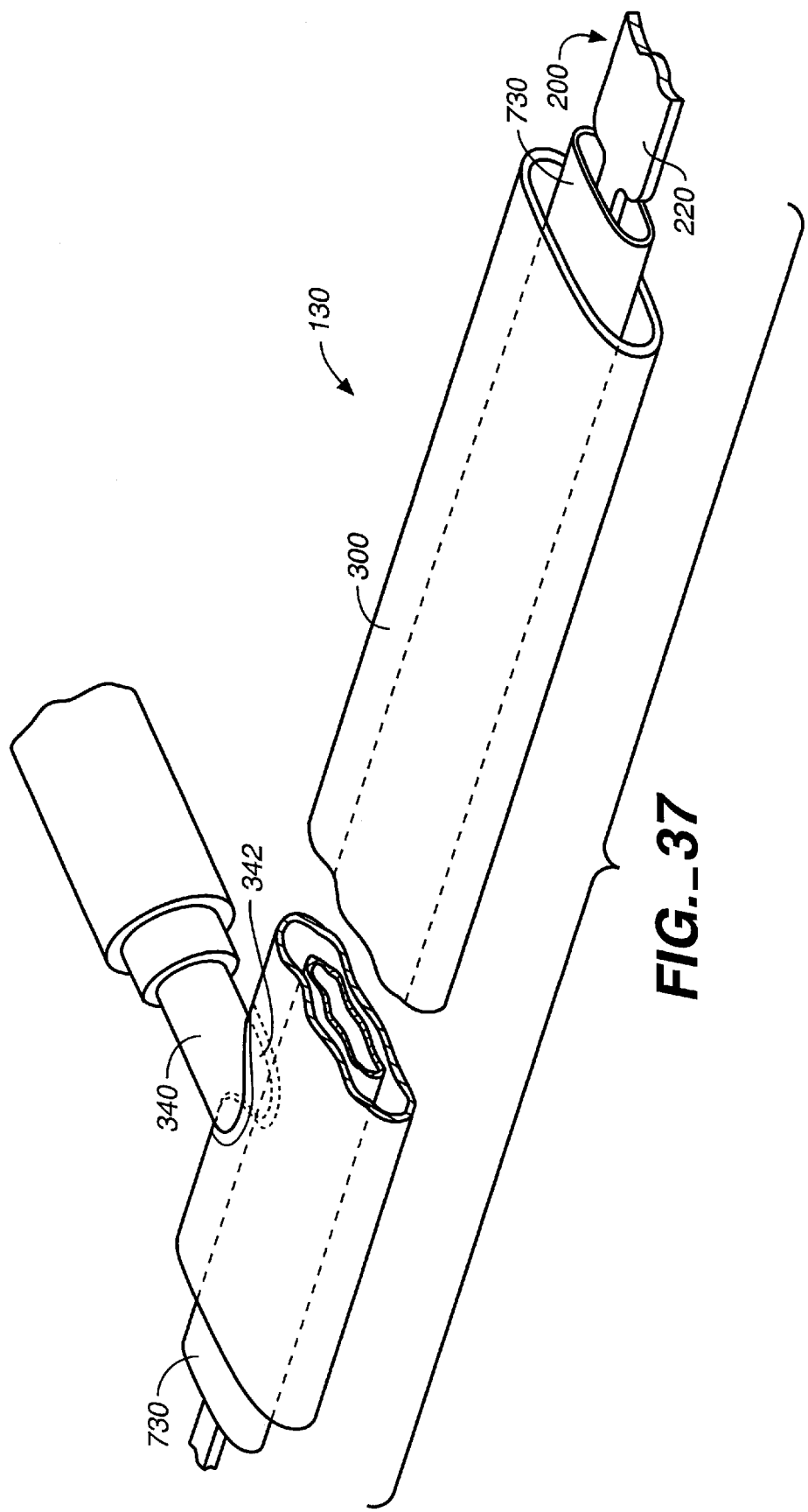
FIG._37

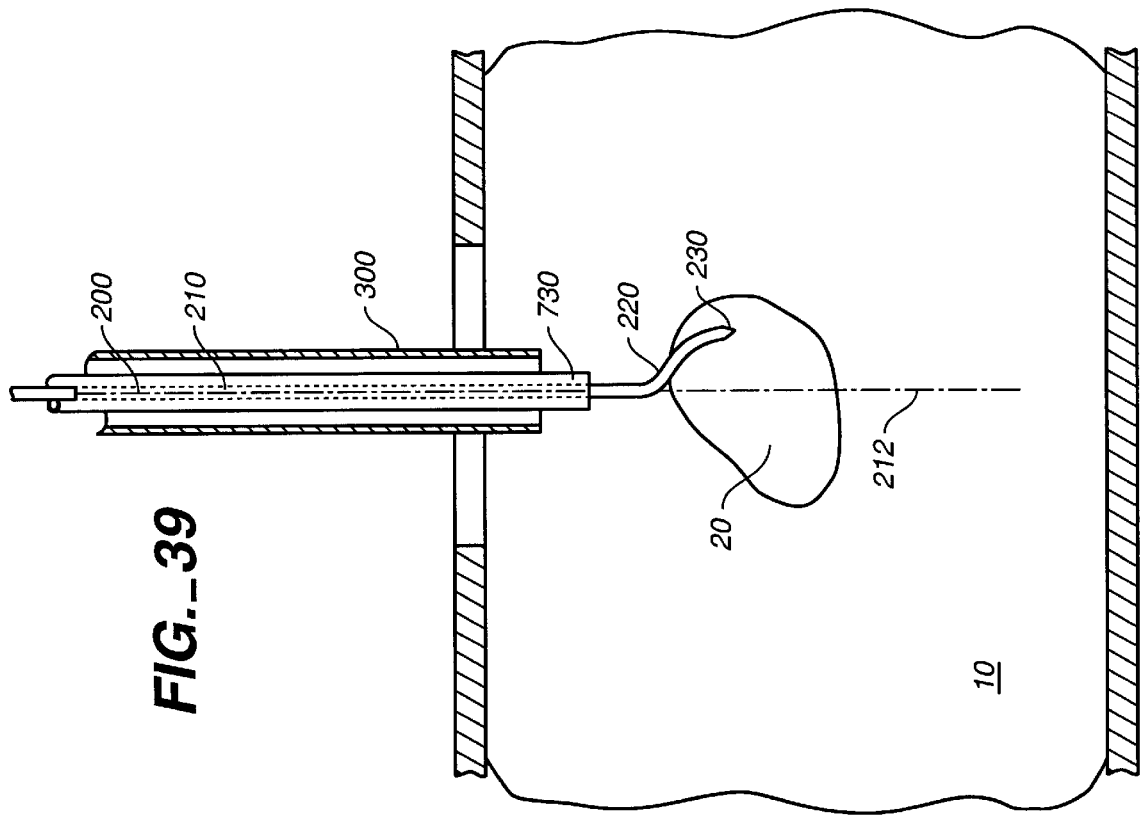
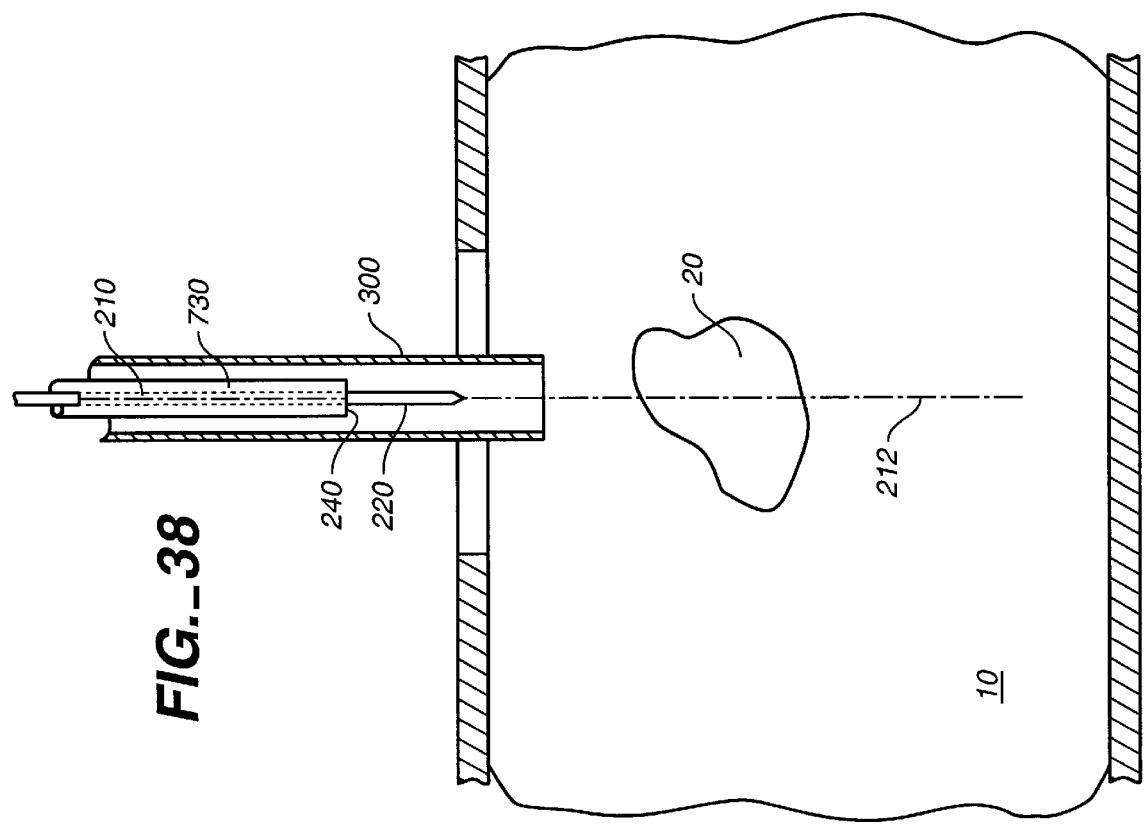

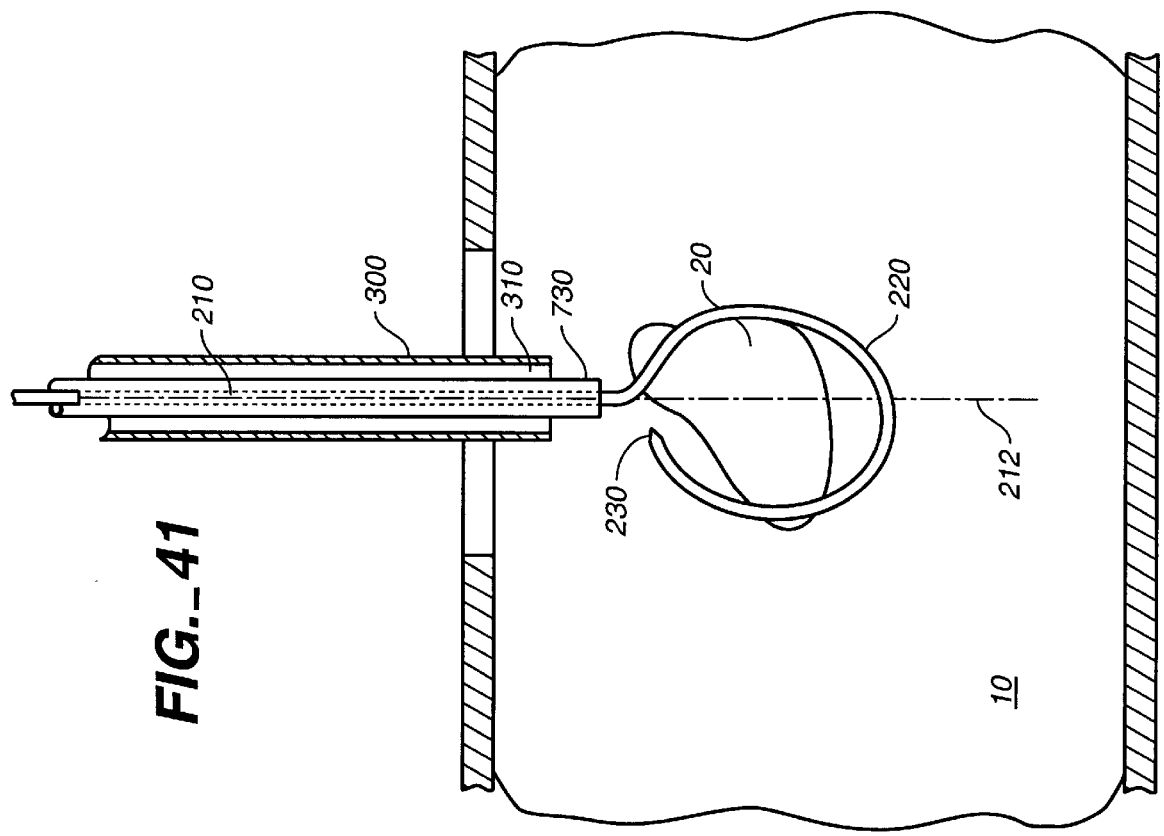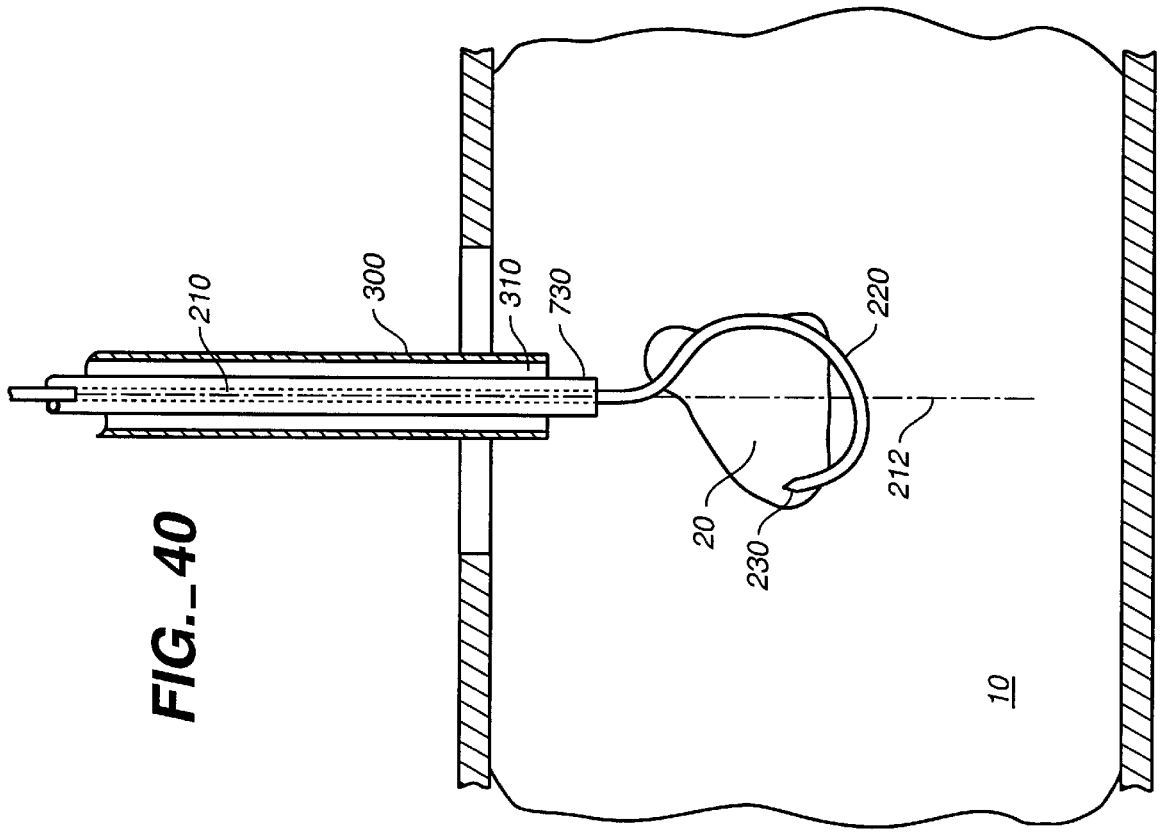

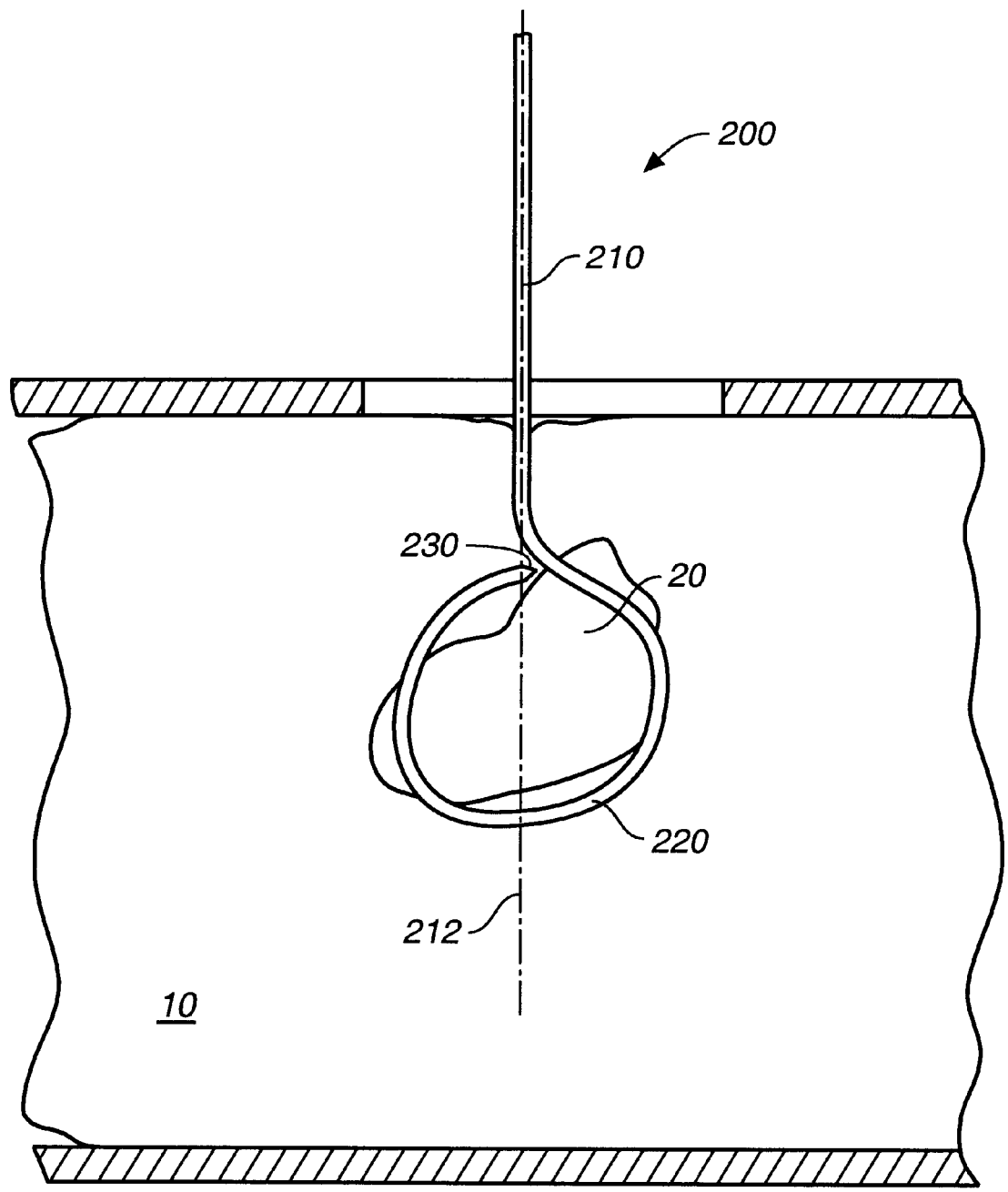
FIG._42

DEVICE FOR ACCURATELY MARKING TISSUE

CROSS-REFERENCE TO RELATED APPLICATIONS

This application is a continuation-in-part of PCT/US01/05013, filed Feb. 16, 2001, which in turn is a continuation-in-part of U.S. patent application Ser. No. 09/699,254, filed Oct. 27, 2000, pending which in turn is a continuation-in-part of U.S. patent application Ser. No. 09/613,686, filed Jul. 11, 2000, now U.S. Pat. No. 6,405,733 which in turn is a continuation-in-part of U.S. patent application Ser. No. 09/507,361, filed Feb. 18, 2000 pending. The entirety of each application is hereby incorporated by reference.

FIELD OF THE INVENTION

This invention relates generally to tissue localizing devices and methods for their deployment and excision. More particularly, this invention relates to an improved tissue localizing device having the ability to fixedly yet removably bound a tissue volume containing a region of interest, such as a nonpalpable lesion, foreign object, or tumor, preferably but not necessarily without penetrating that tissue volume. This invention also more particularly relates to methods for deploying that device and removing it with an enclosed and intact tissue volume.

BACKGROUND

Despite the advances made in technologies such as medical imaging to assist the physician in early stage diagnosis and treatment of patients with possible atypical tissue such as cancer, it is still often necessary to sample difficult-to-reliably-reach organ or tissue lesions by biopsy to confirm the presence or absence of abnormalities or disease.

One disease for which biopsy is a critical tool is breast cancer. This affliction is responsible for 18% of all cancer deaths in women and is the leading cause of death among women aged 40 to 55.

In the detection and treatment of breast cancer, there are two general classes of biopsy: the minimally invasive percutaneous biopsy and the more invasive surgical, or "open", biopsy.

Percutaneous biopsies include the use of fine needles or larger diameter core needles. They may be used on palpable lesions or under stereotactic x-ray, ultrasonic, or other guidance techniques for nonpalpable lesions and microcalcifications (which are often precursors to metastatic cell growth). In the fine needle biopsy, a physician inserts a small needle directly into the lesion and obtains a few cells with a syringe. Not only does this technique require multiple samples, but each sample is difficult for the cytologist to analyze as the specimen cells are isolated outside the context of healthy surrounding tissue.

Larger samples may be removed via a core biopsy. This class of procedures is typically performed under stereotactic x-ray guidance in which a needle is inserted into the tissue to drill a core that is removed via vacuum aspiration, etc. Typically four to five samples are taken from the body. Examples of such stereotactic biopsy methods include the MAMMOTOME vacuum aspiration system by Johnson & Johnson of New Brunswick, N.J., the ABBI system by United States Surgical Corporation, Norwalk, Conn., and the SITESELECT system by Imagyn, Inc. of Irvine, Calif.

Open biopsies are advisable when suspicious lumps should be removed in their entirety or when core needle biopsies do not render sufficient information about the nature of the lesion. One such type of open biopsy is the wire localization biopsy.

After multiple mammograms are taken of the breast, the images are analyzed by a computer to determine the location of the suspect lesion in three dimensions. Next, after a local anesthetic is administered, a radiologist inserts a small needle into the breast and passes the needle through the suspect tissue. The radiologist then passes a wire with a hook on its end through the needle and positions the hook so that the end of the wire is distal to the suspect tissue. A final image is taken of the lesion with the accompanying wire in place, and the radiologist marks the film with a grease pencil to indicate the x-ray indicators of a suspicious lesion that should be removed. The wire is left in the tissue and the patient is taken to the operating room, sometimes hours later, where the suspect tissue is removed by a surgeon. The sample is sent to a radiologist to determine, via an x-ray examination, if the sample contains the indicators such as microcalcifications and if the sample size and border are adequate to confirm the removal of all suspicious tissue.

Examples of such wire markers are well known in the art. See, e.g., the following patents, each of which is incorporated herein by reference: U.S. Pat. No. 5,158,084 to Ghiatas, U.S. Pat. No. 5,409,004 to Sloan, U.S. Pat. No. 5,059,197 to Urie et al., U.S. Pat. No. 5,197,482 to Rank, U.S. Pat. No. 5,221,269 to Miller et al., and U.S. Pat. No. 4,592,356 to Gutierrez. Other devices such as that described in U.S. Pat. No. 5,989,265 to Bouquet De La Joliniere et al. and U.S. Pat. No. 5,709,697 to Ratcliff et al., each incorporated herein by reference, are directed to similar devices.

Despite the advantages of wire localization techniques to locate the suspect tissue for the surgeon, they have a number of severe limitations.

Such wires are often inaccurately placed and they cannot be removed except by surgical excision. For these reasons, the radiologist must mark the x-ray film or prepare notations providing instructions to the surgeon on how to find the lesion as a backup to confirm the proper location of the needle.

Because the distal tip of the wire might have been placed anywhere from the very center of the lesion to quite some distance away from the lesion, the surgeon must guide a scalpel along the wire and rely upon the skill of the radiologist and the marked x-ray film in the excision procedure. Even if the wire has been properly placed in the lesion and the x-ray film clearly shows the lesion boundary or margin, the surgeon often cannot see the tip of the wire (given the surrounding tissue) so she must remove a larger portion of tissue than is necessary to ensure proper excision.

If the lesion is not found at the end of the wire, the surgeon ends up cutting or removing non-afflicted tissue without removing the lesion. Also, if the tip of the wire penetrates the lesion, the surgeon may sever the lesion in cutting through the tissue along the wire to reach its end. In the latter case, a re-excision may be necessary to remove the entire lesion. Over twenty-five percent of wire localization procedures require re-excision. Post-excision re-imaging is almost always performed prior to closing the surgical field to ensure that the targeted tissue volume containing the suspect lesion is removed.

When marking lesions in the breast, two paddles are typically used to compress and stabilize the breast for placement of the wire. Upon release of the breast from compression, the wire marker can dislodge or migrate to another position away from the suspect tissue. It may also migrate while the patient awaits surgery. In addition, the fact that the breast is in an uncompressed state for the excision procedure renders a different view of the lesion with respect to the healthy tissue.

Various tissue localization systems have been developed to minimize inadvertent migration of the wire by configuring the wire with a bend or hook, such as Ghiatas et al., discussed above, U.S. Pat. No. 5,011,473 to Gattuma, and the MAMMALOK needle/wire localizer sold by Mitek Surgical Products, Inc., Dedham, Mass. Even if a wire does not migrate after placement, the surgeon cannot determine the shortest path to the lesion; rather, the surgeon must always follow the wire, which is rarely the more cosmetically desirable path to the lesion (such as a circumareolar approach).

Because the distal tip of the wire is often placed in the center of the suspect tissue, a problem known as "track seeding" can occur in which possible cancerous or precancerous cells are disturbed by the wire and are distributed to unaffected tissue during the procedure.

Aside from the above concerns, the use of a localization wire marker presents logistical problems. After placement, the wire protrudes from the body. It is almost always necessary for the patient to proceed with the surgical removal of the lesion immediately after wire placement to minimize the chance of infection, wire breakage or disturbance, etc. However, delays between placement of the wire and eventual excision often can exceed several hours.

What is needed is a tissue locating device that may be accurately yet removably placed into a region of tissue to surround a volume of tissue that contains a suspect region, preferably without penetrating that volume to disturb it. Such a device should reliably define the border of the volume of tissue to be removed without the risk of self- or inadvertent migration. The device should also provide a surface against which the surgeon may reliably cut when excising the tissue. Furthermore, a need remains to improve the interaction between the radiologist and surgeon, eliminate the need for post-excision x-rays and re-excision, reduce the overall time for the procedure, and allow a surgeon to select the shortest or most cosmetically desirable path to the suspect tissue.

SUMMARY OF THE INVENTION

This invention is a tissue localizing device, system, and method for its use.

The tissue localizing device includes a locator element adapted to penetrate tissue so that at least a portion of the locator element defines a tissue border along a first path. This path may include the distalmost portion of the tissue volume. This border in turn defines a volume of tissue for subsequent excision and contains a target region that may be a lesion, foreign object, one or more microcalcifications, or a palpable or nonpalpable mass. This tissue volume is substantially bounded but preferably not penetrated by the locator element. The path the locator element is adapted to follow preferably forms a loop in the tissue having a diameter of at least one centimeter. When deployed, manipulation of a proximal portion of the locator element results in a corresponding direct or proportional manipulation of the tissue volume it bounds. The proximal portion can, but need, not include a tail portion to aid in manipulation.

Preferably the locator element is a partially radiopaque ribbon with one or more optional cutting surfaces. The locator element also preferably exhibits shape memory characteristics. Alternatively, the locator element may be plastically deformed to take an arcuate or curvilinear shape during deployment through a die.

A shoulder portion may be included in the locator element defining a boundary between a preferably more flexible, less rigid proximal portion having a smaller cross-sectional area and a stiffer, more rigid distal portion having a larger cross sectional area compared to that of the proximal portion.

This device may contain a second locator element adapted to penetrate tissue so that at least a portion of it further defines the tissue border along a second path. Again, the target region is substantially bounded but preferably not penetrated by the second locator element. Each of the first and second locator elements may be deployed through a deployment tube having a lumen in which the locator elements are slideably disposed and a distal end through which they may exit into the tissue. The second locator element may be adapted to deploy into the tissue so that it defines a second plane that is not parallel to a first plane defined by the first locator element. These planes may be angularly displaced about a common axis about ninety or forty-five degrees with respect to one another.

The locator elements are adapted to be substantially aligned when deployed with a central axis of the tissue volume they bound or with a tangential axis of that volume.

An optional suture, flexible wire, cable or composite material may be affixed to a proximal end of the locator element to extend through the tissue volume and outside the skin surface when deployed in the body.

This invention is also a tissue localization system which includes a tissue cutting element positionable within a lumen of a driver tube, a trocar positionable within the driver tube lumen, a locator element deployment tube positionable within the driver tube lumen, and at least one locator element positionable within the deployment tube. The cutting element may additionally comprise at least one lumen or tubular member having a distal end disposed along its length.

The locator element is adapted to penetrate tissue so that at least a portion of the locator element defines a tissue border along a first path. The tissue border defines a volume of tissue for subsequent excision along the border, and contains a target region that is substantially bounded by the locator element.

An orientation element also may be attached to the locator element deployment tube, which may be rotatable in fixed angular increments and/or may be infinitely rotatably variable.

A source of energy, such as electrical (RF, etc.), thermal, acoustic, mechanical, or other may be connected to the locator element. The locator element may also be at least partially electrically insulated by a coating of insulative material on one or more sides of the element. This insulative material may have a low coefficient of friction for ease of entry into the tissue if desired.

The locator element deployment tube may comprise a distal end having a locator element cold forming die that may be adapted to plastically deform the locator element into an arcuate shape. The die may include a reverse curve and a positive curve for shaping the locator element, and it may also comprise an axially adjustable upper portion connected to a lower portion.

This invention is also a method for fixedly placing a removable locator element in tissue. This method is accomplished by penetrating through tissue at a first site to create a port or a pathway for accessing a targeted tissue volume to be excised, inserting a deployment tube containing a locator element slideably contained within a lumen of the tube through the port to a position adjacent the targeted tissue volume, and advancing a locator element through a distal end of the tube and penetrating tissue so that at least a portion of the locator element defines a tissue border along a first path. The tissue border will define a volume of tissue for subsequent excision along the tissue border. The tissue volume will contain a target region that is substantially bounded but not penetrated by the locator element.

Alternatively, the invention is a method for excising a volume of tissue that comprises advancing a locator element through tissue to define a tissue border of the volume of tissue to be excised, and cutting tissue substantially along a surface of the locator element opposite a surface of the locator element disposed immediately adjacent the tissue volume.

The locator element may be proximally withdrawn from the tissue after it is advanced to define the tissue border for eventual re-advancement through the distal end of the deployment tube or complete removal from the body.

The locator element may be placed under x-ray guidance, stereotactic x-ray guidance, ultrasonic guidance, magnetic resonance imaging guidance, and the like. Target region visibility may be enhanced by, e.g., the placement or injection of an echogenic substance, such as collagen, hydrogels, microspheres, or other like biocompatible materials, or by the injection of air or other biocompatible gases or contrast agents.

A second and even third or more locator element may also be advanced through the distal end of the deployment tube to penetrate tissue so that at least a portion thereof further defines the tissue border along a second and even third path. The second path and the third path may be non-parallel to the first path occupied by the first locator element, and may be angularly displaced with respect thereto approximately thirty degrees, forty-five degrees, ninety degrees, or at any other angle or angles the radiologist so desires.

This method also includes the step of excising the tissue volume defined by the one or more locator elements. This may be accomplished by surgically accessing the locator element and cutting tissue substantially along a surface of the locator element opposite a surface of the locator element disposed immediately adjacent the tissue volume. Preferably, the device is palpable when in position around the tissue volume. Tissue may be penetrated through any accession path to the tissue volume as the surgeon sees fit. For instance, the surgeon may cut down along the locator element deployment tube, or, when the device is disposed in breast tissue, circumareolarly.

Furthermore, excision may be accomplished or complemented by at least partially energizing the locator element with electrical energy such as RF energy, mechanical energy, thermal energy, vibrational or acoustic energy, and the like. Rotation of the locator element or elements through an angular displacement to facilitate cutting through tissue to remove the tissue volume is contemplated.

This invention also includes a tissue locator element pusher assembly. This pusher assembly includes a housing having a lumen, a pusher slideably disposed in the housing lumen, and a delivery tube affixed to the housing having an optional sharpened distal tip and a tube lumen adapted for slidably receiving the pusher. The pusher may also have a pusher lumen for receiving at least a portion of a tissue locator element. An adjustable fastener for slidably fixing a portion of a tissue locator element to the pusher may also be included.

A deployment fixture may be detachably affixed to a distal end of the housing. The deployment fixture may have at least one fixture lumen axially aligned with the pusher lumen and the delivery tube lumen.

The pusher assembly may also have a tissue locator element having proximal and distal portions that is at least partially disposable in the pusher lumen. A shoulder, which may have at least one tab, may be disposed proximal the locator element distal portion. At least a portion of the tab may extend within or outside a plane defined by the locator element.

This invention is also a tissue locator element pusher assembly that includes a housing having a lumen, a pusher having a pusher lumen slidably disposed in the housing lumen, a tissue locator element at least partially disposed in the pusher lumen, and a delivery tube having an optional sharpened distal tip and affixed to the housing. The delivery tube has a tube lumen adapted for slidably receiving the pusher and the tissue locator element.

A deployment fixture may be detachably affixed to a distal end of the housing. The deployment fixture may have at least one fixture lumen axially aligned with the pusher lumen and the delivery tube lumen. This fixture may also have a second fixture lumen disposed in a plane that is generally orthogonal to a plane in which the first fixture lumen is disposed. An adjustable fastener for slidably fixing a portion of a tissue locator element to the pusher may also be included.

A shoulder, which may have at least one tab, may be disposed proximate the locator element distal portion. At least a portion of the tab may extend within or outside a plane defined by the locator element.

Still further, this invention is a tissue locator element pusher assembly that includes a housing having a proximal end, a distal end, a central housing lumen, and at least one longitudinal slot in communication with the housing lumen, and a pusher slidably disposed in the housing lumen. The pusher has a pusher lumen and an adjustable fastener for slidably fixing a portion of a tissue locator element to the pusher, a control lever affixed to the pusher and extending at least partially through the housing slot, and a tissue locator element at least partially disposed in the pusher lumen. The locator element has a shoulder disposed proximate a distal portion of the locator element.

A delivery tube having a tube lumen adapted for slidably receiving the pusher and the locator element may be disposed on the distal end of the housing in communication with the housing lumen.

Further, this pusher assembly may be configured so that axial movement of the control lever will result in a corresponding axial movement of the pusher and the locator element. In this way, the locator element will reversibly extend through an aperture in a distal end of the delivery tube. The assembly may also be set up so that sufficient axial movement of the control lever may cause it to engage a detent disposed in the housing, prohibiting substantial further axial movement of the control lever. The engagement of the control lever and the detent may be configured to correlate to an extension of the locator element shoulder through the delivery tube distal end aperture. The assembly may further be set up so that just prior to engaging the detent, tactile or other feedback is provided to indicate that the engagement point is about to be reached.

Although the tissue locator element is primarily intended to mark a volume of tissue without penetrating it, the tissue locator element may be used as a tissue localization wire in which at least a portion of a tissue volume (which may or may not include a lesion) is penetrated to mark it for later excision.

When used as a localization device, the wire may be a single- or multiple-piece element adapted to form, upon deployment within tissue of a human patient, a generally straight proximal portion having a longitudinal axis and a curved distal anchoring portion defining a central axis. The central axis should be substantially aligned with the proximal portion longitudinal axis when so deployed. The wire distal anchoring portion may generally assume a curvilinear configuration extending approximately 360 degrees.

Alternatively, when used as a tissue localization device, the unitary or multiple piece wire may be adapted to form, upon deployment within tissue of a human patient, a generally straight proximal portion and a curved distal anchoring portion having a cross-section with a major axis and a minor axis and wherein the major axis is equal to or greater in length than the minor axis. The wire distal anchoring portion may generally assume a curvilinear configuration extending approximately at least 360 degrees. It may further define a central axis that is substantially aligned with the longitudinal axis of the proximal portion.

Still a further tissue localization device is disclosed which consists of a unitary or multiple-piece wire having a shoulder and optional tabs. The wire is adapted to form, upon deployment within tissue of a human patient, a generally straight proximal portion and a curved distal anchoring portion. The wire may have a non-circular cross-section.

The tissue localization device or wire may be combined with other components described herein to form a tissue localization device deployment assembly, which includes a tissue localization wire deployment tube defining a deployment tube lumen, a wire stiffening tube disposable within the deployment tube lumen, and a unitary or multiple-piece tissue localization wire disposable through the stiffening tube lumen. The wire is adapted to form, upon deployment within tissue of a human patient, a generally straight proximal portion and a curved distal anchoring portion having a noncircular cross-section. The wire distal anchoring portion may generally assume a curvilinear configuration extending approximately at least 360 degrees. It may further define a central axis that is substantially aligned with the longitudinal axis of the proximal portion.

The stiffening tube in this assembly defines a stiffening tube lumen and comprises a wire lock, such as a screw reversibly extending through the tube wall, so that the stiffening tube and proximal portion of the wire may be advanced as a single unit into tissue.

An optional shoulder may be disposed on the localization wire, preferably but not necessarily at the junction of the wire proximal and distal portions or proximal to the distal portion. This assembly may also have a deployment tube lumen that is adapted for delivering fluid to the tissue via a hub and port in fluid communication with the tube lumen.

A further alternative tissue localization assembly is within the scope of the invention. This assembly consists of a tissue localization wire deployment tube defining a deployment tube lumen, a wire stiffening tube disposable within the deployment tube lumen, and a tissue localization wire. The wire is adapted to form, upon deployment within tissue such as a lesion, a generally straight proximal portion having a longitudinal axis and a curved distal anchoring portion having a noncircular cross section and a central axis that is substantially aligned with the proximal portion longitudinal axis. The stiffening tube defines a stiffening tube lumen and a wire lock so that the stiffening tube and proximal portion of the wire may be advanced as a single unit into tissue.

BRIEF DESCRIPTION OF THE DRAWINGS

FIG. 1A depicts a prior art wire localization technique.

FIG. 1B depicts a further prior art wire localization technique.

FIG. 2 shows a tissue localization system according to the present invention.

FIG. 3A shows one embodiment of a tissue locating element according to the present invention.

FIG. 3B shows the tissue locating element of FIG. 3A together with a deployment tube and pusher assembly tube.

FIG. 3C shows another embodiment of a tissue locating element according to the present invention that is connected to an external energy source.

FIG. 3D is a cross-sectional view of the tissue locating element of FIG. 3C.

FIG. 3E is yet another embodiment of a tissue locating element according to the present invention connected to a flexible wire or suture.

FIGS. 3F–3J show various alternative shoulder configurations for a tissue locating element of the present invention.

FIGS. 3K–3N show various shapes for a tissue locating element of the present invention.

FIGS. 3O and 3P show tissue locating elements according to the present invention having strain relief features.

FIGS. 4A–4F show various views of a deployment tube and attached orientation element according to the present invention.

FIGS. 5A–5C show various views of a tissue cutting element of the present invention disposed in a cannula for making an initial incision into tissue prior to deployment of the tissue locator element, complete with optional syringe and hub.

FIG. 6 shows an electrosurgical tool variation of a tissue cutting element of the present invention.

FIGS. 7A–7C and 8 show two embodiments of a tissue pusher assembly of the present invention.

FIG. 9 shows breast tissue containing a lesion and surrounding tissue volume placed between two compression paddles.

FIG. 10 shows the breast tissue and lesion of FIG. 9 penetrated by a blade extending distally from a cannula.

FIG. 11 shows the breast tissue and lesion of FIG. 9 with the blade removed and a trocar advanced into the tissue through the cannula to open up a pathway for accessing the lesion.

FIG. 12 shows the breast tissue and lesion of FIG. 9 with the trocar removed and a deployment tube and orientation element deployed in the cannula.

FIG. 13 shows the breast tissue and lesion of FIG. 9 with a locator element being advanced distally into the tissue by a pusher.

FIG. 14 shows the apparatus of FIG. 13 with the locator element advancing along a border of the tissue volume containing the lesion.

FIG. 15 shows the apparatus of FIG. 13 with the locator element continuing its advance along a border of the tissue volume containing the lesion to enclose a distal portion of the tissue volume.

FIG. 16 shows the apparatus of FIG. 13 with the locator element substantially deployed along a majority of a border of the tissue volume containing the lesion.

FIG. 17 shows the apparatus of FIG. 13 with an additional locator element partially deployed along a second path defining a border of the tissue volume containing the lesion at an angle to the first locator element.

FIG. 18 is a top view of the apparatus of FIG. 17 with the second locator element fully deployed.

FIG. 19 is a perspective view of the apparatus of FIG. 17 with the second locator element fully deployed, demonstrating a polar deployment configuration.

FIG. 20A shows various paths the surgeon may take to excise the tissue volume substantially bounded but preferably not penetrated by the locator elements.

FIG. 20B–20E show stiffening tubes and grasper tools according to the present invention.

FIGS. 21A–21B show a perspective and top view, respectively, of a locator element of the present invention deployed in a tangential configuration.

FIGS. 22A–22B show a perspective and top view, respectively, of two locator elements of the present invention deployed in a tangential configuration.

FIG. 23 shows two locator elements of the present invention connected to a source of energy.

FIGS. 23A–23B show an alternative use for a tangentially deployed locator element.

FIGS. 24A–24B show a method for redeploying a tissue locating element into tissue for reexcision according to the present invention.

FIGS. 25A–25G and 26A–26B show techniques for guiding the initial deployment of the locator element according to the present invention.

FIGS. 27A–27D show a cold-forming process for shaping and deploying a locator element of the present invention with a deployment tube having a die.

FIG. 28 shows another embodiment of a cold-forming die according to the present invention.

FIG. 29 shows yet another embodiment of an adjustable cold-forming die according to the present invention having reverse and positive die cavity curves.

FIG. 30 is a perspective view of a further embodiment of a cold-forming locating element deployment device according to the present invention.

FIGS. 31–33B show rotatable tissue locating element variations according to the present invention.

FIG. 34 is a perspective view of a tissue locating element proximal end pouch according to the present invention.

FIG. 35 is a perspective view of an offset fixture according to the present invention.

FIGS. 36A–36B depict alternative embodiments of a tissue localization wire assembly of the present invention.

FIG. 37 shows the assembly of FIG. 36A with an optional hub and fluid delivery port.

FIGS. 38–42 show the sequential deployment of a tissue localization wire of FIG. 36A to penetrate at least a portion of tissue, such as a lesion, in accordance with the present invention.

DETAILED DESCRIPTION OF THE INVENTION

The invention described herein is appropriate for a wide range of applications for marking a specific volume of tissue for excision or other purposes. Although the description below is largely in the context of marking a nonpalpable lesion in breast tissue and its subsequent excision, the invention is not so limited. For instance, the invention described herein may be used to mark tissue in a variety of locations in the body, such as the liver, the lungs, muscle tissue, or other tissue or organs where the advantages of the invention may be realized. It may also be used to mark a foreign object in tissue or body cavities as well, such as a bullet or the like. Accordingly, the invention and method for its use as described and claimed below is not limited to the marking and removal of lesions from breast tissue.

FIGS. 1A and 1B depict the current state-of-the-art tissue location methodology and equipment for nonpalpable breast lesions. In particular, FIG. 1A depicts a cross-section of breast tissue 10 having the lesion 20 to be marked for later removal disposed between two compression paddles 30 (shown in cross-section). A window 50 lies in the upper paddle 30 for accessing the lesion, which is surrounded by tissue volume 22. A localization wire 40 is shown placed in the lesion. The wire 40 depicted herein is "J"-shaped, and it may have a barb or hook on its distal tip to assist in anchoring the wire 40 in the breast tissue 10.

Note that in FIG. 1A, breast tissue 10 contains a typically nonpalpable lesion 20 or suspect tissue that is targeted for removal. Lesion 20 may contain precancerous or cancerous cells or it may contain one or more microcalcifications, which are often precursors to metastatic cell growth. Microcalcifications typically appear in clusters.

When removing these lesions 20, a primary concern is that a large enough volume 22 of tissue is removed so that all of the suspect tissue is enclosed therein. The border or perimeter of this volume 22, when properly sized, is colloquially called a "clean margin". If the pathologist finds suspect tissue on or near the border of volume 22, a "dirty margin" is present and additional tissue must be removed from the body along the previous tissue volume border until the pathologist is comfortable that all the suspect tissue has been removed. It is generally the goal, then, to remove the volume 22 of tissue completely containing within its borders the suspect tissue or lesion 20.

A radiologist performs this procedure under local anesthesia, typically under x-ray guidance. In the following discussion, we assume the wire localization technique shown in FIGS. 1A and 1B as well as the method of the present invention is performed under stereotactic x-ray guidance.

Normally the breast 10 containing the lesion 20 to be removed is placed between two compression paddles 30 to stabilize it for imaging and placement of wire 40. Identification of the lesion 20 under this technique is based on measurements of the position of the lesion on two images of the breast taken from different angles (typically +15 degrees and −15 degrees), called a stereo pair. The lesion is preferably centered below window 50.

Next, a computer maps the breast tissue by generating a set of coordinates corresponding to the targeted lesion 20 and a portion of the tissue 10 surrounding the lesion. Under stereotactic x-ray guidance, coordinates are generated in three dimensions (x, y and z). The z coordinate typically denotes to the depth of the lesion from the skin in a direction perpendicular to the surfaces of paddles 30, while the x and y coordinates define a horizontal plane parallel to the plates 30. This mapping procedure pinpoints the location of the lesion 20 as defined by the radiologist. The paddles are adjusted so that lesion 20 is centered in the x-y plane below window 50 along a vertical (or z) axis.

A small needle is next inserted into the tissue through window 50 in the upper compression plate 30 and moved towards the suspect tissue. This needle (not shown) acts as a deployment tube for localization wire 40.

The radiologist then passes localization wire 40 through the needle so that the distal end 60 is positioned in or adjacent lesion 20. Typically, wire 40 will have a barbed or hooked distal end 60 or may take on a "J" shape as shown in FIG. 1A.

A follow-up x-ray is taken of the lesion with wire 40 in place, and the radiologist will mark the x-ray image to indicate the location of lesion 20.

The radiologist next decompresses the tissue and transfers the patient to surgery for removal of lesion 20. It should be clear from this discussion that it is difficult at best to accurately determine the proper depth (along the z-axis) to which the surgeon should cut to safely and satisfactorily excise the lesion.

FIG. 1B shows a less common technique in which a second wire 70 is used to mark the lesion 20. Here, the coordinates of the lesion are determined and the wires 40 and 70 are deployed on either side of the lesion, defining the margin along an x or y direction. The radiologist then marks the approximate lesion location on the x-ray as described before. The margins in the other two dimensions must again be approximated; the margins along the vertical or "z" axis are once again particularly difficult to determine with any degree of accuracy.

The technique shown in FIG. 1B, called "bracketing" or "goalposting", is often used in a second localization attempt when the radiologist was unsuccessful in marking the lesion in a prior attempt.

As previously described, these techniques require post-excision re-imaging (and often re-excision and re-imaging) to ensure that the entire lesion is removed before the wound is closed and the patient sent home.

Turning now to the present invention, FIG. 2 shows one embodiment of a tissue localization system 100 that overcomes the deficiencies of current systems and methods.

System 100 typically comprises the following subsystems or components: a tissue locator element 200, locator element deployment tube 300, a driver tube or cannula 400, locator element orientation element or clock wheel 500, tissue cutting element or blade 600, trocar 420, and pusher assembly 700.

System 100 is versatile. For instance, a stereotactic guide unit 80 may be connected to the driver tube 400 or some other component as shown in FIGS. 7–9. Guide unit 80 interfaces with a stereotactic x-ray system to guide system 100 to the proper coordinates as discussed above. System 100 may be delivered via a variety of imaging modalities, including a mammography unit (either freehand or under stereotactic assistance), on a stereotactic table, under ultrasound or magnetic resonance imaging guidance, etc.

System 100 may alternatively or additionally be connected to a device such as a Fischer Table to provide a stable platform from which the system is used to mark tissue under x-ray guidance. An alternative driver positioning member or clevis 820 may also be connected to a custom made vise or a commercially available driver, which in turn may be connected to a Fischer Table or other platform. This enables system 100 to be used with existing commercially available platforms and drivers, ensuring ease of use, low cost, and maximum versatility.

In general, after tissue 10 is mapped and centered between paddles 30, blade 600, which is slideably disposed in a lumen of driver tube or cannula 400, is deployed through a distal end of cannula 400 into the breast tissue to the vicinity of the volume of tissue containing the lesion to be removed.

Blade or cutting element 600 may contain one or more tubular portions along its length, each having a lumen through which lubricant or an anesthetic may be administered as is discussed later.

A proximal end of blade 600 may be disposed in a lumen of tubular pusher element 730, which is part of pusher assembly 700. As shown in FIG. 2, pusher assembly 700 may also include a clamping ferrule or similar element 710 having a lumen for slideably receiving a proximal portion of blade 600 and, more importantly, locator element 200. A thumbscrew or similar securing member 720 is provided to fix a proximal section of the blade or locator element within the pusher assembly ferrule 710. Pusher assembly 700 may also be affixed to the aforementioned platforms or drivers in a variety of configurations; the arrangement described herein is merely exemplary.

After advancing the cutting element 600 through the tissue 10 to reach the vicinity of the tissue volume of interest, the blade 600 is withdrawn and driver tube or cannula 400 together with trocar 420 are inserted into the proximity of tissue 10. Cannula 400 may follow trocar 420 or may advance into the tissue simultaneously with trocar 420. Preferably, driver tube 400 is advanced to the skin surface but does not penetrate (or just slightly penetrates) tissue 10. This further opens up a passageway, or port, in the tissue for deployment of additional components of system 100.

After the trocar reaches the desired location near the tissue volume, it is proximally withdrawn from driver tube 400, which is left in the tissue, and a preferably oval deployment or delivery tube 300 is inserted through the lumen of driver tube 400 so that its distal end is disposed in the region of the tissue volume to be excised.

The radiologist next advances a locator element 200, which is preferably radiopaque, through the distal end of the tube 300 lumen to penetrate tissue and occupy the tissue volume boundary. Locator element 200 is preferably designed to take on an arcuate or curvilinear shape when extended through the tube 300 distal end, such that as it penetrates tissue it follows a planar and preferably arcuate or curvilinear path to create a physical border around the majority of the perimeter of the targeted tissue volume, preferably without penetrating it. The locator element 200 is designed to remain fixedly yet removably in place once deployed in tissue 10 as will be described later in greater detail.

Delivery tube 300, driver tube 400, and any other component of system 100 may then be removed, leaving only the locator element fixedly in place in the targeted tissue. Preferably, but not necessarily, the locator element is long enough so that a reduced profile proximal end (or alternatively an attached suture or the like) extends proximally through the surface of the skin.

The patient may then either delay the excision procedure as desired or as dictated by the surgeon's schedule, or she may be transferred to surgery for excision of the marked volume.

During the excision process, the surgeon cuts along the wire or the proximal portion of the locator element 200, following it to the vicinity of the tissue volume. The surgeon excises the tissue volume without invading the volume interior by cutting around the surface of the locator element opposite the locator element surface directly adjacent the tissue volume. The surgeon may also access the locator element 200 by any number of approaches not necessarily along the proximal portion of element 200, such as circumareolarly or via some other more direct or cosmetically acceptable approach as she sees fit.

Alternatively, prior to removing the remaining components of system 100 from the tissue, one or more additional locator elements may be deployed through delivery tube 300 into the tissue at an angle with respect to and about a longitudinal axis of the first locator element. This may be accomplished by the use of a clock wheel or orientation element 500 that may be rotated to orient the locator element or elements to a predetermined angle. Once oriented, the additional locator element or elements are deployed into the tissue in the same manner as the first locator element. These additional elements further define the same tissue volume along a different but similar arcuate path. The particular angular orientation of each deployed locator element with respect to each other may be arranged (e.g., at forty-five or ninety degrees) so that the spatial orientation and location of the tissue volume border occupied by the locator elements may be determined under x-ray or other visualization technique with greater accuracy.

When the desired number of locator elements 200 have been deployed to define and substantially bound the tissue volume, the remaining components of system 100 may be removed and the tissue volume may be excised.

Each component of system 100 of the present invention as well as a detailed description of the various techniques for its use will now be described in detail.

Locator Element

FIGS. 3A–3J depict various embodiments of the locator element 200. In FIG. 3A, a particularly useful variation of element 200 is shown in perspective as having a straight and flat configuration as it assumes when disposed in the confines of a deployment tube 300 lumen.

A proximal portion 210 of locator element 200, preferably having a smaller cross-sectional area than a distal portion 220 of locator element, is shown. Proximal portion 210 transitions through a radius to distal portion 220 at shoulder 240. Preferably, the entire locator element 200 is a single-piece article having no joints or the like. When a single piece, the proximal portion 210 may be formed by laser or photoetching, traditional, electron-discharge or water-jet machining, cutting, or other techniques to reduce its cross-sectional area relative to distal portion 220. We have found that it is particularly desirable, both for manufacturing and for clinical performance, to start with a single wire made of nitinol, spring steel, or the like, and can have round or square or other cross-sectional configurations. The proximal portion 210 of the wire is ground to the desired diameter. The distal portion 220 is then cold rolled to flatten it. Alternatively, the distal portion can be hot rolled, hot or cold stamped, coined and the like. Then the distal tip 230 of the distal portion 220 is ground or otherwise modified to form a pointed tip and/or one or more edges 250, 260 may be sharpened as described below. A curve is then formed in proximal portion 210 as will be described later. In some cases, it may be desirable to heat treat the material following the rolling or stamping process and prior to forming the curve. The material may be partially stress relieved to make it less brittle to allow it to take the shape of the curve without breaking; in the case of nitinol, it is only partially annealed to a point at which it still maintains its superelastic properties. Alternatively, for some materials and configurations, the proximal portion 210 may be annealed without annealing the distal portion 220 to impart flexibility to only the proximal portion 210.

Alternatively, proximal portion 210 may be a separate article joined to distal portion 220 at shoulder 240 by any appropriate technique, such as soldering, welding, brazing, adhesives, or the like.

Whether the locator element 200 is a single piece or a separate proximal portion 210 joined to distal portion 220, and especially if it is a single piece, it may be desirable to include a strain relief, such as those shown in FIGS. 3O and 30P. The strain relief may be a simple taper 211 (FIG. 30O), or may be a taper into a serpentine or helical portion 213 (FIG. 30P). This strain relief helps to strengthen the transition from the usually larger, stiffer distal portion to the usually thinner, more flexible proximal portion. In the case where the distal portion is not substantially stiffer than the proximal portion, a serpentine or helical strain relief serves to decouple the two portions such that manipulating the proximal end protruding from the body will not substantially dislodge the distal portion or manipulate tissue within the distal portion.

We prefer proximal portion 210 and distal portion 220 to each have a similarly square or rectangular cross-sectional profile, but other profiles such as circular, elliptical, and irregular are also contemplated. The cross-sectional profile of proximal section 210 need not be the same as the cross-sectional profile of distal portion 220. Furthermore, while FIG. 3A shows only a width difference between proximal portion 210 and distal portion 220, these portions may also differ in thickness.

The smaller cross-sectional area of proximal portion 210 compared to the distal portion 220 (as well as any possible differences in material properties when these portions are made from dissimilar materials) reduces the flexural modulus of proximal portion 210 relative to distal portion 220. This affords greater flexibility or bendability to the device so to reduce the risk of locator element breakage, injury to others, and tissue trauma when proximal portion extends from the surface of the skin after locator element deployment but before excision. Preferably, proximal portion 210 is flexible enough to be freely and safely manipulated; for instance, proximal portion 210 may be taped or affixed to the patient's skin after deployment. This eliminates the need to have the tissue volume immediately excised, freeing the patient to leave and return for the excision at a later time. Not only does this help to decouple the radiologist from the surgeon, but also it gives the patient more flexibility to do as she pleases and certainly less invasive discomfort.

Shoulder 240, disposed either proximate the distal portion or at the transition of the proximal and distal portions of locator element 200 is a particularly useful optional feature. Shoulder 240 provides an engaging or abutting surface against which the radiologist or surgeon may advance the distal end of the pusher assembly 700 (see FIG. 3B) so to move locator element 200 out the distal end of deployment tube 300 and into the tissue. Furthermore, it provides a stop against the tissue to prevent locator element 200 from backing out accidentally. Enhancements to this "anchoring" feature of shoulder 240 are discussed below in conjunction with an embodiment of locator element 200 designed for use with a flexible wire, suture, or the like.

Distal portion 220 of locator element 200 is shown in FIGS. 3A and 3B as having a rectangular cross section and a distal end 230 that forms a blade or cutting surface. Alternatively or in addition, one or both of leading edge 250 or trailing edge 260 may form a blade or cutting surface. The particular shape of the distal end 230 and the cutting surface or surfaces are determined by the particular tissue in which the locator element 200 is designed to be placed and other clinical and practical parameters. The configuration of FIG.

3A is but one of many possible to provide the most efficient advancing surface for moving through tissue.

FIG. 3C shows an alternative configuration in which locating element 200 is connected to source of energy 265, preferably radio frequency (RF) energy, through lead 270. In this embodiment, RF source 265 may be a BOVIE (Bovie Medical Corp., Melville, N.Y.) unit or the like to deliver high frequency current to locating element 200. When so energized, the distal portion 220 of the locating element becomes an active electrode that can cut through and optionally cauterize tissue as is well known to those of skill in the art. RF may be used alone to cut through tissue or may be used in conjunction with mechanical cutting means to assist in advancing the distal portion 220 of locating element 200 through tissue.

Energy source 265 may provide other electrical energy forms to locator element 200, or it may also or instead be a source of mechanical, thermal, acoustic or other type of energy as may be desired.

When providing RF energy, source 265 not only aids in advancing the distal portion 220 into position around the tissue volume by cutting through the tissue, it may also be used to aid the surgeon in excising the tissue volume from the body of the patient, for instance, when the energized locator element 200 (or array of elements) is rotated through an angular displacement as will be discussed in greater detail.

In order to facilitate this rotational cutting action, distal portion 220 of locator element may incorporate a leading edge 250, a trailing edge 260, or both, as shown in FIG. 3C. These portions 250 and 260 preferably but not necessarily will have a sharpened profile so to provide a cutting surface for displacing tissue and providing a focus for the high frequency energy.

One particularly useful variation of this configuration is shown the FIG. 3D cross-section of a distal portion 220 of locator element 200 that may be used with RF energy. Here, an insulative coating or layer 280 covers the two opposing surfaces of the locator element 220 adjacent leading edge 250 and trailing edge 260. Such insulation 280 serves to electrically isolate the surfaces covered by the insulation and further focuses the RF energy on the leading and trailing edges. Insulation 280 may comprise a ceramic or metallic oxide (such as alumina, tantalum oxide, titanium oxide, etc.), a biocompatible polymer or any other suitable biocompatible electrically insulating material. Insulation 280 may be in the form of a coating that may be applied by well known deposition methods such as physical vapor deposition (including sputtering, evaporation, ion plating, ion beam-assisted deposition, ion implantation, etc.), diffusion (e.g., cementation), electrophoresis, anodizing, plating, chemical vapor deposition, pulsed laser deposition, painting, dipping, electroplating, laser surface processing, thermal spraying, etc. Insulation 280 may also be formed in situ via surface oxidation, etc. Insulation 280 may completely cover the opposing surfaces of distal portion 220 as shown in FIG. 3D; alternatively, insulation 280 may cover only portions of these surfaces or additionally cover portions of leading edge 250 and trailing edge 260. The amount of surface area covered by insulation 280, as well as the insulation thickness, compositional profile, density, and other properties may be tailored for the particular tissue and application in which the locating element 200 is designed to operate.

We prefer that insulative coating 280 has a low coefficient of friction to ease the movement of locator element through tissue. It is even contemplated that the locator element be coated with a noninsulative but low-friction coating, whether the device is used with RF or other energy or not, simply to achieve this goal.

FIG. 3E shows another variation of locating element 200 in which a flexible wire, cable, suture or the like 290 is attached to locating element via eyelet 292. As may be seen, the overall length of locating element 200 may be considerably shorter than other variations, as the cable 290 may be viewed as taking the place of locator element proximal section 210. A suture 290 is even more suitable than the proximal portion shown in FIG. 3A for presenting a flexible, safe, and effective "lead" that may extend out through the breast surface after the locator element has been placed in the tissue. Although not shown, the ends of the wire 290 may be twisted together so that they exit the body as a unit rather than as two separate wires. Additionally, wire 290 may be intentionally kinked in the region of eyelet 292 to help keep it in place.

Threading wire 290 through eyelet 292 is but one of a wide variety of ways to connect wire 290 to locator element 200. More than one eyelet may be present, for example, if it is desired to attach multiple sutures or other elements to locating element 200; alternatively, multiple sutures or other elements may be attached to locating element via a single eyelet 292. In addition, eyelet 292 or an equivalent attachment junction may be disposed distally of proximal end of locating element 200, either centrally or on one side thereof. It is further within the scope of the present invention to provide an attachment element (not shown) such as an adhesive strip, a crimp sleeve, a weld sleeve or the like, to secure wire 290 to locator element 200. This attachment element, or shoulder, may also function to anchor the locating element in the tissue, as further described below. If the attachment element is used in conjunction with the eyelet, the wire 290 may be threaded through the eyelet 292, then secured with a crimp sleeve or the like. One end of the wire may be cut off where it exits proximal of the crimp sleeve so that only one end of the wire will exit the body. Alternatively, both ends of the wire may be left in place for strength, and may optionally be twisted together, as described above.

As discussed above, we find it useful to incorporate an anchoring feature to the locator element 200 to provide enhanced traction when the element is deployed in tissue. The simple shoulder feature described above works well to accomplish this goal. Exemplary variations to this design are shown in FIGS. 3F–3I on a locator element 200 having eyelet 292; the variation of FIG. 3J shows an anchoring feature on a locator element without an eyelet; however, each of these variations may be used interchangeably both with and without eyelets.

The embodiment of FIG. 3F comprises a locator element 200 having a serpentine edge 222 on its proximal end. Two recessed apertures 244 create three tabs 246 that may be substantially aligned with the plane defined by locator element 200 as shown, or that may be oriented outside this plane to enhance the anchoring effect. For instance, the outer two tabs may be disposed at positive and negative angles, respectively, with respect to this plane as shown in FIG. 3G.

Regardless of the tab orientation, the increased surface area of the locator element 200 proximal end presented by this serpentine design and the portions of the surface 222 oriented other than 90 degrees with respect to the locator element plane increases frictional resistance with tissue, enhancing the anchoring effect.

An alternative double flange configuration for anchoring locator element 200 is shown in FIG. 3G. Here, tabs 246 are similar to the tabs in the FIG. 3F embodiment except that they are deflected in opposite directions with respect to central tab 246, which is generally aligned with the locator element plane. In addition, the tabs are longer, presenting even more locator element proximal end surface area for increased frictional resistance and anchoring in tissue.

FIG. 3H depicts yet another variation. Here, a single tab 246 is cut out of the proximal end of locator element 200 distal to eyelet 292. This variation depicts tab 246 as being disposed at an angle with respect to the locator element 200 plane so that when the locator element curves in tissue it faces outward as shown in FIG. 3H.

Additional variations are depicted in FIGS. 3H' and 3H". Tabs 246 of these variations are generally aligned with the locater element plane. In the variation of FIG. 3H', tabs 246 flare outwardly from the locator element to achieve a barb-like effect. In the variation of FIG. 3H", tabs 246 have outer edges that remain parallel to the edges of the locator element. These tabs or barbs are formed essentially by way of recesses extending into the locator element.

In FIG. 3I, a dual-tab configuration is shown on a locator element 200 with eyelet 292.

FIG. 3J depicts a variation in which locator element contains a proximal portion 210 as previously described; note the absence of any eyelet in this embodiment.

Note that in each of these embodiments, the tabs or flanges are designed to facilitate forward (distal) movement of the locator element into tissue 10 as described herein, while generally resisting movement in the lateral or reverse (proximal) directions. By virtue of their location on the distal end of the locator element, the tabs or flanges preferably will not engage tissue to resist reverse movement until the locator element is deployed to its desired permanent position. This ensures the reversibility of the locator element deployment up until the point at which the tabs or flanges deploy into tissue as well. As will be discussed later, there may be an indicator to signal when the tabs or flanges are about to deploy.

Other features may be used to variously tailor the effectiveness of the tabs or flanges. For instance, the depth of the tab cuts may be relatively shallow or deep, the angle of the tabs 246 relative to the locator element plane may be relatively small or large, etc. If locator element 200 comprises a shape memory material, the tabs or flanges 246 may be thermally activated to assume a relatively low or high angle profile with respect to axis 248 to tailor the anchoring effect as needed.

In addition, the tabs or flanges, especially those such as shown in FIGS. 3G, 3H, and 3J, may be designed so they are constrained or biased when located within the lumen 310 of deployment tube 300. As the locator element is deployed into tissue out of lumen 310, tabs 246 may "spring" out to extend outside a plane defined by the locator element, providing for an enhanced anchoring effect.

Shape memory materials, including spring steel (e.g. 17-7), superelastic alloys such as nickel-titanium, Ni—Co—Cr (e.g. ELGILOY (Elgiloy LP, Elgin, Ill.)), and superelastic polymers are excellent choices for the tabs or flanges so biased.

Each of the anchoring features discussed herein is exemplary of a large number of designs and configurations possible within the scope of this variation. For instance, the number of tabs, angular orientation of the flanges, and depth of cut may vary significantly from those examples discussed herein.

Locator element 200 is designed to assume a generally arcuate or curvilinear shape when unconstrained or when deployed in tissue. As such, we prefer that locator element 200 comprise a material having a shape memory, such as spring steel, stainless steel, nickel-titanium alloy such as nitinol, a shape memory polymer, or other such materials. It is preferred that locator element 200 be nickel-titanium, although less desirable alloys (from a toxicity standpoint) that exhibit shape memory characteristics, such as copper-zinc-aluminum, copper-aluminum-nickel, copper-zinc-silicon, copper-zinc-lead, gold-cadmium, and nickel-cadmium, are contemplated as well. These alloys may be coated or covered with a material to enhance biocompatibility. Both superelastic materials (i.e. temperature-independent) as well as temperature-dependent one- and two-way shape memory materials are contemplated for locator element 200. Such materials and their behavior are described in U.S. Pat. Nos. 3,174,851, 3,351,463, 3,753,700, 4,665,906, 5,067,957, and 5,190,546; the entirety of each is hereby incorporated by reference.

The particular degree of curvature and shape of locator element 200 when unconstrained or constrained only by tissue may be designed into the element for a variety of tailored applications as is well known in the art. It is within the scope of this invention, for instance, to supply a kit to the radiologist having a variety of locator elements with differing loop diameters and perhaps differing shapes from which to choose. A template or similar instrument that may be held up to an x-ray of the tissue containing the lesion 20 and surrounding tissue volume 22 may be provided as well. This would allow the radiologist to accurately select the proper locator element for deployment into the particular tissue of interest.

Locator element may be mechanically straightened to assume a first generally linear or flat configuration as it is inserted into deployment or delivery tube 300 or equivalent constraining member. As the distal end of the locator element 200 is deployed beyond the distal end of delivery tube 300 into the tissue of interest by pusher assembly 700, locator element 200 naturally assumes a second, substantially arcuate or curvilinear profile discussed above as it penetrates tissue and defines a tissue border along a path. The tissue border defines a tissue volume containing the targeted lesion that is to be excised. Preferably, locator element 200 does not penetrate the tissue volume as it is deployed. This shape transformation described above is preferably entirely temperature-independent; that is, it may take place at a single temperature simply upon removing the physical or mechanical constraint of tube 300 or the like as it deploys into tissue or a cavity. However, we contemplate that materials exhibiting temperature-dependent transformation properties; e.g., those that can be engineered to transform from a flat, planar shape into an arcuate or curvilinear shape upon reaching a temperature threshold (such as body temperature), may be used for the locator element as well.

The particular arcuate or curvilinear shape discussed above may widely vary depending upon a variety of factors; e.g., the type of tissue the locator element 200 is designed to mark, the size and location of the tissue volume, the deployment configuration (i.e., polar, tangential, etc. as will be discussed later), and other factors. Locator element may also assume more complex shapes having more than a single curve or even curves that change direction.

We have found that a given locator element 200 will often assume different deployed shapes depending upon the medium into which it is deployed. Further, we have found that these differences are predictable. For instance, a nitinol locator element deployed into ambient air may take on a circular deployed shape having a diameter of one inch.

However, when that same locator element is deployed into breast tissue, its diameter increases to a somewhat larger size; e.g., 1.125 inches. Although this phenomenon is not completely understood, we believe it is influenced by the constraining effect of the tissue surrounding the locator element and the increased force required to advance the same into the tissue. Such a phenomenon may be affected by a number of parameters, including the medium into which the locator element is deployed (e.g., breast tissue, lung tissue, liquid, air, etc.), the material comprising the locator element (e.g., nitinol, stainless steel, etc.), the intended deployed shape of the locator element (e.g., circular, elliptical, serpentine, etc.), the dimensions of the locator element, temperature, the presence of additional locator elements in the tissue, polar vs. tangential deployment, etc.

It is within the scope of this invention to gather data regarding this phenomenon, assemble them into a useable format such as a computer database, and develop empirical and theoretical models to predict this shape change and to aid in the design and use of a given locator element for ensuring the desired outcome in tissue for a given clinical need.

For example, a physician may desire that a given nitinol locator element deployed in tangential fashion into breast tissue take on an elliptical shape having major and minor axes of 1.25 inches and 1 inch, respectively. Knowledge of such an element's deployment shape in air under a given set of conditions allows us to generate design information to aid the engineer in producing a locator element having these desired dimensions when deployed in breast tissue.

We prefer that as the wire distal portion 220 is being deployed, the wire distal tip 230 extend at least approximately 360 degrees, as shown in FIG. 3K. Distal tip 230 may even extend beyond 360 degrees if desired. This affords the surgeon a degree of protection from what may otherwise be an exposed sharp distal tip 230. Furthermore, the typically larger distal portion 220 may extend at its proximal end at a tangent or perpendicular to the typical ring formed by the rest of the distal portion, as shown in FIGS. 3L and 3M. Additionally or alternatively, as shown in FIG. 3N, distal tip 230 may even extend more than 720 degrees to form two complete loops in contact with each other. This has the advantage of allowing the width and/or thickness of locator element 200 to be smaller, yet still provide sufficient anchoring effect for surgical removal.

We also prefer that locator element 200 be at least partially radiopaque so that it may be readily viewed under x-ray energy. This aids the radiologist in placing locator element 200 in the desired tissue position as well as allowing for verification of its location and orientation. Locator element may be radiopaque by virtue of its inherent material properties; i.e., nitinol exhibits both a shape memory effect and some radiopacity as well, making it a suitable material for use in the locator element. The radiopacity of locator element 200 may be enhanced by adding a variety of components comprising materials exhibiting greater radiopacity, such as bands or elements made from platinum, palladium, tungsten, gold, silver, etc., that may be bonded or otherwise affixed to locator element 200 in predetermined locations (such as, e.g., along the leading edge 250 and trailing edge 260 or on the distal end of locator element 200). If locator element distal section 200 is insulated, such insulation may be radiopaque as well. For instance, polytetrafluoroethylene doped with barium sulfate or some other appropriate radiopaque material is suitable for this purpose.

For viewing under ultrasound, the echogenicity of the locator element can be enhanced by, e.g., increasing the effective surface area of the element through techniques such as microblasting the locator element or adding a microporous coating to the element.

As shown in the various figures, the distal portion 220 of locator element 200 preferably comprises a ribbon having a rectangular cross section. Such a shape provides a surface against which the surgeon may cut when excising the tissue volume contained by the locator element. In addition, when the distal portion 220 is radiopaque, the orientation of the locator element may be readily determined under x-ray visualization depending upon which surface (i.e. a leading or trailing edge as opposed to a wider surface) is presented to the viewer. Even if the deployed locator element 200 occupies multiple planes in the tissue with respect to the x-ray or ultrasound source, such information should be readily visible due to the asymmetric shape of ribbon locator element 200. A ribbon shape also most readily facilitates movement around tissue volume 22 as the path is defined, particularly in the distalmost portion of the path or border 24.

Although we prefer that the shape of distal portion 220 be a ribbon as described above, it is not so limited. For instance, the distal portion 220 may have a circular, elliptical, oval, or irregular cross-sectional shape. Various rectangular cross-sectional shapes ranging from square to those having higher cross-sectional aspect ratios (i.e., a ribbon) are contemplated as well.

When in the shape of a ribbon, distal portion 220 of locator element 200, including the shoulder portion, may be between about 1.0 mm and 7.0 mm wide and between about 0.2 mm and 1.0 mm thick; we prefer it to be between about 2.0 mm and 5.0 mm wide and about 0.5 mm and 0.8 mm thick. Other cross-sectional shapes preferably are on the order of the same dimensions as those recited above. We have found that a ribbon width of about 1.5 mm (about 0.060 inch) is particularly desirable. This width provides the optimum balance of properties (e.g., manipulability, anchorability, and palpability) during and after deployment around tissue volume 22.

If a shoulder portion 240 is present, it may transition from the ribbon portion having a rectangular cross section to a proximal portion 210 having a generally square or rectangular cross section with a thickness preferably the same as that of distal portion 220 and a width on the order of approximately 30 percent to approximately 80 percent of the width of distal portion 220. The particular ratio of the widths of proximal portion 210 to distal portion 220 will depend on the design constraints associated with the particular application for which system 100 is chosen. The cross-sectional shape of proximal portion 210 does not have to be the same as that of distal portion 220.

Further aspects of locator element 200 and its operation in conjunction with the other components of system 100 are discussed below in greater detail.

Locator Element Delivery Tube and Orientation Element

Turning now to FIGS. 4A–4E, oval deployment or delivery tube 300 is shown with orientation element or clock wheel 500.

Deployment tube 300 is the primary device through which locator element 200 is delivered to the targeted tissue volume perimeter. The particular design elements of tube are not critical to the operation of the invention; as long as it effectively aids in delivering locator element 200 to the proper location, deviations from the features described herein and shown in the figures are possible.

Delivery tube 300 preferably has a lumen 310 that has a generally oval cross-sectional shape to accommodate the rectangular cross-sectional shape of locator element 200 and to present a lower profile when penetrating tissue. This ensures proper deployment of locator element 200 in the desired position and angular orientation. However, delivery tube lumen 310 may assume a variety of other cross sectional shapes, including circular, rectangular, irregular, etc. and may be further configured to house and deliver more than one locator element. In any event, we particularly prefer that delivery tube lumen 310 have cross-sectional dimensions sized so that the locator element 200 may freely axially or slideably move therein; in addition, free or limited rotational movement of locator element 200 therein is also contemplated.

We prefer tube 300 be a stainless steel hypotube or the like, although it may comprise a polymer, nickel-titanium, a composite material, or other metals such as platinum, tungsten, cobalt, titanium and their alloys.

A proximal section 310 of tube 300 terminates at interface 330 with an orientation element or clock wheel 500 as shown in FIGS. 4A and 4B. Interface 330 may be a simple recessed interference fit or other type of joint between the proximal end 310 of tube 300 and wheel 500. Interface 330 need not be permanent; proximal section 310 may be removably inserted into orientation element 500, locked in place, and removed so that another tube 300 (perhaps with a different cross-sectional shape) fits therein. Alternatively, orientation element 500 and delivery tube 300 may be integrally formed as a single unit so that interface 330 is simply a transition between the two.

In a preferred construction, orientation element 500 has a flange 510 bounded by serrations 520 to facilitate gripping and rotation as described below.

Another particularly useful and optional feature of clock wheel 500 is shown in FIG. 4C. Here, flange 510 has a straight or flat edge 530 to indicate to the radiologist the particular angular orientation of tube 300 selected. For instance, system 100 may be configured so that when the flat section 530 is aligned with stereotactic guide unit 80 (see FIGS. 7–9), the radiologist knows that the major axis of oval deployment tube 300, and in turn the major axis along the width of locator element 200, is aligned with the particular axis indicated by guide unit 80.

To further assist the radiologist in properly orienting deployment tube 300 and locator element 200, flange 510 may have an additional flat surface parallel to surface 530 on the opposite side of flange 510. In addition, wheel 500 may contain notches, raised sections, alphanumeric markings, electronic indicators (audible, visual, etc.), or combinations of these and other features to indicate the angular orientation of element 500 with respect to the tissue coordinate system. Any device that indicates to the user the spatial orientation of tube 300 and in turn locator element 200 is within the scope of this present invention. Orientation element 500 may be metallic or polymeric as dictated by design and functional considerations.

A useful variation of deployment tube 300 that may be used in any of the embodiments disclosed herein is shown in FIGS. 4D–4E. Here, a sharpened distal tip 322 facilitates safe and reliable entry into tissue during the locator element deployment procedure. It may be used to penetrate tissue in advance of deploying the locator element, or it may be used in conjunction with the cutting element 600 and cannula or driver tube 400 described below.

The design of tip 322 is particularly useful. Distal facets 324 and 326 are seen as tapering to a distalmost point 328. Distal facets 324 and 326 preferably comprise sharpened leading edges 325 and 327 for more readily cutting through tissue. Proximal facets 332 and 334 on the upper portion of the tube distal tip 322 may also be sharpened to formed sharpened trailing edges 336 and 337 as shown.

We have found that a particularly useful way to achieve the distal tip 322 of FIGS. 4D and 4E is by fabricating deployment tube 300, or at least the distal portion 322, of stainless steel hypodermic needle, hypotube, or the like. To form the sharpened edge, a portion of the hypodermic needle (which typically has a round cross-section) is cut off to form an acute angle, preferably between about ten and forty-five degrees, and even more preferably between about twelve and eighteen degrees, between the trailing edges 332 and 334 and a central axis of the deployment tube. Next, the leading edges are faceted into curved surfaces terminating at a sharpened tip 328. Any of the edges are sharpened as desired, and the entire tube is pressed so its cross-section becomes generally oval or elliptical in shape as seen in FIG. 4E.

Off-the-shelf "pointed cannulae", such as those sold by Popper and Sons, Inc. (New Milford, Conn.), may also be useful in achieving the desired distal tip 322.

Of course, the foregoing explanation is merely exemplary; any number of distal tip 322 designs as well as the particular steps and order of those steps for their fabrication are within the scope of the invention.

The particular design of tip 322 shown in FIGS. 4D and 4E is not only useful for cutting through tissue but also for dilating tissue prior to the advancement of locator element 200. Although we do not wish to be bound by theory, we believe that the curvature of faceted leading edges 324 and 326 helps to facilitate cutting through and dilating tissue as described herein.

In the variation depicted in FIG. 4F, delivery tube 300 is configured to contain lumen 310 that comprises two oval shaped portions extending at a right angle to one another. In this configuration, the delivery tube can house and deliver two separate locator elements 200, with each element being initially delivered along path at right angles to one another. As will be readily appreciated, the tube can be also configured to provide for delivery of two or more locator elements at a variety of angles relative to one another. Delivery tubes having these characteristics can further be provided with edged or sharpened distal tips, as in the embodiment of FIGS. 4D and 4E, to more readily cut through tissue. Where such sharpened tips are provided, it is most convenient to taper the tube to a distal most point that coincides with the intersection of the various lumen portions that are configured to house individual locator elements.

This variation also facilitates delivery of separate locator elements without the need of a fixed or mounted delivery device, such as described further herein. For example, a delivery tube according to this variation can be incorporated into a handheld delivery device. Further, such a handheld device can be used to serially deploy locator elements within tissue, without requiring the steps of removal and repositioning of the delivery tube within the tissue.

Cutting Element and Driver Tube

Turning now to FIGS. 5A–5C, cutting element or blade 600 is shown partially slideably disposed in a lumen of driver tube 400. As previously discussed, blade 600 is designed for deployment through driver tube 400 to initially penetrate tissue and create an access pathway through which delivery tube 300 and eventually one or more locator elements 200 may be deployed.

Driver tube or cannula 400 is preferably oval in cross-section to present a low profile configuration (as shown in FIG. 2), although it may have a more round cross-section (as shown in FIGS. 5A and 5C) or a cross-section that conforms to the cross-sectional profile of blade 600, especially the blade distal region 620 as discussed below. In general, any cross-sectional shape for cannula 400 suitable for deploying cutting element 600, deployment tube 300, and locator element 200 is within the scope of the invention.

We particularly prefer that the lumen of driver tube 400 be sized so that the deployment tube 300 may freely axially or slideably move therein; in addition, free or limited rotational movement of delivery tube 300 therein is also contemplated.

We prefer cannula 400 be a stainless steel hypotube or the like, although it may comprise a polymer, nickel-titanium, a composite material, or other metals such as platinum, tungsten, cobalt, titanium and their alloys.

Blade 600 may take on a wide variety of shapes, cutting surface configurations, and features depending upon the particular design and functional constraints for the application chosen. FIGS. 5A–5C, however, show a particularly useful blade design for making an initial incision into breast tissue to create an access passageway for deploying one or more locator elements as described herein.

Cutting element 600 has a proximal region 610 terminating at proximal end 630 and a distal region 620 terminating at a distal end 640. In this particular configuration, distal region 620 contains blade edges 650 and the distal end 680 of tubular members or lumen 660 disposed along the length of blade 600. Tubular member 660 may be considered an integral part of blade 600. FIG. 5A shows one of two tubular members 660 that are better seen in cross-section of FIG. 5B. As one moves proximally along blade 600, this dual-lumen cross-sectional profile gradually transitions into one having a single lumen as is shown in FIG. 5C. Cutting element 600 terminates, in this particular embodiment, in a hub 690 which attaches to an optional syringe 692.

Turning back to the distal end 640, two blade edges 650 are seen disposed along a single axis and joining at a single point near the distal end of blade 600. Blade edges 650 may take on a number of different configurations. They may be serrated, for example, and they may be capable of using electrical, acoustic, mechanical, or thermal energy as described herein and in greater detail below. Although the particular tip features and configuration of blade edges 650 may vary considerably and be within the scope of the invention, we have found the configuration of FIGS. 5A–5C to be particularly useful for cutting through breast tissue.

Cutting element 600 is designed to alleviate some of the difficulties associated with penetrating tissue by providing a port or lumen 660 through which various agents may be administered to the patient, preferably but not necessarily while the blade is cutting through tissue. For instance, an anesthetic agent such as lidocaine gel or liquid or the like may be selectively administered to tissue through the distal end 680 of tubular member lumen 660 via a syringe 692 connected to the blade 600 at hub 690. In addition, a lubricant such as K-Y jelly (Johnson & Johnson, New Brunswick, N.J.) or liquid, a water-based lubricant, or the like, may be administered during the cutting process to reduce the coefficient of friction between the blade edges 650 and tissue as the blade 600 cuts through the tissue. Other substances may be disposed through tubular member 660 as required, such as anti-thrombolytic agents, hormones, chemotherapeutic drugs, anti-scarring agents, etc. These and other substances may be administered manually by the radiologist during the procedure intermittently or continuously, or they may be automatically dispensed by any number of electronic, mechanical, or electromechanical means.

In addition, physical elements such as additional blades, individual hypotubes, fiber optics, sensors, and other devices may be deployed through lumen 660 as the radiologist or surgeon sees fit.

Although FIGS. 5A–5C show only two tubular members 660, the invention is not so limited. Any number of tubular members may be used with this invention, from one to six or more, depending upon the needs of the patient and the objective of the procedure in which blade 600 is being used.

Blade 600 and tubular member 660 may be metallic, polymeric, a composite material, or a combination of metals, polymers, and their alloys as described herein. Particularly useful is stainless steel. The various components of this variation of cutting element or blade 600 may be integrally formed as a single element, or they may be assembled via any number of a suitable joining techniques, such as welding, brazing, soldering, adhesives, or the like.

We prefer that blade edges 650 be hardened stainless steel so to provide a keener cutting surface that does not dull with use.

A valve and seal system as is well known in the art may accompany hub 690 to facilitate selective administration of the desired agent.

Tubular member 660 is optional. However, its low profile and functional utility for both patient and doctor make it a clearly useful feature that effectively complements system 100.

An alternative blade is shown in FIG. 6 as a conventional electrosurgery tool. Here, blade 602 comprises a standard electrosurgical pencil unit as is well known to those of skill in the art. Units and accessories such as those sold by Aaron Medical Industries, Inc. (St. Petersburg, Fla.) are suitable for this purpose.

Electrocautery pencil base unit 604 having a standard control switch 606 is attached to a power cord 608 and three-prong connector 609. We find it useful to employ an off-the-shelf extended tip 612 having a standard 0.24 cm diameter proximal end 616 and a shaft 614 with the appropriate length to reach the tissue 10 as described herein. We prefer that the shaft length be between about 2 cm and 15 cm; more preferably between about 4 cm and 12 cm.

An active electrode 618 is disposed on a distal end of tip 612 for delivering cutting and cauterizing energy to tissue. An alternative electrode 622 having a more tapered profile may be used to more readily facilitate penetration into tissue 10 and create the needed passageway for deploying locator element 200. As described with respect to the locator element of FIG. 3D, an insulative coating may again be employed on the blade electrode 618 or 622.

Pusher Assembly Embodiments

Turning now to FIGS. 7A–7C and 8, two tissue locator element pusher assembly variations of the present invention are shown. These variations, which are but two of many possible, achieve the objectives of providing a simple, safe, repeatable and reliable locator element deployment into the tissue of interest.

FIGS. 7A–7C show a pusher assembly 700 comprising a housing 702 attached to deployment or delivery tube 300 and slidably containing at least a portion of a pusher tube 730 and locator element 200 therein. A ferrule 710 having two adjustable fasteners 720 and a central channel or lumen 712 for receiving the proximal end of locator element is also shown.

Housing 702 preferably is comprised of a structural polymeric material, a metal or metallic alloy, or any combination thereof. Although housing 702 is shown in FIG. 7A as having an elongated tubular shape, it not need be so. Housing 702, for instance, may have a rectangular, oval, asymmetric, etc., cross section.

Housing 702 is preferably at least partially hollow such that it contains a central housing lumen 708 throughout at least a portion of its length from housing proximal end 704 to housing distal end 706. Lumen 708 should be large enough to slidably accommodate pusher 730 and ferrule 710 as will be described in greater detail later.

In communication with housing lumen 708 is at least one, and preferably two, longitudinal slots 709 as shown in FIGS. 7A and 7B. Slot 709 extends for at least a portion of the length of housing 702, and we prefer that it extend through a majority of the housing 702 (although it not need do so). Longitudinal slot or slots 709 form channels for accommodating adjustable fasteners 720 or a control lever; these are optionally attached to ferrule 710 and/or pusher 730 for axially advancing and retracting a slidably disposable pusher 730 and locator element 200 through housing lumen 708.

At housing distal end 706, the embodiment of FIGS. 7A and 7B may comprise a delivery or deployment tube 300 as described elsewhere herein. Tube 300 is preferably oval in cross section for accommodating a locator element 200 through a central lumen 310. Delivery tube 300 is in communication with the housing lumen 708 so that the tube lumen 310 may at least partially receive pusher 730 and locator element 200. Axial movement of pusher 730 and locator element 200 through this lumen 310 results in the deployment and retraction of locator element 200 through an aperture in tube distal end 368.

As described below in conjunction with an exemplary polar deployment of locator element 200 to locate a lesion of interest, pusher tube 730 is shown in FIGS. 7B–7C as comprising a main portion 732, preferably but not necessarily having a circular or square cross section, and a tube lumen 712 that slidably accommodates the proximal portion 210 of tissue locator element 200.

A perspective view of the transition between tube main portion 732 and ferrule 710 is seen in the view of FIG. 7C. Note tube central lumen 712 and tube proximal end 714 disposed on the proximal end of ferrule 710 for accommodating the locator element proximal portion 210, including any portion thereof that extends proximal of ferrule 710.

Adjustable fasteners 720 in the form of two thumbscrews may be screwed into apertures in ferrule 710. When locator element proximal portion 210 is disposed in pusher tube lumen 712, the user may slidably and adjustably fix the proximal portion 210 to the pusher between fasteners 720 so that the locator element 200 cannot axially move within pusher lumen 712. This allows advancement of both pusher tube 730 and locator element 200 together as a single unit. As will be apparent to those of ordinary skill in the art, the thumbscrews of FIGS. 7A–7C are but one of a number of equivalent fasteners 720 that may be used to adjustably fasten or fix locator element 200 to pusher tube 730. It is within the scope of this invention to accomplish this fastening without the use of ferrule 710 and in such a way that delivery tube 300 may be removed from the tissue and from pusher tube 730 while it is still attached to locator element 200.

A locator element 200, described in greater detail elsewhere, is shown in FIG. 7B is at least partially disposable in lumen 712 of pusher tube 730 such that its proximal portion 210 extends out of tube proximal end 714, through tube distal aperture 734. Locator element distal portion 220 is seen extending out the tube distal aperture 734 and assuming a preformed shape for marking tissue lesions. Note shoulder 240, disposed proximate the locator element distal portion 220, where it transitions to locator element proximal portion 210. This shoulder 240 serves as an abutting surface against which the distal end of pusher tube main portion 732 may rest Shoulder 240 also serves a number of purposes in tissue (with optional tab features) as described below in greater detail.

If the proximal portion 210 is replaced by a flexible cable, wire or suture as discussed below, the present pusher assembly may be used as described herein or in a modified form (for instance, with an alternative fastener 720) to accomplish the purposes of the invention.

To assemble pusher assembly 700, a locator element is loaded into pusher tube 730 such that its proximal portion 210 is loaded to the desired position. Abutting feature of shoulder 240 to the distal end of tube main portion 732 may be used as a reference to aid in determining the relative position of the locator element 200 when it is deploying in tissue. In the embodiment of FIGS. 7A–7C, the assembly of pusher tube 730 and locator element 200 is then loaded into the housing 702 through housing proximal end 704; adjustable fastener or fasteners 720 may then be inserted through housing slot or slots 709 and into ferrule 710 to affix locator element proximal portion 210 within pusher tube 730. Of course, this is but one of a number of ways to assemble the pusher assembly 700. Alternative assembly methods include inserting pusher tube 730 though the proximal end 704, then inserting the proximal end 210 of the locator element 200 through the pusher tube 730 distal aperture 734; and inserting the proximal end 210 of the locator element 200 through the distal end of delivery tube 300, then threading the proximal end 210 of the locator element 200 through the distal end of pusher tube 730 and inserting pusher tube 730 through the handle and delivery tube 300. One or more fasteners 720 may then be tightened to attach the pusher tube 730 to the locator element 200, with the proximal end 210 of the locator element preferably in tension.

In use, when the pusher assembly 700 is in position for marking the tissue lesion as described herein, the user advances the pusher tube 730 and locator element 200 via adjustable fasteners 720 (thus using them as handles) to axially advance them through the housing lumen 708 and deployment tube lumen 310 so that the locator element distal portion 220 extends out of tube distal aperture 368 as shown in FIG. 7A. The user may retract pusher tube 730 and locator element 200 as necessary so that distal portion 220 can be repositioned in tissue or prior to placement in the tissue.

A particularly useful feature of pusher assembly 700 is its versatility. For instance, a deployment fixture such as offset fixture 900 (described below) may be detachably affixed to housing 702, preferably but not necessarily at housing distal end 706, and either with or without deployment tube 300. For example, the offset fixture of FIG. 35 may comprise two oval deployment tubes extending from fixture body 940; these may be part of the fixture or they may be part of pusher assembly 700 and extending through fixture body 940 as desired.

Housing 702 may be affixed, preferably detachably, to a deployment fixture by means known to those of skill in the art. For instance, any number of secure and easily detachable joints or connectors, such as quick disconnect couplers sold by Colder Products Corp. (St. Paul, Minn.), are particularly effective. When connected to the pusher assembly 700, the deployment fixture preferably comprises at least one fixture lumen that is axially aligned with the pusher lumen 712 and the delivery tube lumen 310. This ensures that advancement of the pusher tube 730 in housing 702 will result in the intended reversible deployment of the locator element 200 into the targeted tissue region.

FIG. 8 shows an alternative variation of pusher assembly housing 702. This housing 702 has largely the same features as the embodiment of FIGS. 7A–7C and is shown without optional deployment tube 300. For instance, housing body 702 has a proximal end 704, a distal end 706, a housing lumen 708 and at least one longitudinal slot 709 disposed along one side of the housing body. A control lever 716 is shown partially disposed in slot 709 and extending outside housing 709 for access by a user. Lever 716 is affixed to a pusher tube (not shown) disposed in housing lumen 708 as described above. Lever 716 may be adjustably attached to pusher tube 730 so that it may aid in securing the proximal portion 210 of locator element 200 as described in conjunction with FIGS. 7A–7C. Lever 716 may also have a lever tab 718. A detent or notched mechanism 719 disposed near the distal end 706 of the FIG. 8 housing 702 is configured to cooperate with control lever 716 or the control lever tab 718 as the control lever (and attached pusher tube/locator element) is moved distally by a user along slot 709.

In this manner, control lever 716 and pusher tube/locator element may be moved in either the proximal or distal directions along slot 709 in the housing lumen 708 to advance the locator element into tissue and to retract the locator element if the user so desires. We prefer, however, that assembly 700 be configured so that as the user axially advances lever 716 distally to the point in which control lever 716 or lever tab 718 engages detent or notched mechanism 719, lever 716 is prohibited from moving proximally, thus "locking" pusher tube 730 and locator element 200 in place relative to housing 702.

The assembly of FIG. 8 may be configured so that when this locking mechanism is activated during use, the shoulder portion 240 of locator element 200 has penetrated into tissue a distance sufficient to anchor locator element 200 in the tissue, largely fixing the locator element 200 in place.

Thus, when the radiologist senses that lever tab 718 has engaged detent 719, she knows that locator element 200 is now anchored into tissue. In this manner, the lever tab 718 and detent 719 provides not only a feedback mechanism for the user to indicate that the locator element is now "locked" into place in the tissue, it also provides a safety function to prohibit the user from forcing the locator element 200 proximally once the shoulder 240 has engaged tissue (an action that may damage the tissue). This allows the user to safely and reversibly adjust the position of the locator element in the tissue as necessary until the desired alignment and deployment configuration is achieved, at which point the final configuration may be locked in.

The detent 719 may be biased to provide resistance upon initial contact with the lever tab 718 so that the user senses the distalmost limit of reversible axial motion in slot 709 immediately prior to engagement of detent 719. Other mechanical or electromechanical feedback mechanisms, including visual (e.g., colored lights) or audible (e.g., alarms), may be used to indicate this limit of reversible axial motion as well as the irreversible anchoring of the locator element 200 into tissue as described.

Note that the FIG. 8 device is shown without a deployment tube 300. As described above with respect to the FIGS. 7A–7C embodiment, a deployment fixture may detachably affix to the FIG. 8 housing 702, preferably at the distal end 709. In this manner, the pusher tube and locator element may be reversibly moved within the housing lumen 708 to extend through an aperture 721 of the housing lumen 708 and into an aligned deployment fixture lumen. Other features as described above with respect to FIGS. 7A–7C may also be used in the FIG. 8 assembly as desired.

Polar Deployment

FIGS. 9–20 show, in detailed fashion, a method for using system 100 to mark a volume of tissue for eventual removal or excision from the breast, preferably without penetrating or otherwise violating the interior of the tissue volume. A particularly useful technique in which one or more locator elements are deployed in a "polar" fashion is described below.

Although this method is described in the context of removing a nonpalpable lesion from the breast, it may be followed for marking and excising any tissue mass or foreign object from the body.

In particular, a method is described below for defining the border of a tissue volume to be excised from a patient. This is accomplished by deploying at least one locating element into breast tissue so that it follows a continuous path around the selected tissue volume, thereby containing the target tissue region. Later excision of the so-marked tissue volume by a surgeon is also described.

The patient is typically first prepared for the marking procedure by placing the breast tissue 10 between two compression paddles 30 on a platform such as a Fischer Table.

The tissue volume 22 containing the suspect lesion 20, such as one or more microcalcifications, is next mapped under x-ray guidance and a three-dimensional coordinate system or grid is assigned to the tissue of interest. Typically the entire breast tissue 10 between plates 30 is mapped on a three-dimensional coordinate system. For purposes of this example, "x" and "y" coordinates in FIG. 9 are associated with a tissue location along axes in a horizontal plane parallel to paddles 30. Likewise, the "z" coordinate describes a tissue location in a vertical or depth plane perpendicular to each of the x and y axes.

FIG. 10 shows portions of system 100 after lesion 20 and targeted tissue volume 22 have been identified, centered below window 50, mapped in three-dimensional coordinates, and driver tube 400 (shown in cutaway cross-section) with attached stereotactic guide unit 80 is centered over window 50. Blade 600 is disposed in a lumen of driver tube 400.

Note that a longitudinal axis of cannula 400 is generally aligned with a vertical or z-axis of the mapped tissue such that the cannula lumen is centered over tissue lesion 20. This configures system 100 so that locator element 200 deploys into the tissue 10 along this axis; hence the term "polar deployment".

Blade 600 is then deployed distally through the cannula 400 lumen so that it exits the cannula distal end and penetrates through tissue 10 to the targeted tissue volume 22 to be excised.

It is within the scope of the invention to perform this tissue penetration step in any number of ways. For instance, the radiologist may manually advance blade 600 into tissue 10, preferably with the assistance of x-ray, ultrasound, magnetic resonance, or other method. Such a technique may be preferable, especially under difficult or delicate conditions where caution and control are at a premium.

One particularly useful way to penetrate tissue is by way of alternative electrocautery pencil blade 602 described above in conjunction with FIG. 6. During use, blade 602 utilizes energy (such as RF energy) to assist the user in penetrating through tissue 10 and to create an access port for locator element 200.

This blade 602 is deployed into the cannula lumen in the same manner as blade 600 so that it exits the cannula distal end into the tissue 10 that is centered below window 50. Control switch 606 allows the user to apply cutting or coagulating energy, alone or in combination, to penetrate through this targeted tissue 10 to reach tissue volume 22.

Alternatively, blade 600 may be advanced automatically, such as via a spring-loaded or similar biopsy driver mechanism as is well known to those of skill in the art. In such a case, system 100 may be adapted to interface with any number of commercial biopsy driver systems through, for instance, an optional driver positioning or interface member. Pusher assembly 700 may also be used to advance blade 600 into tissue 10.

Typically, cutting element 600 will penetrate tissue 10 so that its distal end 640 just reaches the vicinity of the surface or border of tissue volume 22. In the case of a polar deployment scheme, blade distal end 640 will reach the border of tissue volume 22 along the z-axis as described above, while other deployment schemes may dictate deployment at other locations along or near the border of tissue volume 22.

Preferably, the blade 600 distal tip 640 does not penetrate into the tissue volume 22. If the tissue volume 22 is inadvertently or intentionally penetrated, however, care should be taken to preserve the integrity of tissue volume 22 and avoid penetrating further into lesion 20.

If cutting element 600 is equipped with one or more tubular members as previously described, lubricating agents, anesthetics such as lidocaine, or any number of other appropriate pharmaceutical agents may be administered through the tubular member lumen 660 so that they are deployed into the tissue through tube distal end 680. Preferably such agents are administered simultaneously as the blade 600 is advanced into tissue 10; however, they may be administered before or after the pathway is created. In addition, one or more sensors, fiber optics, electrocautery electrodes (to control bleeding during cutting), or other devices may be deployed through lumen 660.

FIG. 11 shows system 100 after blade 600 has been proximally withdrawn from tissue 10 and cannula 400, and a conventional trocar 420 has been deployed into the lumen of cannula 400 until its distal end 430 extends distally of the distal end of cannula 400. Trocar 420 and cannula 400 may then be advanced as a unit, or with the trocar leading in sequential deployment, into the tissue 10 through the pathway created by blade 600 to further define and enlarge it. Preferably, however, and as shown in FIG. 11, trocar 420 is advanced just to the edge or border of tissue volume 22 as previously described for deployment of cutting element 600 while the cannula 400 does not extend into tissue 10.

Trocar 420 is then removed by proximally withdrawing it from driver tube 400, leaving tube 400 in place either at the skin surface at the entry point of trocar 420 (as shown in FIG. 11), slightly into the aforementioned pathway, or deep enough into the pathway such that cannula 400 now occupies and even may be considered part of the pathway itself.

It should be noted that the steps heretofore explained in which a blade, trocar, and cannula are used to create the access port or pathway in tissue 10 to reach tissue volume 22 may be performed in any sequence or in any of a number of ways not described herein but are as known to those of skill in the art. It is not critical to the invention for the pathway or port to be created as described above.

The steps described above are merely exemplary of a method we have found to be useful; as long as a port is created in which the invention as described herein may be practiced, any method is acceptable.

FIG. 12 shows cannula 400 after trocar 420 has been withdrawn and oval deployment tube 300 has been inserted through the cannula 400 lumen and advanced distally to the vicinity of the border of tissue volume 22. Preferably, but not necessarily, tube 300 is advanced to a position just proximal to tissue volume 22 at the distal end of the tissue pathway as shown in FIG. 12.

Deployment tube 300 is shown in FIG. 12 connected to an orientation element 500 for indicating the alignment of locator element 200 as described above.

FIG. 13 depicts the next step. Distal portion 220 of locating element 200 has a ribbon or similar cross-sectional profile in which its width is larger than its thickness. Locator element 200 is disposed in pusher tube 730, and both, in turn, are disposed in deployment tube 300. This assembly is then placed in the lumen of cannula 400. Note that this configuration for pusher tube 730, deployment tube 300, locator element 200, and orientation element 500 is an alternative to the tissue pusher assemblies described above in conjunction with FIGS. 7A–7C and 8. The differences among the configurations and modes by which the locator element 200 may be deployed demonstrates the versatility and scope of the present invention as will be appreciated by those of ordinary skill in the art.

The FIG. 14 view of locator element is looking along its width, so that one only sees the uniform thickness of the locator element 200 as one moves from proximal portion 210 to distal portion 220. Therefore, only the edge of shoulder 240 is seen. However, the distal end of pusher tube 730 is shown abutting shoulder 240 so that as the proximal portion 210 of locator element 200 is distally advanced into the tissue via the distal end of pusher tube 730, the distal portion 220 of locator element 200 exits the distal end of deployment tube 300 to enter the tissue 10 in the vicinity of tissue volume 22.

For purposes of this illustration, oval tube 300 preferably is manipulated via orientation element 500 so that the major axis of the oval tube 300 cross section and the aligned width of the accompanying locator element are parallel to the y-axis. This helps to ensure that the deployed locator element 200 maintains the desired orientation with respect to the tissue 10 and the coordinate system, giving the radiologist important information relative to the location and orientation of the tissue volume 22 when marked. The surgeon will benefit from such an orientation as well when cutting around the surface of the ribbon along its width to more readily excise the tissue volume 22.

Once the deployment tube 300 and, simultaneously or subsequently, the locator element 200 is advanced so that their distal ends are in position in tissue 10, the locator element 200 is further advanced distally out of tube 300 distal end as shown in FIG. 13. As element 200 exits tube 300, it preferably will take on its predetermined shape and penetrate the tissue 10 to begin to define a tissue volume border 24 along a path. This border 24 in turn partially defines the tissue volume 22 to be excised by the surgeon.

Note that this illustrates a "polar" locator element deployment scheme. That is to say, proximal portion 210 of locator element 200 has a longitudinal axis that is substantially aligned or overlapping with the z-axis or central axis of the tissue volume 22. See the single dashed line bisecting lesion 20 in FIG. 13, which represents the position these axes take.

This ensures that the distal portion 220 of locator element 200 enters the tissue 10 at an initial point that is aligned with the central tissue axis or z-axis of tissue volume 22 and lesion 20.

FIGS. 14–16 show successive views of locator element 200 as it continues to advance along a path to define a tissue border of tissue volume 22 (now with stereotactic guide unit 80 removed for clarity). As the radiologist causes the pusher assembly 700 to advance distally, the distal end of pusher tube 730 continues to engage shoulder portion 240 to likewise distally advance the locator element 200.

As it deploys, the element 200 (and the path it occupies) preferably takes on an arcuate or curvilinear shape. More preferably, element 200 takes on a loop shape having a diameter greater than about 8 mm; more preferably greater than about 9 mm; even more preferably greater than about 1 cm; e.g., between 2 and 3 cm and up to about 7 cm or more. Locator element 200 may also take on a number of other shapes once deployed as previously discussed. The particular shape of the locator element is dictated by the shape of the tissue volume 22 and the particular tissue being excised.

A particularly useful feature of system 100 is that locator element 200 deploys along the first path in the tissue volume border 24 such that the distalmost portion of the tissue volume is encompassed by the path formed by the locator element 200. Said another way, we prefer that the distal portion 220 of element 200 extend to or even around the distalmost portion of tissue volume 22 (as measured in a downward direction along the z-axis) such that the element 200 bounds the tissue volume 22 containing the targeted lesion 20 along a continuous path. This path may be viewed as forming a physical border around the majority of the perimeter of the tissue volume 22. In the examples of FIGS. 13–16, distal portion 220 of locating element 200 continues well past the most distal portion of tissue volume 22 and forms a loop that substantially encompasses the border 24 along this path.

There are at least two significant advantages to this feature of system 100. First, when the locator element 200 is deployed into position as described above, manipulation of a proximal portion 210 of the locator element 200 will result in an equivalent or proportional manipulation of the tissue volume 22 enclosed by the element 200. For instance, if a proximal portion of element 200 is moved along the z axis, the targeted lesion 20 and enclosing tissue volume 22 will move an equal or proportional distance along the z axis. Likewise, pivoting or otherwise manipulating proximal portion 210 will result in a concomitant pivoting or other movement of the enclosed tissue volume 22. If the proximal portion 210 is replaced by a flexible cable, wire, suture, composite or the like as discussed above, manipulation of the wire results in a likewise and proportional manipulation of tissue volume 22.

A second important advantage of this feature of system 100 is that the surgeon may excise the tissue mass 22 by cutting along the surface of the locator element opposite the tissue volume and be confident that the entire volume 22 will be excised because the distalmost portion of the volume is encompassed by the locator element 200.

During or after full deployment of locator element 200 in the tissue 10 as described above, the radiologist may wish to partially or completely remove the element 200 from the body. For instance, if the locator element 200 is misdeployed or if there is a malfunction of some component of system 100, it may be desirable to reposition or even completely remove locator element 200 from the body.

To accomplish this, the radiologist simply pulls the proximal portion 210 or wire 290 in the proximal direction so that the locator element 200 retreats proximally into deployment tube 300, and straightens into its predeployment shape. She may exert opposite force in the distal direction on the pusher assembly 700 to provide leverage. Of course, the thumbscrew 720 in ferrule 710 should be loose to allow relative movement between the locator element 200 and pusher assembly 700. When the shoulder 240 retreats to an abutting position against the distal end of pusher tube 730, the radiologist may tighten thumbscrew 720 to fix the locator element proximal portion 210 in the ferrule 710 and continue to pull either the locator element or the affixed pusher tube proximally to further withdraw the locator element as she sees fit.

The unique profile and shape of the various locator element embodiments discussed and shown herein at least partially account for this feature of the invention. For instance, there are no barbs or hooks on locator element that would otherwise hinder or make reverse movement of the locator element 200 impossible. Furthermore, when element 200 comprises spring steel or a shape memory alloy such as nitinol, the element 200 may be straightened as it is proximally retracted into deployment tube 300 without little to no plastic deformation. This also serves to facilitate locator element 200 retraction and redeployment.

At this point, if the radiologist is satisfied with the position of locator element 200 in the tissue 10, she may decide to refrain from deploying one or more additional locator elements and present the patient to the surgeon for removal of the tissue volume 22. This is perfectly acceptable and is within the scope of the invention. For instance, the lesion may be well defined and conditions are such that excision of tissue volume 22 along a single locator element may be confidently accomplished.

However, to further define the tissue volume 22 along a different plane, at least one additional locator element may be deployed in the tissue. This is shown in simplified FIGS. 17–19 and discussed below.

As seen in FIG. 17, the radiologist will preferably first rotate or otherwise manipulate orientation element 500 through a selected angular displacement so that the major axis of the deployment tube 300 in turn is rotated an identical or proportional amount as desired. In this example, orientation element 500 is rotated ninety degrees so that the major axis of tube 300 and, when inserted into tube 300 lumen, the accompanying width of locator element 200' is oriented ninety degrees with respect to the width of deployed locator element 200, or so that the locator element 200' will deploy in a second path that is generally parallel to the y-axis.

Either before or after such rotation, second locator element 200' is inserted and advanced distally into the lumen of deployment tube 300 as previously described with respect to the first locator element. Preferably, under x-ray or other visualization technique guidance, the second locator element is advanced through the distal end of the tube 300 and penetrates tissue 10 so that locator element 200' further defines the tissue border 24 along a second path without penetrating tissue volume 22.

As the second element 200' is advanced along the second path, a second plane is defined that is preferably non-parallel to the plane defined by the first locator element 200. In this example, the second plane is angularly displaced approximately ninety degrees with respect to the first plane in accordance with the amount of rotation deployment tube 300. This is shown along a "polar" z-axis in the view of FIG. 18, looking down at the tissue volume 22 in the z direction, where the angular displacement α between the first and second locator elements 200 and 200' is readily seen.

When two locator elements are used to mark the tissue volume 22 for excision, we prefer to deploy the second locator element 200' so that it is angularly displaced in the tissue approximately ninety degrees with respect to the first locator element 200 as discussed above. Such a displacement is preferred, especially when each element is radiopaque and similarly shaped (i.e., a ribbon or other asymmetric cross-section), because of the ease with which the radiologist may view an x-ray image of the deployed locator elements and determine their orientation with respect to the grid assigned to the tissue. This is especially true when the first locator element is deployed into a path parallel to the x-axis, as a ninety-degree angular displacement of the second locator element about a polar axis will by definition place its path parallel to the y-axis.

Alternatively, the first and second locator element 200' may be angularly displaced approximately forty-five degrees with respect to one another. This may be preferred, for instance, if a third locator element is used, or if the particular lesion 20, patient condition, practitioner preference, or combination of these or other factors so dictate.

It is within the scope of the invention, however, that the second locator element 200' be displaced at any angle with respect to the first locator element around the common polar or z-axis. This is why the orientation element 500 may be infinitely rotatably variable; alternatively or additionally, it may be rotatable in fixed angular increments.

At this juncture, tissue volume 22 containing the suspect lesion 20 is bounded by first locator element 200 and second locator element 200' as schematically shown in FIGS. 18 and 19. Tissue volume 22 may be removed by any number of techniques as discussed below. However, a third locator element 200" (not shown) may also be deployed as previously described so that at least a portion of the third locator element 200" further defines the tissue border along a third path. This third path will preferably define a third plane that is non-parallel to the first and second planes.

For instance, third locator element 200" may define a third plane when deployed that is angularly displaced approximately forty-five degrees from each of the first and second planes. It is within the scope of the invention, however, for each of the locator elements 200, 200', and 200" to be disposed at any angle with respect to each other. Furthermore, the angles between any two of the elements may be different.

Additional locator elements may be used to further define the tissue volume 22 prior to excision as required.

Surgical Excision

Once the desired number of locator elements have been deployed into the tissue to define the tissue volume 22, the tissue is decompressed and removed from paddles 30, and the remaining components of system 100 may be removed from the site so that only the locator element and any proximally attached elements (such as flexible wire or suture 290) remain in the tissue 10. This is shown in FIG. 20 for the two-element deployment described above. Note that a proximal portion 210 of each locator element (or alternatively flexible wire or suture 290) extends through the skin surface. When the entire locator element is inside tissue 10 and a suture is attached at the locator element proximal end, the suture should extend through the tissue 10 and the skin surface so that it may be manipulated.

One advantage of this portion of the tissue marking and removal process is that if the other components of system 100 are removed from the vicinity of tissue 10, leaving only one or more locator elements and perhaps an attached suture extending through the skin surface, the tissue volume 22 does not have to immediately be excised as is the case with other tissue marking devices. The proximal portion 210 of locator element or the suture 290 is flexible enough that it may be taped or otherwise affixed to the patient's skin so that the patient may wait up to several days or more, with the chance to go home, before the volume 22 is removed by the surgeon. In this manner, excision may be scheduled for a convenient time within minutes or up to several days from the time of deployment.

Once the patient and surgeon are ready to excise the tissue volume 22, the patient is put under anesthesia and the surgeon accesses the tissue volume using conventional surgical tools such as scalpel 90 or electrocautery. She will cut around the outside surface of the locator elements to separate the tissue volume 22 from tissue 10 and then remove the tissue volume from the body. This is illustrated in FIG. 20A.

In general, the surgeon will first reach the tissue volume through any number of approaches. Some situations will dictate that the surgeon access the tissue volume 22 by cutting into the tissue 10 along the proximal portion 210 of the one or more locator elements 200 or along the flexible wire, suture or the like 290 attached to the locator element. Such an approach may be favored if the tissue volume 22 is near the surface of the skin and cutting along this path is the shortest and most clinically acceptable path. If the locator element deployment tube 300 and/or pusher tube 730 is still in the tissue 10, the surgeon may readily access the locator element along its surface, which is easy to locate, and follow with a scalpel to the locator element.

Alternatively or additionally, especially if the deployment tube 300 and pusher tube 730 have been removed from the tissue 10, the surgeon may reintroduce pusher tube 730 or may use a different stiffening tube (shown in FIGS. 20B–D) or grasping tool (shown in FIG. 20E) to aid in manipulating the tissue volume 22 and/or in following the proximal end 210 of the locator elements with a scalpel or electrocautery. The stiffening tube preferably has a feature on its distal end that engages with a locking feature on the locator element 200. For example, stiffening tube 201, as shown in FIG. 20B, includes wire lock 202 on its proximal end for locking onto the proximal end of locator element 200 (FIG. 20B). In an alternative embodiment, as shown in FIG. 20C, locator element 200 may additionally comprise flexible plastic tubing 203 surrounding the proximal end, and can be abutted to or adhered thereto. In that case, the metal tail of the locator element is desirable but not required. Additionally, a metal or other stiff tube 204 may be inserted between the plastic tubing and optional tail to serve as the pusher tube 730, as shown in FIG. 20D. When the locator element is in place in the patient, the pusher tube 730 is removed and the entire proximal end of the locator element, including the plastic tubing, is sufficiently flexible that surgical removal may be delayed. At the time of surgery, either the pusher tube 730 or a different stiffening tube is inserted to aid in surgical removal. The stiffening tube may have features on its distal end to engage features on the locator element and/or may have a wire lock on its proximal end to engage the locator tail. The flexible plastic tubing serves to electrically insulate the device from electrocautery and provide a clean pathway for the metal tubing to get to the tissue volume 22.

In another embodiment, grasping tool 206 is used, which is preferably a four-point clamp that can grasp two locator elements at an intersection, as depicted in FIG. 20E. This allows remote manipulation of tissue volume 22, such as application of tension and torque, from the proximal end of the grasper. Alternatively, the grasping tool does not have to grasp the locator elements, but may grasp only tissue in the vicinity of tissue volume 22. If desired, separate stiffening tubes or grasping tools may be used for each locator element 200 deployed. The stiffening tube or grasping tool may be optionally coated with an electrically insulative material or may be made of a high durometer insulative plastic for protection from electrocautery. Also a stiffening tube may be provided with forked tines (not shown) that can engage the locator element for manipulation of the element.

Alternatively, the surgeon may wish to approach the locator element along a path different than the proximal portion of locator element or suture. Under x-ray or other type of guidance, for instance, the surgeon may penetrate through the tissue 10 at a second site such as that shown in FIG. 20A as path 92 if, for clinical, cosmetic, or other reasons it is preferable to do so. When the locating element is disposed in breast tissue, a circumareolar approach 94, which minimizes the appearance of any scar, may be preferred. It should be noted that when an alternative surgical path to reach and remove the locator element and the enclosed tissue, even the proximal portion of locator element may be removed through this alternative path as formed by the surgeon. This allows the relatively small incision diameter through which the locator element was originally deployed to remain basically undisturbed. If a pusher tube 730 is reintroduced or a new stiffening tube (shown in FIGS. 20B–D) or grasping tool (shown in FIG. 20E) is used to aid in manipulating the tissue, it may be introduced through the skin at the site where the proximal portion of the locator element extends through the patient's skin. In that case, the stiffening tube or grasping tool would preferably be removed through the path it entered (preferably but not necessarily over the proximal ends of the locator elements 200) prior to removing the locator element (s) and tissue volume 22 through the alternative path 92 or 94. Alternatively, the stiffening tube or grasping tool may be introduced through the skin at the incision point in the skin through which the tissue volume 22 will eventually be removed, such as following path 92 or 94. A sharpened cannula (not shown) may be used to delivery the stiffening tube or grasping tool, or the stiffening tube or grasping tool may be modified to pierce tissue to access the tissue in the region of the locator element. In that case, the stiffening tube or grasping tool may be removed at the same time and through the same incision as tissue volume 22 and the locator element(s).

In any event, the fact that the surgeon may access the tissue volume 22 along a path different than the initial deployment path for system 100 is because the tissue volume 22 is now "palpable" in the sense that its border or perimeter is defined and occupied by one or more palpable locator elements. The tissue volume 22 is in a sense encapsulated by the locator elements.

Once the surgeon has cut through tissue 10 to reach the locator elements, she will next begin cutting through tissue 10 substantially along a surface of the locator element 200 that is opposite a surface of each locator element 200 disposed immediately adjacent the tissue volume 22. In other words, the surgeon will find the outside of the "cage" formed by the one or more locator elements and begin cutting along its surface to separate tissue immediately adjacent the outer surface of the "cage" from the tissue enclosed but not penetrated by the one or more locator elements.

As the surgeon cuts along the outer surface of the locator elements, she is able to discern the volume by visual and tactile cues, aided by her experience, and will cut around tissue volume 22 without penetrating it. Eventually, she will cut tissue volume 22 free from the surrounding tissue 10 so that it may be lifted with the locator elements enclosing the volume out of the tissue 10.

Tangential Deployment

There may be instances when it is desired to deploy one or more locator elements into the tissue 10 from an access point other than the polar location described above.

FIGS. 21–22 show a deployment of one or more locator elements 200 via an alternative tangential deployment technique. Here, the initial point of deployment of the distal end of the locator element 200 as it extends out of the deployment tube 300 lumen is substantially along a line that is tangent to the tissue volume 22 to be removed.

In contrast to the polar configuration of FIG. 16, a longitudinal axis 95 of a proximal portion of the locator element 200 is now substantially aligned with a tangential axis 96 of tissue volume 22 instead of a tissue volume central or polar (z) axis 98. This is shown for a single locator element in FIGS. 21A (perspective view) and 21B (planar view looking along the z-direction).

Note that if more than one locator element is deployed tangentially, the initial point of entry into the region of the tissue volume 10 border or perimeter will be along a different tangential tissue volume axis for each locating element. This may require multiple access ports be created in the tissue 10 via the blade 600 and driver tube or cannula 400, each aligned with the tangential axis along which a path or border will be created as the respective locator element is deployed along the perimeter of tissue volume 22. FIGS. 22A and 22B depict two locator elements 200 and 200' defining the border or perimeter of tissue volume 22 after having been tangentially deployed along tangential axes 102 and 104, respectively, as described above.

This is in contrast to the polar technique described earlier, in which each locator element generally deploys into tissue along a single central or polar axis of the tissue volume, thus requiring only a single tissue passageway as previously described.

Energy-assisted Cutting through Tissue

FIG. 23 depicts an alternative method in which a source 265 of energy is connected to locator element via a transmission cable 270, handle 272, and clamp 276. As previously described, there may be instances when it is preferable to energize the locator element or elements with RF energy to cut through tissue as an alternative means for removing the tissue volume 22 from the body once it is defined by the locator element or elements. For instance, one edge along the thickness of locator element 200 may be conductive and exposed (i.e., noninsulated) such that when energized by a source of RF energy, the locator element may be rotated as a single unit or "cage" through an angular displacement to cut through the tissue border defining tissue volume 22, removing it from the rest of tissue 10. The particular degree of angular displacement required to cut through the tissue volume 10 border so that it may be excised will of course depend on the number of locator elements present and their relative angular displacement.

Clamp 276 should be electrically conductive so to transmit the RF energy to the locator elements. A transmission cable 270 connected to either the clamp, the handle 272, or both, provides a conduit for delivering RF energy to the locator elements. An optional ground plate or similar return electrode (not shown) may be disposed on the patient's skin on tissue mass 10 or any other suitable part of the patient's body. Alternatively, the system may be configured to operate in bipolar mode with no need for a return electrode.

In operation, after deployment of the last locator element 200, delivery tube 300 and/or pusher tube 730 may be left in place in the tissue. Handle 272 and clamp 276 may then be slid over delivery tube 300 and/or pusher tube 730, with clamp 276 clamping onto the locator elements 200. Alternatively, delivery tube 300 and pusher tube 730 are removed to leave only the proximal ends of locator elements 200 extending from the skin of the patient. In that case, handle 272 and claim 276 may then be installed over the proximal ends of the locator elements to clamp onto the locator elements 200. A grasping tool such as that described above for tissue manipulation may be used to energize the locator elements 200. In that case, it is preferable that the grasping tool be electrically conductive, but covered with an electrically insulative coating, tubing, or the like.

Energy source 265 may also be used to energize the locator element to provide electrocauterizing energy to the tissue as it is being excised so to minimize bleeding, etc.

RF energy source may also contain or alternatively be a thermal energy source, such as a laser or the like, for delivering thermal energy to the locator element and tissue volume 22. Transmission cable 270 in this instance may comprise a fiber optic cable, for instance, to transmit this thermal energy. It is also within the scope of the invention to additionally or alternatively include a source of mechanical or acoustic (such as ultrasonic or vibrational) energy for supplementing or substituting for the other types of energy discussed herein.

One particularly useful configuration is where at least one edge 250 or 260 of the locator element forms a cutting surface or blade to cut through tissue when the locator element is rotated as described above. This type of cutting may be purely mechanical or it may be assisted by the use of RF or other energy sources to assist the locator element cutting surface in cutting or separating tissue 10.

FIGS. 23A and 23B show an alternative use for a similar locator element configured for tangential deployment. These figures depict 360-degree rotation of the deployed locator element 200 about the deployment tube 300 major or longitudinal axis 302. Although the locator element may take on a variety of shapes when deployed (circular, elliptical, etc.), FIG. 23A shows a variation in which locator element 200 takes on a modified ellipse when deployed in tissue. Rotation of this locator element 200 in the direction of the arrows to cut through tissue results in a modified disk-shaped tissue volume 26 as seen in FIG. 23B. This volume has a more flat proximal surface 32 than the recessed profile characteristic of the toroid-shaped volume tending to result from the rotation of a locator element that assumes a more circular deployed shape. This may result in the capture of more calcifications or suspect tissue within volume 26.

As discussed above, the method depicted in FIGS. 23A and 23B may be accomplished with or without the assistance of RF or other energy. It may also be accomplished by a locator element that comprises one or more cutting surfaces or blades on one or more of the locator element 200 edges.

It is likely that the tissue corresponding to the center of the tissue volume 26 of FIG. 23B will have contained suspect tissue such as microcalcifications. In other words, locator element 200 will have penetrated suspect tissue. While we previously noted that we prefer to surround the tissue volume to be excised by creating a border or path without penetrating it, the invention is not so limited. As with the locator element of FIGS. 23A and 23B, each of the locator elements and configurations described herein, both polar and tangential, may penetrate the tissue volume to be removed.

This invention also contemplates the use of techniques to monitor and control the output from a high frequency power supply or other energy source such as RF unit 265. For instance, a neutral electrode may be used in conjunction with the locator element (which may act as an active electrode) to detect current leak, to detect impedance of the circuit and the tissue, or sense the temperature of the tissue in the vicinity of the active electrode (locator element). Both monopolar and bipolar configurations are possible. Measurement of these and other feedback data may be used to manually or automatically control the RF source 265 output level, for instance. Such systems are widely known in the art as described in, for instance, U.S. Pat. Nos. 5,540,683 to Ichikawa et al., U.S. Pat. No. 5,300,068 to Rosar et al., and U.S. Pat. No. 6,019,757 to Scheldrup, each of which is hereby incorporated by reference.

Although the foregoing discussion is in the context of the marking and removal of a nonpalpable mass or lesion located within a human breast, the invention is not so limited. This invention may be used to fixedly and removably place one or more locator elements in tissue in a wide range of sites in the body.

For instance, system 100 may be used to mark tissue in any number of organs (e.g., breast, liver, lungs), muscle or fat tissue, or even cavities such as the abdominal cavity. It is also within the scope of the invention that foreign objects such as bullets, etc. may be marked for removal by system 100. The versatility of system 100 is highlighted by the variety of configurations and methods in which system 100 may be used.

Redeployment and Reexcision

As discussed above, situations may arise in which not all of a region of suspect tissue can be encompassed in a single tissue volume.

For instance, diffuse processes such as Ductal Carcinoma In Situ (DCIS) present an asymmetric distribution of microcalcifications that may extend through a large portion of the breast. In these situations, it is simply impossible to define a relatively small volume of tissue that contains all of the suspect tissue that can be encapsulated by the locator element or elements in a single deployment as described above.

In these instances, it is desirable to obtain multiple tissue samples. Therefore, the present invention includes marking a tissue volume for excision, excising that tissue volume, and redeploying the device at a second location (preferably but not necessarily adjacent the tissue volume just removed) for marking a second tissue volume for excision. These techniques may be desired if a particularly large area of suspicious tissue needs to be removed, or for instance if the volume of suspicious tissue is an irregular shape that a given locator element may not be capable of defining in a single deployment.

An example of this technique used for excising a second tissue volume 22' below a first tissue volume 22 is shown in FIG. 24A. Here, a locator element 200 is first deployed in a polar fashion into tissue 10 as described herein to define a border of tissue volume 22 containing suspect tissue. After this tissue volume 22 is excised by the appropriate technique, preferably by locator element 200 or by cutting surgically with a scalpel as described above, a cavity is left behind. However, additional calcifications or other suspicious tissue may still be left in the body adjacent or in the vicinity of the cavity.

In this instance, the user may deploy the same (or a different) locator element 200 into the tissue volume 22' defined by the remaining suspect tissue or calcifications. The process of redeploying the same locator element or deploying a different locator element to mark tissue volume 22' is the same as described above. Once this additional volume 22' is marked, it may be excised via the same pathway and technique as was tissue volume 22 (this is preferable because the same incision may be used, thus minimizing tissue trauma and scarring potential) or by a different route if so desired.

This redeployment and reexcision may be repeated as many times as needed to mark and remove all suspect tissue to the satisfaction of the physician or radiologist. As previously mentioned, this technique will most likely be used to mark and excise tissue volumes having an odd shape that are not capable of excision with the particular locator element in the hands of the user. However, redeployment and reexcision of additional tissue volumes in adjacent or nonadjacent areas are certainly possible and readily within the scope of the present invention. In addition, this methodology may be accomplished by any of the embodiments or combination of embodiments herein described.

As shown in FIG. 24B, two or more locator elements 200 and 200' may be deployed at different depths from the skin surface for simultaneous surgical excision. Elements 200 and 200' may have different shapes, diameters, deployment configurations as required. They may also be accompanied by other instruments or additional locator elements as the practitioner sees fit to use.

Guidance and In Situ Formation of Tissue Locator Element

The following features of the present invention enable one to guide or divert locator elements having a pre-formed deployment shape during deployment in a desired direction as they enter tissue. They also enable one to undergo in situ cold-formation of locator elements having no such pre-formed shape during deployment.

FIGS. 25A–25D show a locator element deflector or divertor mechanism that guides the deployment of a pre-formed locator element, ensuring that it eventually resides in the tissue to accurately define a tissue volume in the intended shape and configuration.

As discussed above, when locator element 200 comprises a shape-memory material such as nitinol or spring steel, it preferably has been given a predetermined shape that corresponds to its desired shape and configuration when deployed in tissue 10.

However, especially for a polar deployment configuration, the locator element 200 should preferably deploy in the correct direction as it first enters the tissue so that it takes on the desired final configuration to define tissue volume 22. This may require a diversion or corrective deflection of the locator element during deployment via a ramp or deflector 304 as shown in FIGS. 25A–25D.

Turning first to FIG. 25A, a cross-section of a distal end of delivery or deployment tube 300 is shown with a polar locator element 200 disposed within its lumen 310. A moveable divertor or ramp 304 is seen in delivery tube 300 lumen near tube distal aperture 306.

Ramp 304 has a tapered profile so that the locator element 200 may be readily guided along the ramp surface throughout deployment. Ramp 304 may be slidably affixed to deployment tube 300 by a groove or similar feature and may be axially moved from an initial stowed pre-deployment position (as seen in FIG. 25A) to a final deployment position (as seen in FIG. 25C) by any number of mechanisms such as mechanical, electromechanical, hydraulic, etc. In addition, the ramp may be manually controlled via, e.g., a control wire, or it may be automatically activated as the user deploys the locator element 200 into tissue. Any number of ramp affixation configurations and deployment mechanisms, as will be known to those of skill in the art, may be used for ramp 304.

Ramp 304 may be of a simple construction as shown in FIGS. 25A–25B to guide the locator element, or it may comprise a shape memory or similar material configured so that the ramp increases in curvature as it exits deployment tube 300. Further, ramp 304 may be of a more complex construction so that its shape can be manually controlled by a user. Although ramp 304 is shown having a simple triangular shape in the figures, its geometry may vary as design dictates.

FIG. 25B depicts the initial deployment of locator element 200 through distal aperture 306 of deployment tube 300. Ramp 304 moves simultaneously with the locator element to guide the locator element distal end 230 away from deployment tube longitudinal or central axis.

In FIG. 25C, ramp 304 is fully deployed. The user continues to advance locator element 200 along the ramp 304 surface in the direction indicated. For this particular polar locator element 200, its distal end 230 is prebiased to curve in the opposite direction. The opposing biasing forces of the locator element distal end 230 and the ramp 304 keep each in constant contact with the other during this initial deployment step, providing a low profile to the pair as they enter tissue 10 through the cavity previously created by blade 600.

Once the locator element 200 is advanced to the point at which its distal end 230 is beyond the ramp 304, as shown in FIG. 25D, the locator element begins to curve in the opposite direction as it assumes its predetermined shape to define tissue volume 22. Of course, as discussed herein, locator element 200 may be retracted if the user is not satisfied with its position in the tissue and may be redeployed, with or without the assistance of the ramp 304, until the proper deployment position and configuration is achieved.

Although FIGS. 25A–25D show ramp 304 and locator element 200 deploying simultaneously, ramp 304 may alternatively be deployed into tissue prior to the locator element 200 as the situation requires.

FIGS. 25E–25G show a variation of the locator element deflector or diverter mechanism that guides the deployment of a preformed locator element. As described above with respect to FIGS. 25A–25D, the locator element 200 should preferably deploy in the correct direction as it first enters the tissue so that it takes on the desired final configuration to define tissue volume 22. This is especially desirable in the case of a polar locator element 200. As shown in FIG. 25E, ramp 304 is replaced by an inner curved cannula 404. Inner curved cannula 404 may be circular or may have a noncircular outer profile or lumen, depending on the shape of the delivery cannula 300 lumen and locator element 200, respectively. In operation, first, outer delivery tube 300 is positioned proximal of the lesion. As shown in FIG. 25E, inner curved cannula 404 is advanced, either alone or along with polar locator element 200 residing within it, through the delivery tube 300 to direct the polar locator element 200 in a direction preferably away from the point of the outer delivery tube 300. As shown, the polar locator element 200 is advanced out of inner curved cannula 404 by advancing pusher tube 730 (not shown) and follows a path to circumscribe the lesion. In this case, pusher tube 730 is flexible enough to follow the curve of the inner curved cannula; it may or may not be precurved, and is made of spring steel, nitinol, or the like, and may be circular or noncircular. As shown in FIG. 25F, inner curved cannula 404 is then retracted while leaving polar locator element 200 in place in the tissue. As shown in FIG. 25G, delivery tube 300 is subsequently retracted, leaving polar locator element 200 in place.

Low-friction variations of the deflection or diversion mechanism are shown in FIGS. 26A–26B. In the embodiment of FIG. 26A, two rollers 312 and 314 sequentially disposed in deployment tube 300 work together to divert the distal end 230 of locator element 200 (shown along its narrow dimension) during deployment. As the locator element distal end 230 approaches the first roller 312, it is forced to one side of the deployment tube lumen 310. It then encounters the second roller 314, which is partially disposed outside deployment tube 300, and exits in a direction at an angle with respect to deployment tube central axis 302.

A three-roller configuration is shown in FIG. 26B. Here, rollers 312 and 314 are generally aligned with one another while a third roller 316 is positioned distally to guide the locator element 200 as desired. We prefer that the position of third roller 316 be adjustable as shown in FIG. 26B so to control the direction and degree of bias of locator element 200 as it exits the deployment tube 300. As is known to those of skill in the art, this three-roller configuration may be used to impart some cold-working into the locator element, depending in-part upon the material chosen for the locator element 200, rollers 312–316, and the relative positions of the rollers.

The distal end of the deployment tube lumen 310 may also be angled so to help guide the locator element 200 in the desired direction.

Turning now to FIGS. 27–29, an alternative locator element 205 is shown being formed in situ by an alternative deployment tube 305.

This alternative embodiment is best described in the context of the method of using system 100. Although deployment tube 305 and locator element 205 are slightly different than their counterparts described above, this embodiment is deployed largely as previously described with the exceptions noted below.

Alternative locator element 205 is shown in a flat and straightened form in FIG. 27A. Element 205 is largely identical to locator element 200 previously described except that it is capable of being plastically deformed upon advancing through the deployment tube 305 and die 307 as discussed below. This feature may be described as a cold-die forming technique similar to draw or compression processes as are well known in the materials processing industry.

FIG. 27A shows a locator element 205 formed into a flat shape prior to deployment in the tissue. Locator element should have any desired features, such as the profile of the distal end, any cutting surface, and any proximal hole for attachment of a suture, etc., incorporated into the element prior to deployment in tissue 10. Care should be taken to ensure that any coating on locator element 205 will not be marred or abraded by the process described below.

In FIG. 27B, locator element 205 is shown being distally fed into a lumen 303 of deployment tube 305 via a pusher 700 (not shown). The cutaway profile of the distal region of tube 305 reveals the path element 205 takes as it travels distally through tube lumen 303 and approaches cold-forming die 307 and die cavity 309. Die and die cavity are configured to bend the distal portion 207 of locator element 205 as it passes axially through die cavity 309 and into the tissue 10 to define a tissue border along a path that in turn defines tissue volume 22. FIG. 27C schematically depicts this process with tissue volume 22 removed for clarity.

Once locator element has been plastically deformed in this manner and has passed completely through die cavity 309 to take on the loop or arcuate configuration shown in FIG. 27D, the deployment tube 305 containing die 307 is proximally withdrawn or rotated for the optional deployment of an additional locator element as discussed in detail above.

Preferably, locator element 205 is a ribbon or similar form having a width larger than its thickness. Of course, die 307 and die cavity 309 are appropriately shaped to impart the proper amount of plastic deformation for the dimensions of locator element 205 and the material used so to exceed the elastic limit of the locator element while avoiding overstressing it, which could cause edge or surface cracking that could interfere with the element's performance. More or less severe curves than that shown for die cavity 309 are within the scope of the invention. Other die cavity profiles may include irregular and other various shapes, such as reverse curves, etc., so that a variety of desired final shapes of the formed locator element 205 may be realized.

Care should be taken to ensure that the surfaces of die that form the die cavity 309 are smooth so to avoid creating surface irregularities in the locator element or damage to the insulating or other material that may be coated onto the element 205 surface as described above.

Die 307 may be made of any appropriate material suitable for serving its intended purpose. Preferably the die comprises a biocompatible tool steel such as a tungsten or low-alloy steel or other metal, alloy of such, or composite as may be appropriate. Locator element 205 may comprise any suitable material as discussed above, including those materials that do not exhibit shape memory characteristics. Other than the typical materials requirements such as biocompatibility, radiopacity, etc., the material should at least also be selected to allow the locator element to exceed the elastic limit so to plastically deform into the permanent shape as it is passed through die 307.

FIG. 28 depicts an embodiment of the invention in which a die 311 having a positive curve 313 and a reverse curve 315 is used to cold-form a locator element while simultaneously deploying it in a polar configuration. Here, die cavity 317 first subjects the flat locator element to a reverse curve 315 as it is advanced by pusher 700. This deforms element 205 into a first curve that prepares and aligns it for the proper final shape as it is formed through positive curve 313 and exits die cavity 317 in the desired arcuate or loop shape. Such a die allows locator element 205 to deploy in the preferred polar configuration as discussed above. As with the previous examples, curves 313 and 315 may have a variety of curvature radii, differing radii; the die may also have additional curves if so desired.

FIG. 29 depicts a variation of the embodiment of FIG. 28 in which die 317 is adjustable. As shown, lead screw 319 or a similar element is rotatably disposed in a lumen of the upper portion 321 of the die that is slideably affixed to die lower portion 323. Rotation of screw 319 in either direction moves upper portion 321 distally or proximally relative to lower portion.

The distal end 325 of lower portion of the die is curved so to impart a particular curvature to die cavity 327, thereby imparting a corresponding curvature to locator element 205 as it passes through. Distal end 329 of die upper portion is appropriately shaped with a positive curve to impart a final shape to locator element 205 as discussed with respect to the FIG. 28 embodiment. However, the axial adjustability of the upper portion 321 allows the distal ends of each portion of die 317 to form a variety of positive curve shapes that in turn will form locator element 205 rings having a variety of different diameters, ranging preferably from between about 0.5 cm to about 3.0 cm or more.

Lead screw 319 is but one of any number of mechanisms suitable for adjusting the axial position of die upper portion 321 relative to die lower portion 323 within the scope of the invention.

An alternative embodiment for the polar deployment of cold-forming locator element 205 discussed herein is shown in perspective in FIG. 30. Handpiece 350 comprises a handpiece body 352, a cold-forming deployment tube 354, a release trigger 356, a ratcheting trigger 358, and a locator element loading port 360 disposed on a proximal end 362 of handpiece body 352.

Loading port 360 is in communication with a loading tube 364 (shown in FIG. 30 in hidden lines) that extends through handpiece body 352 to a distal end 366 where it communicates with and is connected to a proximal end of coldforming deployment tube 354. Preferably, loading tube 364 has an oval or circular cross-section having a sufficient size to allow passage of the locator element 205 therethrough. We prefer that deployment tube 354 has a cross-sectional profile and size similar if not identical to those of loading tube 364. Of course, cold-forming deployment tube should have an outer diameter and length that allow it to be disposed in the lumen of driver tube 400 for deploying locator element 205 into tissue 10 from its distal end 366 as described herein.

Ratcheting trigger 358 is configured as known to those of skill in the art so that when the release trigger 356 is activated to unlock a ratcheting mechanism, the user will pull or "squeeze" it in a proximal direction. This will cause advancing means (not shown) in the handpiece body to incrementally distally advance a locator element 205 that has been previously loaded into loading tube 364 through loading port 360. Each time the user releases and pulls the ratcheting trigger, locator element 205 distally moves an additional incremental distance, eventually advancing through cold-forming deployment tube 354 to its distal end 368. Of course, the particular incremental distance the locator element 205 is advanced with each squeeze of the ratcheting trigger 358 may be tailored to suit the needs of the user. The particular mechanism described herein by which locator element 205 is advanced, the details of which are well known in the art, is merely exemplary. Significant deviations from this design as well as other designs are within the scope of the invention. For instance, the advancing mechanism may be automated instead of manual.

A cold-forming die (not shown) similar to, e.g., die 307 or die 311 discussed above is disposed in the tube distal end 368. As the locator element 205 advances, the distal tip of locator element 205 enters a die cavity and bends as it passes axially therethrough. Eventually, the locator element 205 exits the die cavity and the distal end 368 of cold-forming deployment tube 354 and into the tissue 10 to define a tissue border along a path that in turn defines tissue volume 22. As seen in FIG. 30, this embodiment of handpiece 350 is configured for a polar deployment of locator element 205;

handpiece may be used to deliver multiple locator elements as described herein as well as to deploy one or more locator elements in a tangential fashion.

In use, the other elements of the invention described herein are used to prepare the tissue for locator element as described above in conjunction with FIGS. 10–13. Once a tissue port is created, a locator element 205 is next loaded (or has been pre-loaded) into handpiece 350 and tube 364 so that the distal end of the locator element 205 is at, near, or partially through the die cavity in deployment tube distal end 368 (but preferably not so that it extends out the tube distal end). The user then places the cold-forming deployment tube-locator element combination into and through the lumen of deployment tube 300 such that the distal end 368 is disposed at the tissue of interest. Alternatively, locator element 205 may be loaded into the handpiece 350 after handpiece is disposed in deployment tube 300.

As the user pulls or squeezes the ratcheting trigger 358, locator element 205 is advanced through the die cavity, forming the desired shape as it exits the distal end of cold-forming deployment tube 354 and into the tissue 10 to define tissue border 22. Once the locator element 205 is deployed, i.e., advanced through and out the distal end 368 of cold-forming deployment tube 354, the user may load additional locator elements into the handpiece 350 in other angular orientations as described herein, or she may proximally withdraw the handpiece 350 from deployment tube 300 to conclude the deployment procedure.

Yet another embodiment of the present invention is shown in FIGS. 31–33. A feature common to the variations of this embodiment includes a pivot or rotation point around which a locator element turns after deployment in the body to cut the defined volume of tissue for excision.

FIG. 31 shows a tangentially deployed version of this embodiment. Locator element 200 is shown disposed out of a directional translator 370 disposed at the distal end 372 of deployment tube 300.

Locator element 200 is shown in FIG. 31 as deployed in a semicircle about an axis 374 perpendicular to an axis 376. In this way, the locator element distal end 230 generally is disposed about 180 degrees from its point of departure from directional translator 370. In general, we prefer that locator element 200 distal end reaches the distalmost portion of the tissue volume to be excised as discussed previously. Other variations provide for a complete deployment of locator element 200 generally through about 360 degrees. Locator element 200 may be pivoted or rotated about axis 376 to cut tissue volume 22 from the body via a mechanical or energy-assisted cutting action, or combination thereof as discussed herein.

Locator element 200 is preferably equipped with one or more cutting surfaces, such as leading edge 250. Upon rotation, edge 250 cuts into the tissue to excise the tissue volume 22 of interest. A wide variety of configurations may be used for locator element as described herein, including using RF or other energy forms to assist in cutting.

In use, deployment tube 300 is advanced into the body as described herein so that the distal end 372 reaches the vicinity of the tissue volume 22 of interest, preferably without penetrating that volume. The user axially advances locator element 200 through the lumen of deployment tube 300 as described above. As the distal end of the locator element reaches the distal end of the deployment tube, it exits into the tissue and assumes its preformed shape. The user advances the locator element until it reaches the desired position, preferably 180 degrees from its point of departure around axis 374 as shown in FIG. 31. If desired, locator element may be advanced 360 degrees around axis 374 so that it forms a complete circle.

If the cutting element forms a semicircle when fully deployed as shown in FIG. 31, an actuation mechanism (not shown) may be used to rotate locator element 200 about axis 376 to cut through the tissue and define a tissue volume 22 as discussed herein. The locator element will be rotated through 360 degrees in order to cut a complete tissue volume 22.

On the other hand, if the locator element is deployed into a full circle, it need only be rotated through 180 degrees to cut the same volume of tissue. This method is less preferable than the semicircular deployment method of FIG. 31 due to the greater moment created by the longer locator element.

Once the tissue volume 22 is cut, locator element 200 may be partially or fully retracted into the deployment tube, and the tissue volume 22 may be removed from the body by any means known to those of skill in the art. It is preferable, however, to leave locator element 200 deployed to some extent into the freshly cut tissue volume 22 border, or at least to leave the deployment tube disposed in the region of tissue volume 22, so to allow the surgeon to cut along the deployment tube as discussed herein and access the tissue volume 22 for retrieval. It is also within the scope of this invention to use other means to remove the tissue volume 22 as is known to those of skill in the art, such as mechanical, vacuum-assisted, etc.

Any suitable drive mechanism may be used to rotate the locator element 200 about axis 376. For instance, FIG. 32 shows a partial cross section of a distal region of the inventive device in which a locator element proximal end is affixed to a shaft 380 extending through an aperture 306 in the distal end of deployment tube 300. Shaft 380 is connected to or is part of a gear or pulley 382 that is rotatably disposed in the lumen of deployment tube 300. A drive belt, wire, or similar device 384 may be remotely or locally actuated, by manual or automated means, to rotate pulley 382 and accordingly rotate shaft 380 and attached locator element 200 through the desired angular rotation. Pusher 386 is shown affixed to shaft 380 and is used to axially advance or retreat the locator element 200 through the lumen of deployment tube 300. Pusher 386 also serves to provide a support for shaft 380 as it rotates.

An alternative configuration shown in FIGS. 32A and 32B comprises a simple pull wire 388 that is fixed at one end 390 to pulley 382. This pull wire 388 replaces belt or wire 384 in the previous embodiment. Pulley 382 may be biased by a spring or similar means to wrap a portion of pull wire 388 therearound. When the user moves pull wire 388 in the proximal direction, it binds against the pulley, causing it to rotate, turning element 200 in the same direction.

Any means for actuating rotation of the locator element, including mechanical, electronic, magnetic, etc. as known to those of skill in the art are within the scope of this invention.

The embodiments shown in FIGS. 31–32 present several advantages over current devices. First, the tissue volume 22 may be removed in one contiguous sample without penetrating it. The orientation of the tissue volume 22 with respect to the body may be maintained because the locator element 200 rotates around the tissue volume 22 by a known degree of rotation (e.g., 180 or 360 degrees) as it cuts through tissue without rotating the volume 22 itself. When the cored sample is removed by any of a variety of means, the tissue volume 22 may be marked with sutures or the like to indicate the proper orientation.

Yet a further embodiment of a rotatable locator element is shown in FIGS. 33A–33B. Here, locator element 200 comprises two similarly shaped segments connected at shaft 380 and pin 398.

Outer segment 392 is preferably rotatably fixed to wire or ribbon 394 while inner segment 396 is preferably rotatable about shaft 380 and pin 398 as described above for cutting through tissue to define tissue volume 22. FIG. 33A shows a tangentially-deployed variation while FIG. 33B depicts a polar deployment variation.

Fixed segment 392 provides an added degree of stability for the device as inner segment 396 cuts through tissue. Fixed segment 392 also provides more structure surrounding the cut tissue volume 22 to accommodate the excision process. It also allows the surgeon to more readily locate tissue volume 22 for removal by surgical access as described above.

Inner segment 396 is slightly shorter than outer segment due to the smaller arc inner segment 396 occupies when deployed. Therefore, when locator element 200 is disposed in deployment tube 300, outer segment 392 may bind and take on an arcuate or serpentine profile while inner segment 396 remains straight (assuming there is no strain relief feature in the device to allow the outer segment to relax). This has the advantage of providing a spring or restoring force to locator element 200 to aid in its deployment into the tissue.

Both inner segment 396 and outer segment 392 may be rotatable; alternatively, outer segment 392 may be rotatable while inner segment 396 is fixed. If both segments rotate, the device may include counter-rotating shafts (not shown) so that the segments rotate in opposing directions. This may serve to apply a more even cutting pressure on the tissue and help to stabilize the surrounding tissue, which may result in a more consistent tissue volume 22 border. It is also within the scope of the invention to include more than two segments in this variation.

Locator Element Proximal End Pouch

A particularly useful way to affix the proximal portion 210 of locator element or the suture 290 to the patient's skin is via enclosure or pouch 110 shown in FIG. 34.

In one embodiment, pouch 110 comprises a body 112, an access flap or lid 114, a biocompatible adhesive layer 116 or other affixation means, and a peel-away release paper 118 that is removed prior to affixation on the patient's skin 120 so to expose the adhesive layer 116. An optional perforation 122 extending around a portion of or the entire perimeter of the top portion of pouch body 112 provides a tear-away feature for easy access to the proximal portion 210 of locator element or suture 290 disposed therein. To ensure a secure and low-profile configuration, access flap or lid 114 may comprise a slit 124 or similar feature through which proximal portion 210 or suture may protrude from pouch body 112. We also prefer that the flap or lid 114 contain an adhesive layer or similar affixation means 116' for securing the lid 114 to the top portion of pouch body 112.

Pouch 110 is preferably made from a transparent or opaque polymeric material. It should be flexible and lightweight, yet body 112 should have a sufficient tear and tensile strength to resist damage such as inadvertent puncture, etc. It may also be partially or entirely colored for aesthetic purposes and contain markings as appropriate. Pouch 110 should be large enough to easily accommodate the distal portion 210 of locator element 200 or suture 290, yet small enough so that it may be readily affixed to the patient's skin 120 without discomfort or awkwardness.

The user will peel away release paper 118 or a similar feature to expose the adhesive layer 116 on the underside of pouch body 112. She will then place the pouch on the patient's skin 120, preferably close to the point at which the proximal section 210 or suture 290 emerges from the body. A particularly suitable location when the invention is used to mark lesions in the breast is on the patient's chest or shoulder on the side of the body closest to the marked breast. Alternatively, pouch 110 may be affixed to the patient's abdomen or even back as the situation requires.

Locator element proximal section 210 or suture 290 extending from the patient's body may be coiled or otherwise bundled to form a coil as shown in FIG. 34. Tape or other means may be used to keep the coil bundle intact. After the coil is placed into the pouch body 112 and flap 114 is closed with adhesive 116' such that the proximal section 210 or suture 290 protrudes through slit 124 on flap 114. Alternatively, there may be a gap between the adhesive layer and the junction between the flap 114 and pouch body 112 such that this portion of the coil may simply exit through the side of the pouch 112 near the flap-body intersection. If desired, an optional strain relief device, such as a piece of surgical tape or the like, may affix a portion of the proximal section 210 or suture 290 to the patient's skin 120 between the pouch 110 and the point at which the proximal section 210 or suture 290 emerges from the body. This will help to ensure that inadvertent movement of the coil does not disturb the portion of locator element 200 in tissue 10.

The coil may be removed by simply opening the flap 114 and pulling it out of pouch body 112, or the operator may tear open the pouch body 112 along perforation 122 so to expose the coil. We prefer to use the perforation feature to reduce the risk of harming the patient if the flap proves difficult to open.

The aforementioned description of the pouch 110, its features, and a method for its use is merely exemplary, and significant variations from the above description as will be contemplated by those of ordinary skill in the art are within the scope of the invention.

Offset Fixture

Offset fixture 900 shown in FIG. 35 is designed to readily facilitate the tangential deployment of one or two locator elements. Other elements of the present invention (such as driver tube 400, clock wheel 500, etc.) have been removed for clarity.

In FIG. 35, fixture 900 is shown with deployment tube 910 disposed a distance "y" and deployment tube 920 disposed a distance "x" from fixture central axis 930 along respective axes that are oriented about ninety degrees to each other. Deployment tubes 910 and 920 may be permanently fixed on fixture body 940 or they may be adjustable so that their location relative to the central axis 930 can be tailored to the dimensions and shape of the tissue volume 22 that the user desires to remove. For instance, if an elliptically-shaped tissue volume 22 is needed, the "x" and "y" distances preferably will not be equal (and preferably neither will be the diameters of the loops formed by locator elements 922 and 912) Any combination of positions for deployment tubes on fixture body 940, including positions other than along the "x" or "y" axes shown in FIG. 35, are possible. In addition, more than two deployment tubes may be used.

Not shown are two fixture lumens disposed in fixture body 940 extending through the body from the point at which deployment tubes 910 and 920 meet body 940 to the opposite end 942 where they are open for the insertion of a locator element and/or other components of system 100. These fixture lumens are axially aligned with the lumens of deployment tubes 910 and 920.

Similar to the deployment technique discussed above with respect to FIGS. 22A and 22B, FIG. 35 shows how the tangential deployment of locator elements 912 and 922 through fixture body 940 and deployment tubes 910 and 920, respectively, defines a border or perimeter of tissue volume 22 having central axes 930 and 936.

Fixture body 940 is designed with a conventional sliding track interface mount 950 and locking pin 960 as is well known in the art for connecting the fixture to a Fischer Table or the like. This design readily interfaces with such existing commercial platforms, and provides a high degree of versatility so that the physician can tangentially deploy one or more locator elements of the invention without significant investment in additional custom equipment. Of course, other techniques for mounting fixture body 940 as are known to those of ordinary skill in the art are contemplated as well.

Although the alternative offset fixture 900 shown in FIG. 35 is configured for use with a stereotactic table, fixture body 940 may take on a wide variety of other configurations so that offset fixture 900 may be used with standup units or other devices. Offset fixture 900 also need not connect to any platform and can be modified to be used in a hand-held mode to give the user greater versatility in targeting specific regions of the body that may not be amenable to conventional fixtures and platforms.

It is not necessary that offset fixture 900 be used strictly for tangential deployment. Offset fixture 900 may alternatively be configured for polar deployment of one of the locator elements along axis 930 in combination with the tangential deployment of the other or additional locator elements.

In its most general sense, offset fixture 900 is widely adaptable to deploy more than just a locator element. For instance, deployment tubes 910 and 920 may be used alone or in combination to deploy any number of general biopsy devices, localization wires, drugs, or other devices or materials in various combinations as known in the art. For instance, a radiolabled material, such as colloids marked with technetium, may be injected into the lesion area through one deployment tube 910, and a gamma-detecting probe may then be deployed into the tissue through deployment tube 920 to aid in excision of the so-labeled tissue.

This is but a single example demonstrating the versatility of offset fixture 900 and the myriad applications in which it may be used to accurately place devices and materials in tissue of interest where a high degree of accuracy and control is needed.

Tissue Localization Device

Although the locator element described thus far is primarily intended to define a path or border around a volume of tissue, it is also within the scope of the invention to deploy the locator element so that it penetrates into that volume, which may also include a lesion. In this manner, the present invention may be considered an improved localization device or localization wire.

All of the components and configurations described thus far may be used when deploying the locator element 200 as a localization device to penetrate tissue such as a lesion. That is to say, any of the aforementioned embodiments and their equivalents may alternatively be used for this application.

We have found, however, that a useful configuration for such an application requires relatively few components. In particular, a smaller version of locator element 200 shown in FIG. 3A, together with the pusher or wire stiffening tube 730 and tissue localization wire delivery or deployment tube 300 shown in the perspective view of FIG. 3B, is a suitable exemplary assembly. The terms "wire", "locator element", "localization device", "localization wire", "tissue localization wire" and the like may be used interchangeably as defined by the terms set forth herein.

A more detailed description of a tissue localization wire assembly and a method for using it to penetrate and mark tissue, such as lesion 20, is provided below. In the following discussion, like reference numerals refer to like elements unless otherwise specifically mentioned.

In general, localization device or wire 200 may take the form of any of the locator element embodiments described herein. The embodiment shown in FIG. 3A is particularly useful. Such a device preferably is a unitary, single-piece element comprising nitinol or other superelastic material as previously described. Wire 200 preferably consists of a proximal portion 210 and a distal portion 220 having a sharpened distal tip 230. As discussed above, proximal portion 210 may be a more flexible wire, cable, suture, composite material or the like 290 that is connectable to distal portion 220.

These portions may alternatively comprise separate elements joined to one another at optional shoulder 240 via any number of techniques as previously described. Shoulder 240 may be used to aid in deploying the tissue localization device and helps to anchor the tissue localization device in the tissue. It also provides tactile feedback to the surgeon during surgical excision. Wire 200 need not be of multiple-piece construction to have a shoulder feature; i.e., a unitary or single-piece wire 200 having shoulder 240 is within the scope of this invention.

We prefer that shoulder 240 be disposed at an intersection between proximal portion 210 and distal portion 220; however, shoulder 240 may be located along any portion of wire 200. For instance, shoulder 240 may be disposed within proximal portion 210 or within distal portion 220. Shoulder 240 preferably has a width about at least three times the width of the proximal portion 210 when used as a tissue localization wire; even more preferable is a shoulder width of about at least four times that of the proximal portion 210. Generally, we prefer a shoulder width of at least about 0.75 mm.

Other features and preferred aspects described herein for shoulder 240 may also be used for shoulder 240, including the optional tabs or flanges 246 shown in FIGS. 3F–3J. More than one set of tabs may be disposed at various locations along the length of wire 200, either within proximal portion 210, within distal portion 220, or within both distal and proximal portions as desired.

Tissue localization device 200 preferably has a non-circular cross section; more preferably a non-circular cross-section in which a major axis of the cross section has a greater length than that of its minor axis. We have found that such a configuration provides for greater stability in tissue and allows device 200 to generally stay in a single plane as it curves through the tissue during deployment. Suitable ratios of the major axis length to minor axis length range from about 2 to about 8 or higher; most suitable are ratios ranging from about 2 to about 4.

Especially preferable is a wire 200 having a flat or rectangular cross section as previously described. However, other non-circular cross-sectional profiles, such as elliptical, irregular, etc., are within the scope of the invention, as are circular profiles in which the localization device 200 cross section major and minor axes have generally equal lengths. We prefer both proximal portion 210 and distal portion 220 to have the same cross-sectional shape, although this need not be the case.

When used as a tissue localization wire, device 200 is generally more effective if it has a slightly smaller cross-sectional area than when it is used as a locator element. For instance, we prefer the major axis length, or width, of a flat or rectangular localization wire distal portion 220 to be between about 0.5 to 1.5 mm; especially preferable is a width of about 0.75 mm. Likewise, its minor axis length, or thickness, should be between about 0.1 and 0.5 mm; especially preferable is a thickness of about 0.2 mm.

If distal portion 220 has a generally circular cross section, its diameter (or major axis if the wire cross section is elliptical) should preferably be between about 0.25 mm and 0.5 mm. Especially preferable is a diameter of between about 0.3 mm and 0.4 mm.

Preferably, although not necessarily, proximal portion 210 has a smaller cross-sectional area than distal portion 220 so to improve patient comfort.

FIGS. 36A and 36B show distal portions of two alternative localization device assemblies 130 in perspective. The assembly of FIG. 36A is similar to that described above in conjunction with FIG. 3B. Here, proximal portion 210 of a flat tissue localization device 200 is partially disposed in the lumen 712 of pusher or stiffening tube 730; in turn, this combination is disposed in lumen 310 of deployment tube 300. Although we prefer that a flat wire 200 be deployed through a lumen 310 having a generally oval cross-section as shown, the invention is not so limited. Lumen 310 and the outside shape of tube 300 may identically or separately have a variety of other cross-sectional shapes, including circular, rectangular, irregular, etc.

FIG. 36B depicts an assembly in which wire 200 and deployment tube 300 generally have circular cross sections. Here, the deployment tube has a circular cross section such as that of a stainless steel hypotube. Typical diameters for circular deployment tube 300 range from about 24 gage (0.022 inch) to about 15 gage (0.072 inch). We prefer a diameter range of between about 21 gage (0.032 inch) and 18 gage (0.049 inch).

We also prefer that deployment tube 300 have a sharpened distal tip (as described in conjunction with the locator element embodiments of FIGS. 4D–4E) to facilitate safe and reliable entry into tissue by cutting and/or dilating action. Other features and advantages of the locator element deployment tube embodiments described herein may be used in the localization wire deployment tube 300 as well.

FIG. 37 shows the assembly of FIG. 36A with an optional proximal hub 340 and port 342 in fluid communication with the deployment tube lumen 310. Hub 340 and port 342 may be used to deliver one or more agents to tissue via the deployment tube lumen 310 as described above in conjunction with tubular member 660 of blade 600. It should be understood that hubs and ports may be added to any of the tubular members of this invention for therapeutic or diagnostic fluid delivery.

Stiffening tube 730 may also be provided with one or more apertures (not shown) through which such agents can be delivered directly to the targeted tissue. Wire 200 may also be partially or completely coated with silicone, TEFLON (E.I. du Pont de Nemours and Company, Wilmington, Del.), or the like, for additional lubricity.

Optional localization wire stiffening tube 730, such as that discussed above in conjunction with the pusher assembly embodiments shown in FIGS. 2, 7A–7C, and 13–16, for example, fits within the deployment tube lumen 310. Stiffening tube 730 may serve the same functions as pusher tube 730 previously described; however, in the event that wire 200 has no shoulder 240, the stiffening tube still supports wire 200 to facilitate the wire's entry into tissue and to provide the wire with added stability.

Stiffening tube 730 may not be necessary for certain configurations of the invention as herein described. For example, it may not be needed if the cross-sectional areas and stiffnesses of the wire proximal portion 210 and distal portion 220 generally are the same.

Stiffening tube 730 should have a length generally equal to or less than that of tissue localization wire 200. More preferably, stiffening tube 730 should have a length suitable to accommodate proximal portion 210 of wire 200, especially if shoulder 240 is present. Tube 730 may comprise any suitable material as discussed throughout the specification, such as stainless steel. Stiffening tube 730 may optionally comprise a high durometer electrically insulative plastic or have an insulative coating to protect it from electrocautery during tissue removal.

Stiffening tube lumen 712 should generally conform to the cross-sectional size and shape of the wire proximal portion 210. This allows the stiffening tube to better support wire 200 during and after deployment into the tissue of interest. As such, stiffening tube 730 and its lumen 712 should be designed to prevent, or at least make more difficult, bending of the wire proximal portion 210. The particular properties of stiffening tube 730 (as well as other components of assembly 130) may be tailored to the application for which it is intended so that the physician can select a tissue localization "kit" having the desired attributes.

If present, optional shoulder 240 should be prevented from fitting into lumen 712 so to present a surface against which the stiffening tube may abut to aid the physician in deploying wire 200 into the tissue of interest as discussed above.

One or more optional clamping ferrules 710, such as those discussed above in conjunction with FIGS. 2 and 7C, may be included in assembly 130. Ferrule 710 includes an adjustable fastener or wire lock 720 in the form of a screw reversibly threaded through the clamping ferrule 710 and extending into stiffening tube lumen 710. Lock 720 may also be directly disposed through an aperture in the stiffening tube wall 732 without a ferrule 710. The ferrule/screw arrangements shown in FIGS. 2 and 7C are but two of many that are capable of unifying wire 200 and stiffening tube 730 so that they may be advanced as a single unit into the tissue of interest.

FIGS. 38–42 depict the use of assembly 130 of FIGS. 36A and 37 to deploy wire 200 into breast tissue. Optional hub 340, fluid port 342, wire lock 720 and ferrule 710 are omitted for clarity. Wire 200 is deployed in much the same fashion as that of locator element 200 (see, e.g., FIGS. 9–17 and the accompanying description), except that the tissue volume of interest (which may or may not include lesion 20) may be penetrated by wire 200. In addition, when the simplified assembly 130 is used, many of the components described in conjunction with the locator element, such as compression paddles 30, stereotactic guide unit 80, driver tube 400, etc., need not be used.

We prefer that localization device 200 be adapted to deploy in a polar configuration, although a tangential deployment is possible. In most instances, only a single localization device 200 need deployed into lesion 20. Multiple wires, however, may be deployed as the physician sees fit.

Once the tissue 10 has been identified and prepared by the techniques described above, assembly 130 is deployed to mark the tissue 10 and/or lesion 20. As discussed in conjunction with FIGS. 7–14, we prefer that deployment tube 300 be generally centered over lesion 20.

A first step is shown in FIG. 38, in which deployment tube 300 has penetrated tissue 10 via a sharpened distal tip. Proximal portion 210 of the unitary, flat localization wire 200 is shown disposed in the lumen 712 of stiffening tube 730; wire 200 and stiffening tube 730 in turn are disposed in the deployment tube lumen 310. Note that the views of localization wire 200 in FIGS. 38–42 are along its width, so one only sees the uniform thickness of the tissue localization device 200 moving from proximal portion 210 to distal portion 220. The distal end of stiffening tube 730 is shown where it abuts shoulder 240.

Once the deployment tube is advanced to the desired position adjacent lesion 20, the physician advances tissue localization wire 200 and stiffening tube 730 (which are preferably fixed to one another via optional wire lock or thumbscrew 720, not shown) just into tissue 10 as shown in FIG. 39. Optionally, deployment tube 300, stiffening tube 730 and wire 200 may be advanced simultaneously into tissue 10 with the distal end of deployment tube 300 leading the way.

After the physician or surgeon confirms the accuracy of assembly placement, she will then release lock 720, allowing wire 200 to move freely within stiffening tube 730. As shown in FIGS. 40–42, the wire is advanced into tissue 10 outside lumen 310 of deployment tube 300 distal end in polar fashion, with the wire distal anchoring portion 220 taking on its predetermined curved shape and proximal portion 210 remaining straight to define a longitudinal axis 212.

A polar deployment mode allows the user to target the center of the lesion with deployment tube 300, and ensures that the loop created by the deployed localization wire is centered in, through, or near lesion 20. This also adds a degree of stability to the lesion to aid the surgeon in tissue excision. Note that a key feature of localization wire 200 is that it may penetrate at least a portion of lesion 20 as shown in FIGS. 40–42.

When so deployed, the curved distal portion 220 defines a central axis that preferably is substantially aligned with the proximal portion 212. That is to say, imaginary rotation of curved distal portion 220 about longitudinal axis 212 through 360 degrees defines a volume of tissue including at least a portion of lesion 20 having a central axis that is substantially aligned with longitudinal axis 212.

We prefer that as the wire distal portion 220 is being deployed, the wire distal tip 230 follows a curvilinear path extending at least approximately 360 degrees. Distal tip 230 may even extend beyond 360 degrees if desired. This affords the surgeon a degree of protection from what may otherwise be an exposed distal tip 230.

As discussed above in the context of the deployment of a locator element, additional wires may be deployed as the physician sees fit.

After the physician confirms the position of wire 200 via mammographic or other suitable means, stiffening tube 730 (if present) and deployment tube 300 may be withdrawn from the breast and the free end of proximal portion 210 may be placed in pouch 110 or taped to the patient's skin as described herein. The patient is now ready to be sent to the surgeon for removal of lesion 20. Optionally, prior to surgical removal of the lesion, a stiffening tube 730 may be reinstalled over the wire proximal portion 210 to aid in the lesion removal procedure.

Optionally, one or more locator elements 200 may be deployed to mark the border of the lesion as described herein. During subsequent excision along this border, the deployed localization wire helps to keep the lesion stable and subsequently maintain the orientation of the excised tissue.

The invention herein is described by examples and a particularly desired way of practicing the invention has been described. However, the invention as claimed herein is not limited to that specific description in any manner. Elements and features described in conjunction with a particular embodiment are not limited to use therewith and may be used separately or in conjunction with the other embodiments disclosed herein. Equivalence to the description as hereinafter claimed is considered to be within the scope of protection of this patent.

We claim the following:

1. A tissue localizing device adapted for deployment within tissue of a human patient comprising:
   a locator element, the locator element having a distal tip, a curved anchoring portion having a non-circular cross-section, and a proximal shoulder; and
   one or more anchoring tabs extending from the locator element.
2. The device of claim 1 wherein the curved anchoring portion has a cross-section having a width greater than its height.
3. The device of claim 1 wherein the curved anchoring portion forms a loop.
4. The device of claim 1 wherein the anchoring tabs extend from the shoulder.
5. The device of claim 1 wherein the anchoring tabs extend from the anchoring portion at a location distal to the shoulder.
6. The device of claim 1 wherein the anchoring tabs extend within a plane defined by the locator element.
7. The device of claim 1 wherein the anchors extend outside a plane defined by the locator element.
8. The device of claim 1 wherein the locator element is formed of a superelastic material.
9. The device of claim 1 wherein the locator element is formed of a shape memory alloy.
10. The device of claim 1 further comprising a flexible elongate lead extending from the shoulder.
11. The device of claim 10 wherein the flexible elongate lead further comprises a flexible wire.
12. The device of claim 10 wherein the flexible elongate lead is integral to the locator element.
13. A delivery device for delivering the tissue localization device of claim 1, the delivery device comprising:
    a housing having a housing lumen and a longitudinal slot in communication with the housing lumen
    a pusher slidably disposed in the housing lumen and adapted to receive the shoulder of the tissue localization device of claim 1 and having a control lever extending through the housing slot;
    a delivery tube affixed to the housing and having a delivery tube lumen adapted for slidably receiving the pusher and the tissue localization device of claim 1.
14. The delivery device of claim 13 wherein said delivery tube lumen is configured to slidably receive two or more tissue localization devices according to claim 1.
15. The delivery device of claim 14 wherein said delivery tube lumen is further configured such that said two or more tissue localization devices according to claim 1 can be slidably received within the delivery tube lumen at relative angles to one another.

* * * * *